US011427618B2

(12) United States Patent
Li et al.

(10) Patent No.: US 11,427,618 B2
(45) Date of Patent: Aug. 30, 2022

(54) MUTANT OF L1 PROTEIN OF HUMAN PAPILLOMAVIRUS TYPE 39

(71) Applicants: Xiamen University, Fujian (CN); Xiamen Innovax Biotech Co., Ltd., Fujian (CN)

(72) Inventors: Shaowei Li, Fujian (CN); Daning Wang, Fujian (CN); Zhiping Wang, Fujian (CN); Xinlin Liu, Fujian (CN); Jun Zhang, Fujian (CN); Ningshao Xia, Fujian (CN)

(73) Assignees: XIAMEN UNIVERSITRY, Fujian (CN); XIAMEN INNOVAX BIOTECH, CO., LTD., Fujian (CN)

( * ) Notice: Subject to any disclaimer, the term of this patent is extended or adjusted under 35 U.S.C. 154(b) by 0 days.

(21) Appl. No.: 15/734,715

(22) PCT Filed: Jun. 4, 2019

(86) PCT No.: PCT/CN2019/089988
§ 371 (c)(1),
(2) Date: Dec. 3, 2020

(87) PCT Pub. No.: WO2019/233415
PCT Pub. Date: Dec. 12, 2019

(65) Prior Publication Data
US 2021/0198322 A1    Jul. 1, 2021

(30) Foreign Application Priority Data

Jun. 4, 2018  (CN) .......................... 201810563378.0

(51) Int. Cl.
| C07K 14/025 | (2006.01) |
| A61K 39/12 | (2006.01) |
| C12N 7/00 | (2006.01) |
| C12N 15/70 | (2006.01) |
| A61K 39/00 | (2006.01) |

(52) U.S. Cl.
CPC ............ *C07K 14/025* (2013.01); *A61K 39/12* (2013.01); *C12N 7/00* (2013.01); *C12N 15/70* (2013.01); *A61K 2039/5258* (2013.01); *C12N 2710/20023* (2013.01); *C12N 2710/20034* (2013.01)

(58) Field of Classification Search
None
See application file for complete search history.

(56) References Cited

U.S. PATENT DOCUMENTS 10,413,603 B2 * 9/2019 Garcea ................... A61K 39/12

FOREIGN PATENT DOCUMENTS

CN     1091914139 X     11/2012

OTHER PUBLICATIONS

Bissett et al. Pre-clinical immunogenicity of human papillomavirus alpha-7 andalpha-9 major capsid proteins. Vaccine 32 (2014) 6548-6555.*
International Search Report, issued in PCT/CN2019/089988, dated Aug. 22, 2019.
Varsani et al., "Chimeric Human Papillomavirus Type 16 (HPB-16) L1 Particles Presenting the Common Neutralizing Epitope for the L2 Minor Capsid Protein of HPV-6 and HPV-16," Journal of Virology, vol. 77, No. 15, (2003), pp. 3386-8393.
Extended European Search Report, issued in 19815471.8, dated Mar. 3, 2022.
Herd, KA et al., "Recombinant Kunjin Virus Replicon Vaccines Induce Protective T-Cell Immunity Against Human Papillomavirus 16 E7-Expressing Tumour". Virology, Elsevier, Amsterdam, NL, Feb. 20, 2004, vol. 319, No. 2.
Bogers, Willy M et al., "Potent Immune Responses in Rhesus Macaques Induced By Nonviral Delivery of a Self-Amplifying RNA Vaccine Expressing HIV Type 1 Envelope With a Cationic Nanoemulsion". The Journal of Infectious Diseases, Infectious Diseases Society of America, US, Mar. 15, 2015, vol. 211, No. 67.
Vici, Patrizia et al., Immunologic Treatments for Precancerous Lesions and Uterine Cervical Cancer. Journal of Experimental & Clinical Cancer Research, Biomed Central Ltd, London, UK, Mar. 26, 2014, vol. 33, No. 1.

* cited by examiner

*Primary Examiner* — Nianxiang Zou
(74) *Attorney, Agent, or Firm* — Barnes & Thornburg LLP

(57) ABSTRACT

The invention relates to a mutated HPV39 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV39 and HPV68, or HPV39, HPV68 and HPV70), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

20 Claims, 10 Drawing Sheets

Specification includes a Sequence Listing.

SEQUENCE LISTING

<160> NUMBER OF SEQ ID NOS: 71

<210> SEQ ID NO 1
<211> LENGTH: 505
<212> TYPE: PRT
<213> ORGANISM: Human papillomavirus type 39

<400> SEQUENCE: 1

Met Ala Leu Trp Arg Ser Ser Asp Ser Met Val Tyr Leu Pro Pro Pro
1               5                   10                  15

Ser Val Ala Lys Val Val Asn Thr Asp Asp Tyr Val Thr Arg Thr Gly
            20                  25                  30

Ile Tyr Tyr Tyr Ala Gly Ser Ser Arg Leu Leu Thr Val Gly His Pro
        35                  40                  45

Tyr Phe Lys Val Gly Met Asn Gly Gly Arg Lys Gln Asp Ile Pro Lys
    50                  55                  60

Val Ser Ala Tyr Gln Tyr Arg Val Phe Arg Val Thr Leu Pro Asp Pro
65                  70                  75                  80

Asn Lys Phe Ser Ile Pro Asp Ala Ser Leu Tyr Asn Pro Glu Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Tyr Asn Arg Gln Asp Asp
        115                 120                 125

Thr Glu Asn Ser Pro Phe Ser Ser Thr Asn Lys Asp Ser Arg Asp
    130                 135                 140

Asn Val Ser Val Asp Tyr Lys Gln Thr Gln Leu Cys Ile Ile Gly Cys
145                 150                 155                 160

Val Pro Ala Ile Gly Glu His Trp Gly Lys Gly Lys Ala Cys Lys Pro
                165                 170                 175

Asn Asn Val Ser Thr Gly Asp Cys Pro Pro Leu Glu Leu Val Asn Thr
            180                 185                 190

Pro Ile Glu Asp Gly Asp Met Ile Asp Thr Gly Tyr Gly Ala Met Asp
        195                 200                 205

Phe Gly Ala Leu Gln Glu Thr Lys Ser Glu Val Pro Leu Asp Ile Cys
    210                 215                 220

Gln Ser Ile Cys Lys Tyr Pro Asp Tyr Leu Gln Met Ser Ala Asp Val
225                 230                 235                 240

Tyr Gly Asp Ser Met Phe Phe Cys Leu Arg Arg Glu Gln Leu Phe Ala
                245                 250                 255

Arg His Phe Trp Asn Arg Gly Gly Met Val Gly Asp Ala Ile Pro Ala
            260                 265                 270

Gln Leu Tyr Ile Lys Gly Thr Asp Ile Arg Ala Asn Pro Gly Ser Ser
        275                 280                 285

Val Tyr Cys Pro Ser Pro Ser Gly Ser Met Val Thr Ser Asp Ser Gln
    290                 295                 300

Leu Phe Asn Lys Pro Tyr Trp Leu His Lys Ala Gln Gly His Asn Asn
305                 310                 315                 320

Gly Ile Cys Trp His Asn Gln Leu Phe Leu Thr Val Val Asp Thr Thr
                325                 330                 335

Arg Ser Thr Asn Phe Thr Leu Ser Thr Ser Ile Glu Ser Ser Ile Pro
            340                 345                 350

Ser Thr Tyr Asp Pro Ser Lys Phe Lys Glu Tyr Thr Arg His Val Glu
        355                 360                 365

```
Glu Tyr Asp Leu Gln Phe Ile Phe Gln Leu Cys Thr Val Thr Leu Thr
    370             375             380

Thr Asp Val Met Ser Tyr Ile His Thr Met Asn Ser Ser Ile Leu Asp
385             390             395             400

Asn Trp Asn Phe Ala Val Ala Pro Pro Ser Ala Ser Leu Val Asp
            405             410             415

Thr Tyr Arg Tyr Leu Gln Ser Ala Ala Ile Thr Cys Gln Lys Asp Ala
            420             425             430

Pro Ala Pro Glu Lys Lys Asp Pro Tyr Asp Gly Leu Lys Phe Trp Asn
            435             440             445

Val Asp Leu Arg Glu Lys Phe Ser Leu Glu Leu Asp Gln Phe Pro Leu
450             455             460

Gly Arg Lys Phe Leu Leu Gln Ala Arg Val Arg Arg Pro Thr Ile
465             470             475             480

Gly Pro Arg Lys Arg Pro Ala Ala Ser Thr Ser Ser Ser Ser Ala Thr
            485             490             495

Lys His Lys Arg Lys Arg Val Ser Lys
            500             505

<210> SEQ ID NO 2
<211> LENGTH: 505
<212> TYPE: PRT
<213> ORGANISM: Human papillomavirus type 68

<400> SEQUENCE: 2

Met Ala Leu Trp Arg Ala Ser Asp Asn Met Val Tyr Leu Pro Pro Pro
1               5               10              15

Ser Val Ala Lys Val Val Asn Thr Asp Asp Tyr Val Thr Arg Thr Gly
                20              25              30

Met Tyr Tyr Tyr Ala Gly Thr Ser Arg Leu Leu Thr Val Gly His Pro
            35              40              45

Tyr Phe Lys Val Pro Met Ser Gly Gly Arg Lys Gln Gly Ile Pro Lys
    50              55              60

Val Ser Ala Tyr Gln Tyr Arg Val Phe Arg Val Thr Leu Pro Asp Pro
65              70              75              80

Asn Lys Phe Ser Val Pro Glu Ser Thr Leu Tyr Asn Pro Asp Thr Gln
                85              90              95

Arg Met Val Trp Ala Cys Val Gly Val Glu Ile Gly Arg Gly Gln Pro
            100             105             110

Leu Gly Val Gly Leu Ser Gly His Pro Leu Tyr Asn Arg Leu Asp Asp
        115             120             125

Thr Glu Asn Ser Pro Phe Ser Ser Asn Lys Asn Pro Lys Asp Ser Arg
    130             135             140

Asp Asn Val Ala Val Asp Cys Lys Gln Thr Gln Leu Cys Ile Ile Gly
145             150             155             160

Cys Val Pro Ala Ile Gly Glu His Trp Ala Lys Gly Lys Ser Cys Lys
                165             170             175

Pro Thr Asn Val Gln Gln Gly Asp Cys Pro Pro Leu Glu Leu Val Asn
            180             185             190

Thr Pro Ile Glu Asp Gly Asp Met Ile Asp Thr Gly Tyr Gly Ala Met
        195             200             205

Asp Phe Gly Thr Leu Gln Glu Thr Lys Ser Glu Val Pro Leu Asp Ile
    210             215             220

Cys Gln Ser Val Cys Lys Tyr Pro Asp Tyr Leu Gln Met Ser Ala Asp
225             230             235             240
```

```
Val Tyr Gly Asp Ser Met Phe Phe Cys Leu Arg Arg Glu Gln Leu Phe
                245                 250                 255

Ala Arg His Phe Trp Asn Arg Gly Gly Met Val Gly Asp Thr Ile Pro
            260                 265                 270

Thr Asp Met Tyr Ile Lys Gly Thr Asp Ile Arg Glu Thr Pro Ser Ser
        275                 280                 285

Tyr Val Tyr Ala Pro Ser Pro Ser Gly Ser Met Val Ser Ser Asp Ser
    290                 295                 300

Gln Leu Phe Asn Lys Pro Tyr Trp Leu His Lys Ala Gln Gly His Asn
305                 310                 315                 320

Asn Gly Ile Cys Trp His Asn Gln Leu Phe Leu Thr Val Val Asp Thr
                325                 330                 335

Thr Arg Ser Thr Asn Phe Thr Leu Ser Thr Thr Thr Asp Ser Thr Val
            340                 345                 350

Pro Ala Val Tyr Asp Ser Asn Lys Phe Lys Glu Tyr Val Arg His Val
        355                 360                 365

Glu Glu Tyr Asp Leu Gln Phe Ile Phe Gln Leu Cys Thr Ile Thr Leu
    370                 375                 380

Ser Thr Asp Val Met Ser Tyr Ile His Thr Met Asn Pro Ala Ile Leu
385                 390                 395                 400

Asp Asp Trp Asn Phe Gly Val Ala Pro Pro Ser Ala Ser Leu Val
                405                 410                 415

Asp Thr Tyr Arg Tyr Leu Gln Ser Ala Ala Ile Thr Cys Gln Lys Asp
            420                 425                 430

Ala Pro Ala Pro Val Lys Lys Asp Pro Tyr Asp Gly Leu Asn Phe Trp
        435                 440                 445

Asn Val Asp Leu Lys Glu Lys Phe Ser Ser Glu Leu Asp Gln Phe Pro
    450                 455                 460

Leu Gly Arg Lys Phe Leu Leu Gln Ala Gly Val Arg Arg Pro Thr
465                 470                 475                 480

Ile Gly Pro Arg Lys Arg Thr Ala Thr Ala Ala Thr Ser Thr Ser
                485                 490                 495

Lys His Lys Arg Lys Arg Val Ser Lys
            500                 505

<210> SEQ ID NO 3
<211> LENGTH: 506
<212> TYPE: PRT
<213> ORGANISM: Human papillomavirus type 70

<400> SEQUENCE: 3

Met Ala Leu Trp Arg Ser Ser Asp Asn Thr Val Tyr Leu Pro Pro Pro
1               5                   10                  15

Ser Val Ala Lys Val Val Asn Thr Asp Asp Tyr Val Thr Arg Thr Gly
                20                  25                  30

Ile Tyr Tyr Tyr Ala Gly Ser Ser Arg Leu Leu Thr Val Gly His Pro
            35                  40                  45

Tyr Phe Lys Val Pro Val Asn Gly Gly Arg Lys Gln Glu Ile Pro Lys
        50                  55                  60

Val Ser Ala Tyr Gln Tyr Arg Val Phe Arg Val Ser Leu Pro Asp Pro
65                  70                  75                  80

Asn Lys Phe Gly Leu Pro Asp Pro Ser Leu Tyr Asn Pro Asp Thr Gln
                85                  90                  95

Arg Leu Val Trp Ala Cys Ile Gly Val Glu Ile Gly Arg Gly Gln Pro
```

```
              100                 105                 110
Leu Gly Val Gly Val Ser Gly His Pro Leu Tyr Asn Arg Leu Asp Asp
            115                 120                 125

Thr Glu Asn Ser His Phe Ser Ala Val Asn Thr Gln Asp Ser Arg
130                 135                 140

Asp Asn Val Ser Val Asp Tyr Lys Gln Thr Gln Leu Cys Ile Ile Gly
145                 150                 155                 160

Cys Val Pro Ala Met Gly Glu His Trp Ala Lys Gly Lys Ala Cys Lys
                165                 170                 175

Ser Thr Thr Val Gln Gln Gly Asp Cys Pro Pro Leu Glu Leu Val Asn
                180                 185                 190

Thr Ala Ile Glu Asp Gly Asp Met Ile Asp Thr Gly Tyr Gly Ala Met
                195                 200                 205

Asp Phe Arg Thr Leu Gln Glu Thr Lys Ser Glu Val Pro Leu Asp Ile
            210                 215                 220

Cys Gln Ser Val Cys Lys Tyr Pro Asp Tyr Leu Gln Met Ser Ala Asp
225                 230                 235                 240

Val Tyr Gly Asp Ser Met Phe Phe Cys Leu Arg Lys Glu Gln Leu Phe
                245                 250                 255

Ala Arg His Phe Trp Asn Arg Gly Gly Met Val Gly Asp Thr Ile Pro
                260                 265                 270

Ser Glu Leu Tyr Ile Lys Gly Thr Asp Ile Arg Asp Arg Pro Gly Thr
                275                 280                 285

His Val Tyr Ser Pro Ser Pro Ser Gly Ser Met Val Ser Ser Asp Ser
            290                 295                 300

Gln Leu Phe Asn Lys Pro Tyr Trp Leu His Lys Ala Gln Gly His Asn
305                 310                 315                 320

Asn Gly Ile Cys Trp His Asn Gln Leu Phe Ile Thr Val Val Asp Thr
                325                 330                 335

Thr Arg Ser Thr Asn Phe Thr Leu Ser Ala Cys Thr Glu Thr Ala Ile
                340                 345                 350

Pro Ala Val Tyr Ser Pro Thr Lys Phe Lys Glu Tyr Thr Arg His Val
                355                 360                 365

Glu Glu Tyr Asp Leu Gln Phe Ile Phe Gln Leu Cys Thr Ile Thr Leu
370                 375                 380

Thr Ala Asp Val Met Ala Tyr Ile His Thr Met Asn Pro Ala Ile Leu
385                 390                 395                 400

Asp Asn Trp Asn Ile Gly Val Thr Pro Pro Ser Ala Ser Leu Val
                405                 410                 415

Asp Thr Tyr Arg Tyr Leu Gln Ser Ala Ala Ile Ala Cys Gln Lys Asp
                420                 425                 430

Ala Pro Ala Pro Glu Lys Lys Asp Pro Tyr Asp Asp Leu Lys Phe Trp
                435                 440                 445

Asn Val Asp Leu Lys Glu Lys Phe Ser Thr Glu Leu Asp Gln Phe Pro
            450                 455                 460

Leu Gly Arg Lys Phe Leu Leu Gln Val Gly Ala Arg Arg Pro Thr
465                 470                 475                 480

Ile Gly Pro Arg Lys Arg Pro Ala Ser Ala Lys Ser Ser Ser Ser Ala
                485                 490                 495

Ser Lys His Lys Arg Lys Arg Val Ser Lys
                500                 505
```

<210> SEQ ID NO 4

```
<211> LENGTH: 491
<212> TYPE: PRT
<213> ORGANISM: Artificial Sequence
<220> FEATURE:
<223> OTHER INFORMATION: H39N15-68T1

<400> SEQUENCE: 4
```

| | | | | | | | | | | | | | | | |
|---|---|---|---|---|---|---|---|---|---|---|---|---|---|---|---|
| Met | Pro | Ser | Val | Ala | Lys | Val | Val | Asn | Thr | Asp | Asp | Tyr | Val | Thr | Arg |
| 1 | | | | 5 | | | | | 10 | | | | | 15 | |
| Thr | Gly | Ile | Tyr | Tyr | Ala | Gly | Ser | Ser | Arg | Leu | Leu | Thr | Val | Gly | |
| | | | 20 | | | | | 25 | | | | | 30 | | |
| His | Pro | Tyr | Phe | Lys | Val | Pro | Met | Ser | Gly | Gly | Arg | Lys | Gln | Gly | Ile |
| | | | 35 | | | | | 40 | | | | | 45 | | |
| Pro | Lys | Val | Ser | Ala | Tyr | Gln | Tyr | Arg | Val | Phe | Arg | Val | Thr | Leu | Pro |
| | 50 | | | | | 55 | | | | | 60 | | | | |
| Asp | Pro | Asn | Lys | Phe | Ser | Ile | Pro | Asp | Ala | Ser | Leu | Tyr | Asn | Pro | Glu |
| 65 | | | | | 70 | | | | | 75 | | | | | 80 |
| Thr | Gln | Arg | Leu | Val | Trp | Ala | Cys | Val | Gly | Val | Glu | Val | Gly | Arg | Gly |
| | | | | 85 | | | | | 90 | | | | | 95 | |
| Gln | Pro | Leu | Gly | Val | Gly | Ile | Ser | Gly | His | Pro | Leu | Tyr | Asn | Arg | Gln |
| | | | 100 | | | | | 105 | | | | | 110 | | |
| Asp | Asp | Thr | Glu | Asn | Ser | Pro | Phe | Ser | Ser | Thr | Thr | Asn | Lys | Asp | Ser |
| | | | 115 | | | | | 120 | | | | | 125 | | |
| Arg | Asp | Asn | Val | Ser | Val | Asp | Tyr | Lys | Gln | Thr | Gln | Leu | Cys | Ile | Ile |
| | 130 | | | | | 135 | | | | | 140 | | | | |
| Gly | Cys | Val | Pro | Ala | Ile | Gly | Glu | His | Trp | Gly | Lys | Gly | Lys | Ala | Cys |
| 145 | | | | | 150 | | | | | 155 | | | | | 160 |
| Lys | Pro | Asn | Asn | Val | Ser | Thr | Gly | Asp | Cys | Pro | Pro | Leu | Glu | Leu | Val |
| | | | | 165 | | | | | 170 | | | | | 175 | |
| Asn | Thr | Pro | Ile | Glu | Asp | Gly | Asp | Met | Ile | Asp | Thr | Gly | Tyr | Gly | Ala |
| | | | 180 | | | | | 185 | | | | | 190 | | |
| Met | Asp | Phe | Gly | Ala | Leu | Gln | Glu | Thr | Lys | Ser | Glu | Val | Pro | Leu | Asp |
| | | | 195 | | | | | 200 | | | | | 205 | | |
| Ile | Cys | Gln | Ser | Ile | Cys | Lys | Tyr | Pro | Asp | Tyr | Leu | Gln | Met | Ser | Ala |
| | 210 | | | | | 215 | | | | | 220 | | | | |
| Asp | Val | Tyr | Gly | Asp | Ser | Met | Phe | Phe | Cys | Leu | Arg | Arg | Glu | Gln | Leu |
| 225 | | | | | 230 | | | | | 235 | | | | | 240 |
| Phe | Ala | Arg | His | Phe | Trp | Asn | Arg | Gly | Gly | Met | Val | Gly | Asp | Ala | Ile |
| | | | | 245 | | | | | 250 | | | | | 255 | |
| Pro | Ala | Gln | Leu | Tyr | Ile | Lys | Gly | Thr | Asp | Ile | Arg | Ala | Asn | Pro | Gly |
| | | | 260 | | | | | 265 | | | | | 270 | | |
| Ser | Ser | Val | Tyr | Cys | Pro | Ser | Pro | Gly | Ser | Met | Val | Thr | Ser | Asp |
| | | | 275 | | | | | 280 | | | | | 285 | | |
| Ser | Gln | Leu | Phe | Asn | Lys | Pro | Tyr | Trp | Leu | His | Lys | Ala | Gln | Gly | His |
| | 290 | | | | | 295 | | | | | 300 | | | | |
| Asn | Asn | Gly | Ile | Cys | Trp | His | Asn | Gln | Leu | Phe | Leu | Thr | Val | Val | Asp |
| 305 | | | | | 310 | | | | | 315 | | | | | 320 |
| Thr | Thr | Arg | Ser | Thr | Asn | Phe | Thr | Leu | Ser | Thr | Ser | Ile | Glu | Ser | Ser |
| | | | | 325 | | | | | 330 | | | | | 335 | |
| Ile | Pro | Ser | Thr | Tyr | Asp | Pro | Ser | Lys | Phe | Lys | Glu | Tyr | Thr | Arg | His |
| | | | 340 | | | | | 345 | | | | | 350 | | |
| Val | Glu | Glu | Tyr | Asp | Leu | Gln | Phe | Ile | Phe | Gln | Leu | Cys | Thr | Val | Thr |
| | | | 355 | | | | | 360 | | | | | 365 | | |
| Leu | Thr | Thr | Asp | Val | Met | Ser | Tyr | Ile | His | Thr | Met | Asn | Ser | Ser | Ile |
| | 370 | | | | | 375 | | | | | 380 | | | | |

```
Leu Asp Asn Trp Asn Phe Ala Val Ala Pro Pro Ser Ala Ser Leu
385                 390                 395                 400

Val Asp Thr Tyr Arg Tyr Leu Gln Ser Ala Ile Thr Cys Gln Lys
            405                 410                 415

Asp Ala Pro Ala Pro Glu Lys Lys Asp Pro Tyr Asp Gly Leu Lys Phe
        420                 425                 430

Trp Asn Val Asp Leu Arg Glu Lys Phe Ser Leu Glu Leu Asp Gln Phe
            435                 440                 445

Pro Leu Gly Arg Lys Phe Leu Leu Gln Ala Arg Val Arg Arg Pro
    450                 455                 460

Thr Ile Gly Pro Arg Lys Arg Pro Ala Ala Ser Thr Ser Ser Ser
465                 470                 475                 480

Ala Thr Lys His Lys Arg Lys Arg Val Ser Lys
                485                 490

<210> SEQ ID NO 5
<211> LENGTH: 492
<212> TYPE: PRT
<213> ORGANISM: Artificial Sequence
<220> FEATURE:
<223> OTHER INFORMATION: H39N15-68T2

<400> SEQUENCE: 5

Met Pro Ser Val Ala Lys Val Val Asn Thr Asp Asp Tyr Val Thr Arg
1               5                   10                  15

Thr Gly Ile Tyr Tyr Ala Gly Ser Ser Arg Leu Leu Thr Val Gly
            20                  25                  30

His Pro Tyr Phe Lys Val Gly Met Asn Gly Gly Arg Lys Gln Asp Ile
            35                  40                  45

Pro Lys Val Ser Ala Tyr Gln Tyr Arg Val Phe Arg Val Thr Leu Pro
    50                  55                  60

Asp Pro Asn Lys Phe Ser Ile Pro Asp Ala Ser Leu Tyr Asn Pro Glu
65                  70                  75                  80

Thr Gln Arg Leu Val Trp Ala Cys Val Gly Val Glu Val Gly Arg Gly
                85                  90                  95

Gln Pro Leu Gly Val Gly Leu Ser Gly His Pro Leu Tyr Asn Arg Leu
            100                 105                 110

Asp Asp Thr Glu Asn Ser Pro Phe Ser Ser Asn Lys Asn Pro Lys Asp
            115                 120                 125

Ser Arg Asp Asn Val Ala Val Asp Cys Lys Gln Thr Gln Leu Cys Ile
    130                 135                 140

Ile Gly Cys Val Pro Ala Ile Gly Glu His Trp Gly Lys Gly Lys Ala
145                 150                 155                 160

Cys Lys Pro Asn Asn Val Ser Thr Gly Asp Cys Pro Pro Leu Glu Leu
                165                 170                 175

Val Asn Thr Pro Ile Glu Asp Gly Asp Met Ile Asp Thr Gly Tyr Gly
            180                 185                 190

Ala Met Asp Phe Gly Ala Leu Gln Glu Thr Lys Ser Glu Val Pro Leu
            195                 200                 205

Asp Ile Cys Gln Ser Ile Cys Lys Tyr Pro Asp Tyr Leu Gln Met Ser
    210                 215                 220

Ala Asp Val Tyr Gly Asp Ser Met Phe Phe Cys Leu Arg Arg Glu Gln
225                 230                 235                 240

Leu Phe Ala Arg His Phe Trp Asn Arg Gly Gly Met Val Gly Asp Ala
                245                 250                 255
```

```
Ile Pro Ala Gln Leu Tyr Ile Lys Gly Thr Asp Ile Arg Ala Asn Pro
            260                 265                 270

Gly Ser Ser Val Tyr Cys Pro Ser Pro Ser Gly Ser Met Val Thr Ser
        275                 280                 285

Asp Ser Gln Leu Phe Asn Lys Pro Tyr Trp Leu His Lys Ala Gln Gly
    290                 295                 300

His Asn Asn Gly Ile Cys Trp His Asn Gln Leu Phe Leu Thr Val Val
305                 310                 315                 320

Asp Thr Thr Arg Ser Thr Asn Phe Thr Leu Ser Thr Ser Ile Glu Ser
                325                 330                 335

Ser Ile Pro Ser Thr Tyr Asp Pro Ser Lys Phe Lys Glu Tyr Thr Arg
            340                 345                 350

His Val Glu Glu Tyr Asp Leu Gln Phe Ile Phe Gln Leu Cys Thr Val
        355                 360                 365

Thr Leu Thr Thr Asp Val Met Ser Tyr Ile His Thr Met Asn Ser Ser
    370                 375                 380

Ile Leu Asp Asn Trp Asn Phe Ala Val Ala Pro Pro Ser Ala Ser
385                 390                 395                 400

Leu Val Asp Thr Tyr Arg Tyr Leu Gln Ser Ala Ala Ile Thr Cys Gln
                405                 410                 415

Lys Asp Ala Pro Ala Pro Glu Lys Lys Asp Pro Tyr Asp Gly Leu Lys
            420                 425                 430

Phe Trp Asn Val Asp Leu Arg Glu Lys Phe Ser Leu Glu Leu Asp Gln
        435                 440                 445

Phe Pro Leu Gly Arg Lys Phe Leu Leu Gln Ala Arg Val Arg Arg
    450                 455                 460

Pro Thr Ile Gly Pro Arg Lys Arg Pro Ala Ala Ser Thr Ser Ser Ser
465                 470                 475                 480

Ser Ala Thr Lys His Lys Arg Lys Arg Val Ser Lys
                485                 490

<210> SEQ ID NO 6
<211> LENGTH: 491
<212> TYPE: PRT
<213> ORGANISM: Artificial Sequence
<220> FEATURE:
<223> OTHER INFORMATION: H39N15-68T3

<400> SEQUENCE: 6

Met Pro Ser Val Ala Lys Val Val Asn Thr Asp Asp Tyr Val Thr Arg
1               5                   10                  15

Thr Gly Ile Tyr Tyr Tyr Ala Gly Ser Ser Arg Leu Leu Thr Val Gly
            20                  25                  30

His Pro Tyr Phe Lys Val Gly Met Asn Gly Gly Arg Lys Gln Asp Ile
        35                  40                  45

Pro Lys Val Ser Ala Tyr Gln Tyr Arg Val Phe Arg Val Thr Leu Pro
    50                  55                  60

Asp Pro Asn Lys Phe Ser Ile Pro Asp Ala Ser Leu Tyr Asn Pro Glu
65                  70                  75                  80

Thr Gln Arg Leu Val Trp Ala Cys Val Gly Val Glu Val Gly Arg Gly
                85                  90                  95

Gln Pro Leu Gly Val Gly Ile Ser Gly His Pro Leu Tyr Asn Arg Gln
            100                 105                 110

Asp Asp Thr Glu Asn Ser Pro Phe Ser Ser Thr Asn Lys Asp Ser
        115                 120                 125
```

Arg Asp Asn Val Ser Val Asp Tyr Lys Gln Thr Gln Leu Cys Ile Ile
130                 135                 140

Gly Cys Val Pro Ala Ile Gly Glu His Trp Ala Lys Gly Lys Ser Cys
145                 150                 155                 160

Lys Pro Thr Asn Val Gln Gln Gly Asp Cys Pro Pro Leu Glu Leu Val
                165                 170                 175

Asn Thr Pro Ile Glu Asp Gly Asp Met Ile Asp Thr Gly Tyr Gly Ala
                180                 185                 190

Met Asp Phe Gly Ala Leu Gln Glu Thr Lys Ser Glu Val Pro Leu Asp
            195                 200                 205

Ile Cys Gln Ser Ile Cys Lys Tyr Pro Asp Tyr Leu Gln Met Ser Ala
210                 215                 220

Asp Val Tyr Gly Asp Ser Met Phe Phe Cys Leu Arg Arg Glu Gln Leu
225                 230                 235                 240

Phe Ala Arg His Phe Trp Asn Arg Gly Gly Met Val Gly Asp Ala Ile
                245                 250                 255

Pro Ala Gln Leu Tyr Ile Lys Gly Thr Asp Ile Arg Ala Asn Pro Gly
                260                 265                 270

Ser Ser Val Tyr Cys Pro Ser Pro Ser Gly Ser Met Val Thr Ser Asp
            275                 280                 285

Ser Gln Leu Phe Asn Lys Pro Tyr Trp Leu His Lys Ala Gln Gly His
290                 295                 300

Asn Asn Gly Ile Cys Trp His Asn Gln Leu Phe Leu Thr Val Val Asp
305                 310                 315                 320

Thr Thr Arg Ser Thr Asn Phe Thr Leu Ser Thr Ser Ile Glu Ser Ser
                325                 330                 335

Ile Pro Ser Thr Tyr Asp Pro Ser Lys Phe Lys Glu Tyr Thr Arg His
                340                 345                 350

Val Glu Glu Tyr Asp Leu Gln Phe Ile Phe Gln Leu Cys Thr Val Thr
            355                 360                 365

Leu Thr Thr Asp Val Met Ser Tyr Ile His Thr Met Asn Ser Ser Ile
370                 375                 380

Leu Asp Asn Trp Asn Phe Ala Val Ala Pro Pro Pro Ser Ala Ser Leu
385                 390                 395                 400

Val Asp Thr Tyr Arg Tyr Leu Gln Ser Ala Ala Ile Thr Cys Gln Lys
                405                 410                 415

Asp Ala Pro Ala Pro Glu Lys Lys Asp Pro Tyr Asp Gly Leu Lys Phe
                420                 425                 430

Trp Asn Val Asp Leu Arg Glu Lys Phe Ser Leu Glu Leu Asp Gln Phe
            435                 440                 445

Pro Leu Gly Arg Lys Phe Leu Leu Gln Ala Arg Val Arg Arg Pro
450                 455                 460

Thr Ile Gly Pro Arg Lys Arg Pro Ala Ala Ser Thr Ser Ser Ser Ser
465                 470                 475                 480

Ala Thr Lys His Lys Arg Lys Arg Val Ser Lys
                485                 490

<210> SEQ ID NO 7
<211> LENGTH: 491
<212> TYPE: PRT
<213> ORGANISM: Artificial Sequence
<220> FEATURE:
<223> OTHER INFORMATION: H39N15-68T4

<400> SEQUENCE: 7

```
Met Pro Ser Val Ala Lys Val Val Asn Thr Asp Asp Tyr Val Thr Arg
1               5                   10                  15

Thr Gly Ile Tyr Tyr Ala Gly Ser Ser Arg Leu Leu Thr Val Gly
            20                  25                  30

His Pro Tyr Phe Lys Val Gly Met Asn Gly Arg Lys Gln Asp Ile
            35                  40                  45

Pro Lys Val Ser Ala Tyr Gln Tyr Arg Val Phe Arg Val Thr Leu Pro
    50                  55                  60

Asp Pro Asn Lys Phe Ser Ile Pro Asp Ala Ser Leu Tyr Asn Pro Glu
65                  70                  75                  80

Thr Gln Arg Leu Val Trp Ala Cys Val Gly Val Glu Val Gly Arg Gly
                85                  90                  95

Gln Pro Leu Gly Val Gly Ile Ser Gly His Pro Leu Tyr Asn Arg Gln
                100                 105                 110

Asp Asp Thr Glu Asn Ser Pro Phe Ser Ser Thr Asn Lys Asp Ser
            115                 120                 125

Arg Asp Asn Val Ser Val Asp Tyr Lys Gln Thr Gln Leu Cys Ile Ile
    130                 135                 140

Gly Cys Val Pro Ala Ile Gly Glu His Trp Gly Lys Gly Lys Ala Cys
145                 150                 155                 160

Lys Pro Asn Asn Val Ser Thr Gly Asp Cys Pro Pro Leu Glu Leu Val
                165                 170                 175

Asn Thr Pro Ile Glu Asp Gly Asp Met Ile Asp Thr Gly Tyr Gly Ala
            180                 185                 190

Met Asp Phe Gly Ala Leu Gln Glu Thr Lys Ser Glu Val Pro Leu Asp
    195                 200                 205

Ile Cys Gln Ser Ile Cys Lys Tyr Pro Asp Tyr Leu Gln Met Ser Ala
210                 215                 220

Asp Val Tyr Gly Asp Ser Met Phe Phe Cys Leu Arg Arg Glu Gln Leu
225                 230                 235                 240

Phe Ala Arg His Phe Trp Asn Arg Gly Gly Met Val Gly Asp Thr Ile
                245                 250                 255

Pro Thr Asp Met Tyr Ile Lys Gly Thr Asp Ile Arg Glu Thr Pro Ser
            260                 265                 270

Ser Tyr Val Tyr Cys Pro Ser Pro Ser Gly Ser Met Val Thr Ser Asp
    275                 280                 285

Ser Gln Leu Phe Asn Lys Pro Tyr Trp Leu His Lys Ala Gln Gly His
    290                 295                 300

Asn Asn Gly Ile Cys Trp His Asn Gln Leu Phe Leu Thr Val Val Asp
305                 310                 315                 320

Thr Thr Arg Ser Thr Asn Phe Thr Leu Ser Thr Ser Ile Glu Ser Ser
                325                 330                 335

Ile Pro Ser Thr Tyr Asp Pro Ser Lys Phe Lys Glu Tyr Thr Arg His
            340                 345                 350

Val Glu Glu Tyr Asp Leu Gln Phe Ile Phe Gln Leu Cys Thr Val Thr
            355                 360                 365

Leu Thr Thr Asp Val Met Ser Tyr Ile His Thr Met Asn Ser Ser Ile
    370                 375                 380

Leu Asp Asn Trp Asn Phe Ala Val Ala Pro Pro Pro Ser Ala Ser Leu
385                 390                 395                 400

Val Asp Thr Tyr Arg Tyr Leu Gln Ser Ala Ala Ile Thr Cys Gln Lys
                405                 410                 415
```

```
Asp Ala Pro Ala Pro Glu Lys Lys Asp Pro Tyr Asp Gly Leu Lys Phe
            420                 425                 430

Trp Asn Val Asp Leu Arg Glu Lys Phe Ser Leu Glu Leu Asp Gln Phe
            435                 440                 445

Pro Leu Gly Arg Lys Phe Leu Leu Gln Ala Arg Val Arg Arg Arg Pro
            450                 455                 460

Thr Ile Gly Pro Arg Lys Arg Pro Ala Ala Ser Thr Ser Ser Ser Ser
465                 470                 475                 480

Ala Thr Lys His Lys Arg Lys Arg Val Ser Lys
            485                 490
```

<210> SEQ ID NO 8
<211> LENGTH: 491
<212> TYPE: PRT
<213> ORGANISM: Artificial Sequence
<220> FEATURE:
<223> OTHER INFORMATION: H39N15-68T5

<400> SEQUENCE: 8

```
Met Pro Ser Val Ala Lys Val Val Asn Thr Asp Asp Tyr Val Thr Arg
1               5                   10                  15

Thr Gly Ile Tyr Tyr Ala Gly Ser Ser Arg Leu Leu Thr Val Gly
            20                  25                  30

His Pro Tyr Phe Lys Val Gly Met Asn Gly Gly Arg Lys Gln Asp Ile
            35                  40                  45

Pro Lys Val Ser Ala Tyr Gln Tyr Arg Val Phe Arg Val Thr Leu Pro
        50                  55                  60

Asp Pro Asn Lys Phe Ser Ile Pro Asp Ala Ser Leu Tyr Asn Pro Glu
65                  70                  75                  80

Thr Gln Arg Leu Val Trp Ala Cys Val Gly Val Glu Val Gly Arg Gly
            85                  90                  95

Gln Pro Leu Gly Val Gly Ile Ser Gly His Pro Leu Tyr Asn Arg Gln
            100                 105                 110

Asp Asp Thr Glu Asn Ser Pro Phe Ser Ser Thr Thr Asn Lys Asp Ser
            115                 120                 125

Arg Asp Asn Val Ser Val Asp Tyr Lys Gln Thr Gln Leu Cys Ile Ile
130                 135                 140

Gly Cys Val Pro Ala Ile Gly Glu His Trp Gly Lys Gly Lys Ala Cys
145                 150                 155                 160

Lys Pro Asn Asn Val Ser Thr Gly Asp Cys Pro Pro Leu Glu Leu Val
            165                 170                 175

Asn Thr Pro Ile Glu Asp Gly Asp Met Ile Asp Thr Gly Tyr Gly Ala
            180                 185                 190

Met Asp Phe Gly Ala Leu Gln Glu Thr Lys Ser Glu Val Pro Leu Asp
            195                 200                 205

Ile Cys Gln Ser Ile Cys Lys Tyr Pro Asp Tyr Leu Gln Met Ser Ala
            210                 215                 220

Asp Val Tyr Gly Asp Ser Met Phe Phe Cys Leu Arg Arg Glu Gln Leu
225                 230                 235                 240

Phe Ala Arg His Phe Trp Asn Arg Gly Gly Met Val Gly Asp Ala Ile
            245                 250                 255

Pro Ala Gln Leu Tyr Ile Lys Gly Thr Asp Ile Arg Ala Asn Pro Gly
            260                 265                 270

Ser Ser Val Tyr Cys Pro Ser Pro Ser Gly Ser Met Val Thr Ser Asp
            275                 280                 285
```

```
Ser Gln Leu Phe Asn Lys Pro Tyr Trp Leu His Lys Ala Gln Gly His
    290                 295                 300
Asn Asn Gly Ile Cys Trp His Asn Gln Leu Phe Leu Thr Val Val Asp
305                 310                 315                 320
Thr Thr Arg Ser Thr Asn Phe Thr Leu Ser Thr Ser Thr Asp Ser Thr
                325                 330                 335
Val Pro Ala Val Tyr Asp Ser Asn Lys Phe Lys Glu Tyr Thr Arg His
                340                 345                 350
Val Glu Glu Tyr Asp Leu Gln Phe Ile Phe Gln Leu Cys Thr Val Thr
            355                 360                 365
Leu Thr Thr Asp Val Met Ser Tyr Ile His Thr Met Asn Ser Ser Ile
    370                 375                 380
Leu Asp Asn Trp Asn Phe Ala Val Ala Pro Pro Ser Ala Ser Leu
385                 390                 395                 400
Val Asp Thr Tyr Arg Tyr Leu Gln Ser Ala Ala Ile Thr Cys Gln Lys
                405                 410                 415
Asp Ala Pro Ala Pro Glu Lys Lys Asp Pro Tyr Asp Gly Leu Lys Phe
                420                 425                 430
Trp Asn Val Asp Leu Arg Glu Lys Phe Ser Leu Glu Leu Asp Gln Phe
            435                 440                 445
Pro Leu Gly Arg Lys Phe Leu Leu Gln Ala Arg Val Arg Arg Pro
450                 455                 460
Thr Ile Gly Pro Arg Lys Arg Pro Ala Ala Ser Thr Ser Ser Ser Ser
465                 470                 475                 480
Ala Thr Lys His Lys Arg Lys Arg Val Ser Lys
                485                 490

<210> SEQ ID NO 9
<211> LENGTH: 491
<212> TYPE: PRT
<213> ORGANISM: Artificial Sequence
<220> FEATURE:
<223> OTHER INFORMATION: H39N15-68T4-70S1

<400> SEQUENCE: 9

Met Pro Ser Val Ala Lys Val Val Asn Thr Asp Asp Tyr Val Thr Arg
1               5                   10                  15
Thr Gly Ile Tyr Tyr Ala Gly Ser Ser Arg Leu Leu Thr Val Gly
            20                  25                  30
His Pro Tyr Phe Lys Val Pro Val Asn Gly Gly Arg Lys Gln Glu Ile
                35                  40                  45
Pro Lys Val Ser Ala Tyr Gln Tyr Arg Val Phe Arg Val Thr Leu Pro
    50                  55                  60
Asp Pro Asn Lys Phe Ser Ile Pro Asp Ala Ser Leu Tyr Asn Pro Glu
65                  70                  75                  80
Thr Gln Arg Leu Val Trp Ala Cys Val Gly Val Glu Val Gly Arg Gly
                85                  90                  95
Gln Pro Leu Gly Val Gly Ile Ser Gly His Pro Leu Tyr Asn Arg Gln
            100                 105                 110
Asp Asp Thr Glu Asn Ser Pro Phe Ser Ser Thr Thr Asn Lys Asp Ser
        115                 120                 125
Arg Asp Asn Val Ser Val Asp Tyr Lys Gln Thr Gln Leu Cys Ile Ile
    130                 135                 140
Gly Cys Val Pro Ala Ile Gly Glu His Trp Gly Lys Gly Lys Ala Cys
145                 150                 155                 160
```

Lys Pro Asn Asn Val Ser Thr Gly Asp Cys Pro Pro Leu Glu Leu Val
            165                 170                 175

Asn Thr Pro Ile Glu Asp Gly Asp Met Ile Asp Thr Gly Tyr Gly Ala
        180                 185                 190

Met Asp Phe Gly Ala Leu Gln Glu Thr Lys Ser Glu Val Pro Leu Asp
        195                 200                 205

Ile Cys Gln Ser Ile Cys Lys Tyr Pro Asp Tyr Leu Gln Met Ser Ala
        210                 215                 220

Asp Val Tyr Gly Asp Ser Met Phe Phe Cys Leu Arg Arg Glu Gln Leu
225                 230                 235                 240

Phe Ala Arg His Phe Trp Asn Arg Gly Gly Met Val Gly Asp Thr Ile
                245                 250                 255

Pro Thr Asp Met Tyr Ile Lys Gly Thr Asp Ile Arg Glu Thr Pro Ser
            260                 265                 270

Ser Tyr Val Tyr Cys Pro Ser Pro Gly Ser Met Val Thr Ser Asp
        275                 280                 285

Ser Gln Leu Phe Asn Lys Pro Tyr Trp Leu His Lys Ala Gln Gly His
        290                 295                 300

Asn Asn Gly Ile Cys Trp His Asn Gln Leu Phe Leu Thr Val Val Asp
305                 310                 315                 320

Thr Thr Arg Ser Thr Asn Phe Thr Leu Ser Thr Ser Ile Glu Ser Ser
                325                 330                 335

Ile Pro Ser Thr Tyr Asp Pro Ser Lys Phe Lys Glu Tyr Thr Arg His
            340                 345                 350

Val Glu Glu Tyr Asp Leu Gln Phe Ile Phe Gln Leu Cys Thr Val Thr
        355                 360                 365

Leu Thr Thr Asp Val Met Ser Tyr Ile His Thr Met Asn Ser Ser Ile
370                 375                 380

Leu Asp Asn Trp Asn Phe Ala Val Ala Pro Pro Ser Ala Ser Leu
385                 390                 395                 400

Val Asp Thr Tyr Arg Tyr Leu Gln Ser Ala Ala Ile Thr Cys Gln Lys
                405                 410                 415

Asp Ala Pro Ala Pro Glu Lys Lys Asp Pro Tyr Asp Gly Leu Lys Phe
            420                 425                 430

Trp Asn Val Asp Leu Arg Glu Lys Phe Ser Leu Glu Leu Asp Gln Phe
        435                 440                 445

Pro Leu Gly Arg Lys Phe Leu Leu Gln Ala Arg Val Arg Arg Pro
        450                 455                 460

Thr Ile Gly Pro Arg Lys Arg Pro Ala Ala Ser Thr Ser Ser Ser Ser
465                 470                 475                 480

Ala Thr Lys His Lys Arg Lys Arg Val Ser Lys
                485                 490

<210> SEQ ID NO 10
<211> LENGTH: 492
<212> TYPE: PRT
<213> ORGANISM: Artificial Sequence
<220> FEATURE:
<223> OTHER INFORMATION: H39N15-68T4-70S2

<400> SEQUENCE: 10

Met Pro Ser Val Ala Lys Val Val Asn Thr Asp Asp Tyr Val Thr Arg
1               5                   10                  15

Thr Gly Ile Tyr Tyr Tyr Ala Gly Ser Ser Arg Leu Leu Thr Val Gly
            20                  25                  30

His Pro Tyr Phe Lys Val Gly Met Asn Gly Gly Arg Lys Gln Asp Ile
                35                  40                  45

Pro Lys Val Ser Ala Tyr Gln Tyr Arg Val Phe Arg Val Thr Leu Pro
 50                  55                  60

Asp Pro Asn Lys Phe Ser Ile Pro Asp Ala Ser Leu Tyr Asn Pro Glu
 65                  70                  75                  80

Thr Gln Arg Leu Val Trp Ala Cys Val Gly Val Glu Val Gly Arg Gly
                 85                  90                  95

Gln Pro Leu Gly Val Gly Val Ser Gly His Pro Leu Tyr Asn Arg Leu
                100                 105                 110

Asp Asp Thr Glu Asn Ser His Phe Ser Ser Ala Val Asn Thr Gln Asp
            115                 120                 125

Ser Arg Asp Asn Val Ser Val Asp Tyr Lys Gln Thr Gln Leu Cys Ile
    130                 135                 140

Ile Gly Cys Val Pro Ala Ile Gly Glu His Trp Gly Lys Gly Lys Ala
145                 150                 155                 160

Cys Lys Pro Asn Asn Val Ser Thr Gly Asp Cys Pro Pro Leu Glu Leu
                165                 170                 175

Val Asn Thr Pro Ile Glu Asp Gly Asp Met Ile Asp Thr Gly Tyr Gly
                180                 185                 190

Ala Met Asp Phe Gly Ala Leu Gln Glu Thr Lys Ser Glu Val Pro Leu
            195                 200                 205

Asp Ile Cys Gln Ser Ile Cys Lys Tyr Pro Asp Tyr Leu Gln Met Ser
    210                 215                 220

Ala Asp Val Tyr Gly Asp Ser Met Phe Phe Cys Leu Arg Arg Glu Gln
225                 230                 235                 240

Leu Phe Ala Arg His Phe Trp Asn Arg Gly Gly Met Val Gly Asp Thr
                245                 250                 255

Ile Pro Thr Asp Met Tyr Ile Lys Gly Thr Asp Ile Arg Glu Thr Pro
                260                 265                 270

Ser Ser Tyr Val Tyr Cys Pro Ser Pro Ser Gly Ser Met Val Thr Ser
            275                 280                 285

Asp Ser Gln Leu Phe Asn Lys Pro Tyr Trp Leu His Lys Ala Gln Gly
    290                 295                 300

His Asn Asn Gly Ile Cys Trp His Asn Gln Leu Phe Leu Thr Val Val
305                 310                 315                 320

Asp Thr Thr Arg Ser Thr Asn Phe Thr Leu Ser Thr Ser Ile Glu Ser
                325                 330                 335

Ser Ile Pro Ser Thr Tyr Asp Pro Ser Lys Phe Lys Glu Tyr Thr Arg
                340                 345                 350

His Val Glu Glu Tyr Asp Leu Gln Phe Ile Phe Gln Leu Cys Thr Val
            355                 360                 365

Thr Leu Thr Thr Asp Val Met Ser Tyr Ile His Thr Met Asn Ser Ser
    370                 375                 380

Ile Leu Asp Asn Trp Asn Phe Ala Val Ala Pro Pro Ser Ala Ser
385                 390                 395                 400

Leu Val Asp Thr Tyr Arg Tyr Leu Gln Ser Ala Ala Ile Thr Cys Gln
                405                 410                 415

Lys Asp Ala Pro Ala Pro Glu Lys Lys Asp Pro Tyr Asp Gly Leu Lys
                420                 425                 430

Phe Trp Asn Val Asp Leu Arg Glu Lys Phe Ser Leu Glu Leu Asp Gln
            435                 440                 445

Phe Pro Leu Gly Arg Lys Phe Leu Leu Gln Ala Arg Val Arg Arg Arg

```
                  450                 455                 460
Pro Thr Ile Gly Pro Arg Lys Arg Pro Ala Ser Thr Ser Ser Ser
465                 470                 475                 480

Ser Ala Thr Lys His Lys Arg Lys Arg Val Ser Lys
                    485                 490

<210> SEQ ID NO 11
<211> LENGTH: 491
<212> TYPE: PRT
<213> ORGANISM: Artificial Sequence
<220> FEATURE:
<223> OTHER INFORMATION: H39N15-68T4-70S3

<400> SEQUENCE: 11

Met Pro Ser Val Ala Lys Val Val Asn Thr Asp Asp Tyr Val Thr Arg
1               5                   10                  15

Thr Gly Ile Tyr Tyr Ala Gly Ser Ser Arg Leu Leu Thr Val Gly
                20                  25                  30

His Pro Tyr Phe Lys Val Gly Met Asn Gly Gly Arg Lys Gln Asp Ile
            35                  40                  45

Pro Lys Val Ser Ala Tyr Gln Tyr Arg Val Phe Arg Val Thr Leu Pro
50                  55                  60

Asp Pro Asn Lys Phe Ser Ile Pro Asp Ala Ser Leu Tyr Asn Pro Glu
65                  70                  75                  80

Thr Gln Arg Leu Val Trp Ala Cys Val Gly Val Glu Val Gly Arg Gly
                85                  90                  95

Gln Pro Leu Gly Val Gly Ile Ser Gly His Pro Leu Tyr Asn Arg Gln
            100                 105                 110

Asp Asp Thr Glu Asn Ser Pro Phe Ser Ser Thr Asn Lys Asp Ser
115                 120                 125

Arg Asp Asn Val Ser Val Asp Tyr Lys Gln Thr Gln Leu Cys Ile Ile
130                 135                 140

Gly Cys Val Pro Ala Ile Gly Glu His Trp Ala Lys Gly Lys Ala Cys
145                 150                 155                 160

Lys Ser Thr Thr Val Gln Gln Gly Asp Cys Pro Pro Leu Glu Leu Val
                165                 170                 175

Asn Thr Pro Ile Glu Asp Gly Asp Met Ile Asp Thr Gly Tyr Gly Ala
            180                 185                 190

Met Asp Phe Gly Ala Leu Gln Glu Thr Lys Ser Glu Val Pro Leu Asp
        195                 200                 205

Ile Cys Gln Ser Ile Cys Lys Tyr Pro Asp Tyr Leu Gln Met Ser Ala
210                 215                 220

Asp Val Tyr Gly Asp Ser Met Phe Phe Cys Leu Arg Arg Glu Gln Leu
225                 230                 235                 240

Phe Ala Arg His Phe Trp Asn Arg Gly Gly Met Val Gly Asp Thr Ile
                245                 250                 255

Pro Thr Asp Met Tyr Ile Lys Gly Thr Asp Ile Arg Glu Thr Pro Ser
            260                 265                 270

Ser Tyr Val Tyr Cys Pro Ser Pro Ser Gly Ser Met Val Thr Ser Asp
        275                 280                 285

Ser Gln Leu Phe Asn Lys Pro Tyr Trp Leu His Lys Ala Gln Gly His
290                 295                 300

Asn Asn Gly Ile Cys Trp His Asn Gln Leu Phe Leu Thr Val Val Asp
305                 310                 315                 320

Thr Thr Arg Ser Thr Asn Phe Thr Leu Ser Thr Ser Ile Glu Ser Ser
```

```
                    325                 330                 335
Ile Pro Ser Thr Tyr Asp Pro Ser Lys Phe Lys Glu Tyr Thr Arg His
                340                 345                 350

Val Glu Glu Tyr Asp Leu Gln Phe Ile Phe Gln Leu Cys Thr Val Thr
                355                 360                 365

Leu Thr Thr Asp Val Met Ser Tyr Ile His Thr Met Asn Ser Ser Ile
        370                 375                 380

Leu Asp Asn Trp Asn Phe Ala Val Ala Pro Pro Ser Ala Ser Leu
385                 390                 395                 400

Val Asp Thr Tyr Arg Tyr Leu Gln Ser Ala Ala Ile Thr Cys Gln Lys
                405                 410                 415

Asp Ala Pro Ala Pro Glu Lys Lys Asp Pro Tyr Asp Gly Leu Lys Phe
                420                 425                 430

Trp Asn Val Asp Leu Arg Glu Lys Phe Ser Leu Glu Leu Asp Gln Phe
                435                 440                 445

Pro Leu Gly Arg Lys Phe Leu Leu Gln Ala Arg Val Arg Arg Arg Pro
                450                 455                 460

Thr Ile Gly Pro Arg Lys Arg Pro Ala Ala Ser Thr Ser Ser Ser Ser
465                 470                 475                 480

Ala Thr Lys His Lys Arg Lys Arg Val Ser Lys
                485                 490

<210> SEQ ID NO 12
<211> LENGTH: 491
<212> TYPE: PRT
<213> ORGANISM: Artificial Sequence
<220> FEATURE:
<223> OTHER INFORMATION: H39N15-68T4-70S5

<400> SEQUENCE: 12

Met Pro Ser Val Ala Lys Val Val Asn Thr Asp Asp Tyr Val Thr Arg
1               5                   10                  15

Thr Gly Ile Tyr Tyr Ala Gly Ser Ser Arg Leu Leu Thr Val Gly
                20                  25                  30

His Pro Tyr Phe Lys Val Gly Met Asn Gly Gly Arg Lys Gln Asp Ile
                35                  40                  45

Pro Lys Val Ser Ala Tyr Gln Tyr Arg Val Phe Arg Val Thr Leu Pro
            50                  55                  60

Asp Pro Asn Lys Phe Ser Ile Pro Asp Ala Ser Leu Tyr Asn Pro Glu
65                  70                  75                  80

Thr Gln Arg Leu Val Trp Ala Cys Val Gly Val Glu Val Gly Arg Gly
                85                  90                  95

Gln Pro Leu Gly Val Gly Ile Ser Gly His Pro Leu Tyr Asn Arg Gln
                100                 105                 110

Asp Asp Thr Glu Asn Ser Pro Phe Ser Ser Thr Asn Lys Asp Ser
            115                 120                 125

Arg Asp Asn Val Ser Val Asp Tyr Lys Gln Thr Gln Leu Cys Ile Ile
        130                 135                 140

Gly Cys Val Pro Ala Ile Gly Glu His Trp Gly Lys Gly Lys Ala Cys
145                 150                 155                 160

Lys Pro Asn Asn Val Ser Thr Gly Asp Cys Pro Pro Leu Glu Leu Val
                165                 170                 175

Asn Thr Pro Ile Glu Asp Gly Asp Met Ile Asp Thr Gly Tyr Gly Ala
                180                 185                 190

Met Asp Phe Gly Ala Leu Gln Glu Thr Lys Ser Glu Val Pro Leu Asp
```

```
            195                 200                 205
Ile Cys Gln Ser Ile Cys Lys Tyr Pro Asp Tyr Leu Gln Met Ser Ala
    210                 215                 220

Asp Val Tyr Gly Asp Ser Met Phe Phe Cys Leu Arg Arg Glu Gln Leu
225                 230                 235                 240

Phe Ala Arg His Phe Trp Asn Arg Gly Gly Met Val Gly Asp Thr Ile
                245                 250                 255

Pro Thr Asp Met Tyr Ile Lys Gly Thr Asp Ile Arg Glu Thr Pro Ser
            260                 265                 270

Ser Tyr Val Tyr Cys Pro Ser Pro Ser Gly Ser Met Val Thr Ser Asp
        275                 280                 285

Ser Gln Leu Phe Asn Lys Pro Tyr Trp Leu His Lys Ala Gln Gly His
    290                 295                 300

Asn Asn Gly Ile Cys Trp His Asn Gln Leu Phe Leu Thr Val Val Asp
305                 310                 315                 320

Thr Thr Arg Ser Thr Asn Phe Thr Leu Ser Thr Ser Thr Glu Thr Ala
                325                 330                 335

Ile Pro Ala Val Tyr Ser Pro Thr Lys Phe Lys Glu Tyr Thr Arg His
            340                 345                 350

Val Glu Glu Tyr Asp Leu Gln Phe Ile Phe Gln Leu Cys Thr Val Thr
        355                 360                 365

Leu Thr Thr Asp Val Met Ser Tyr Ile His Thr Met Asn Ser Ser Ile
    370                 375                 380

Leu Asp Asn Trp Asn Phe Ala Val Ala Pro Pro Ser Ala Ser Leu
385                 390                 395                 400

Val Asp Thr Tyr Arg Tyr Leu Gln Ser Ala Ala Ile Thr Cys Gln Lys
                405                 410                 415

Asp Ala Pro Ala Pro Glu Lys Lys Asp Pro Tyr Asp Gly Leu Lys Phe
            420                 425                 430

Trp Asn Val Asp Leu Arg Glu Lys Phe Ser Leu Glu Leu Asp Gln Phe
        435                 440                 445

Pro Leu Gly Arg Lys Phe Leu Leu Gln Ala Arg Val Arg Arg Arg Pro
    450                 455                 460

Thr Ile Gly Pro Arg Lys Arg Pro Ala Ala Ser Thr Ser Ser Ser Ser
465                 470                 475                 480

Ala Thr Lys His Lys Arg Lys Arg Val Ser Lys
                485                 490

<210> SEQ ID NO 13
<211> LENGTH: 1518
<212> TYPE: DNA
<213> ORGANISM: Human papillomavirus type 39

<400> SEQUENCE: 13
atggccctct ggcgcagctc cgattccatg gtctacctcc cccccccag cgtcgccaag      60 gtcgtgaaca ccgacgacta cgtcacccgc accgggatct actactacgc cgggtccagc     120
cgcctgctga ccgtgggcca ccctacttc aaggtcggca tgaacggcgg cgcaagcag      180 gatatcccca aggtcagcgc ctaccagtac cgcgtgttcc gcgtcaccct cccagacccc     240
aacaagttct ccatccccga cgccagcctg tacaacccg agacccagcg cctggtgtgg     300
gcctgcgtgg gcgtcgaagt cgggcgcggg cagcccctcg cgtcggcat ctccggccac     360 cccctgtaca accgcagga cgacaccgag aatagcccct tcagcagcac aacaaacaag     420
gattcccgcg acaacgtcag cgtcgactac aagcagaccc agctctgtat catcgggtgc     480
```

-continued

```
gtcccagcaa tcggcgaaca ctggggcaag ggcaaggcct gtaagccaaa caacgtgagc      540
accggcgatt gccccccct ggagctggtg aatacaccca tcgaagacgg cgacatgatc       600
gacaccgggt acggcgccat ggatttcggc gccctccagg agacaaagtc cgaagtcccc      660
ctggacatct gccagagcat ctgcaagtac cccgactacc tccagatgag cgccgacgtc     720
tacggcgatt ccatgttctt ctgcctgcgc cgcgagcagc tcttcgcccg ccacttctgg      780
aaccgcggcg catggtcgg cgatgcaatc cccgcacagc tctacatcaa ggggaccgac       840
atccgcgcca atccaggctc cagcgtgtat tgtccaagcc catccggcag catggtgaca      900
agcgacagcc agctgttcaa caagccctac tggctgcaca aggcacaggg cataataac       960 ggcatctgct ggcacaacca gctgttcctg accgtcgtcg ataccacacg ctccacaaat     1020
ttcaccctga gcacaagcat cgaaagcagc atccccagca cctacgaccc cagcaagttc     1080
aaggagtaca cacgccacgt cgaagaatac gacctgcagt tcatcttcca gctctgcacc     1140
gtgaccctga ccaccgacgt catgagctac atccacacca tgaacagcag catcctcgat     1200
aactggaact tcgccgtggc ccccccccc agcgcatccc tcgtggatac ctatcgctat     1260
ctgcagagcg ccgcaatcac ctgccagaag gacgccccg cccccgagaa gaaggaccc     1320 tacgatggcc tgaagttctg gaacgtcgat ctgcgcgaga gttctcccct ggagctggac     1380
cagttccccc tcggccgcaa gttcctcctc caggcacgcg tgcgccgccg ccccaccatc      1440
ggcccacgca agcgccccgc cgccagcacc agcagcagca gcgccaccaa gcacaagcgc     1500
aagcgcgtca gcaagtga                                                  1518
```

<210> SEQ ID NO 14
<211> LENGTH: 1518
<212> TYPE: DNA
<213> ORGANISM: Human papillomavirus type 68

<400> SEQUENCE: 14

```
atggcactgt ggagagccag cgacaacatg gtgtacctgc cccctcccag cgtggccaag       60
gtggtcaaca ccgacgacta cgtgacccgg accggcatgt actactacgc cggcaccctct      120 cggctcctga ccgtgggcca cccctacttc aaggtgccca tgagcggcgg cagaaagcag       180
ggcatcccca ggtgtccgc ctaccagtac cgggtgttca gagtgaccct gcccgacccc       240
aacaagttca gcgtgcccga gagcaccctg tacaaccccg acacccagcg gatggtctgg      300
gcctgcgtgg gcgtggagat cggcagaggc cagcccctgg gcgtgggcct gagcggccac      360
cccctgtaca atcggctgga cgacaccgag aacagcccct tcagcagcaa caagaacccc      420
aaggacagcc gggacaacgt ggccgtggac tgcaagcaga cccagctgtg catcatcggc      480
tgcgtgcctg ccattggcga gcactgggcc aagggcaaga gctgcaagcc caccaacgtg      540
cagcagggcg actgccccc tctggaactg gtcaacacac ccatcgagga cggcgacatg      600
atcgacaccg gctacggcgc catggacttc ggcaccctgc aggaaaccaa gagcgaggtc      660
cccctggaca tctgccagag cgtgtgcaag taccccgact acctgcagat gagcgccgac      720
gtgtacggcg acagcatgtt cttttgcctg cggcgggagc agctgttcgc ccggcacttc      780
tggaacagag gcgcatggt cggcgacacc atccccaccg acatgtacat caagggcacc      840
gacatcagag agacacccag cagctacgtg tacgccccca gccccagcgg cagcatggtg      900
tccagcgaca gccagctgtt caacaagccc tactggctgc acaaggccca gggcacaac      960 aacggcatct gctggcacaa ccagctgttt ctgaccgtgg tggacaccac cagaagcacc     1020
```

```
aacttcacccc tgagcaccac caccgacagc accgtgcccg ccgtgtacga cagcaataag    1080
ttcaaagaat acgtgcggca cgtggaggaa tacgacctgc agttcatctt ccagctgtgt    1140
accatcaccc tgtccaccga cgtgatgagc tacatccaca ccatgaaccc cgccatcctg    1200
gacgactgga acttcggcgt ggcccctccc cctagcgcca gctggtgga tacctacaga    1260 tacctgcaga gcgccgccat cacctgccag aaggacgccc ctgcccccgt gaagaaggac    1320
ccctacgacg cctgaacttc ctggaatgtg gacctgaaag agaagttcag cagcgagctg    1380
gaccagttcc ccctgggccg gaagttcctg ctgcaagccg gcgtgcggag aaggcccacc    1440
atcggcccca gaaagcggac cgccaccgca gccacaacct ccacctccaa gcacaagcgg    1500
aagcgggtgt ccaagtga                                                  1518
```

<210> SEQ ID NO 15
<211> LENGTH: 1521
<212> TYPE: DNA
<213> ORGANISM: Human papillomavirus type 70

<400> SEQUENCE: 15

```
atggctttgt ggcggtctag tgacaacacg gtgtatttgc accccccttc tgtggcgaag     60
gttgtcaata cagatgatta tgtaacacgt acaggcatat attattatgc tggaagctct    120
cgcttattaa cagtagggca tccttatttt aaggtacctg taaatggtgg ccgcaagcag    180
gaaataccta aggtgtctgc atatcagtat agggtattta gggtatccct acctgatcct    240
aataagtttg ccttccggga tccttccctt tataatcctg acacacaacg cctggtatgg    300
gcctgtatag gtgtggaaat tggtagaggc cagccattgg gcgttggtgt tagtggacat    360 ccttttatata atagattgga tgatactgaa aattcacatt tttcctctgc tgttaataca    420
caggacagta gggacaatgt gtctgtggac tataagcaga cacagttatg tattataggc    480
tgtgttcctg ctatgggaga gcactgggca aagggcaagg cctgtaagtc cactactgta    540
caacagggcg attgtccacc attagaatta gttaatactg caattgagga tggcgatatg    600
atagatacag gctatggagc catggacttt cgtacattgc aggaaaccaa agtgaggta    660 ccactagata tttgccaatc cgtgtgtaaa tatcctgatt atttgcagat gtctgctgat    720
gtatatgggg acagtatgtt ttttgtttg cgcaaggaac agttatttgc cagacacttt    780
tggaatagag gtggcatggt gggcgacaca atacccttcag agttatatat taaaggcacg    840
gatatacgtg atcgtcctgg tactcatgta tattcccctt ccccaagtgg ctctatggtt    900
tcttctgatt cccagttgtt taataagccc tattggttgc ataaggccca gggacacaat    960
aatggcattt gttggcataa ccagttgttt attactgtgg tggacactac acgtagtact   1020
aattttacat tgtctgcctg caccgaaaca gccatacctg ctgtatatag ccctacaaag   1080
tttaaggaat atactaggca tgtggaggaa tatgatttac aatttatatt tcagttgtgt   1140
actatcacat taactgcaga cgttatggcc tacatccata ctatgaatcc tgcaattttg   1200
gacaattgga atataggcgt taccccctcca ccatctgcaa gcttggtgga cacgtatagg   1260
tatttacaat cagcagctat agcatgtcag aaggatgctc ctgcacctga aaaaaaggat   1320
ccctatgacg atttaaaaatt ttggaatgtt gatttaaagg aaaagtttag tacagaacta   1380
gatcagtttc ctttggggcg caaattttta ctacaggtag gggctcgcag acgtcctact   1440
ataggccctc gcaaacgccc tgcatcagct aaatcgtctt cctcagcctc taaacacaaa   1500
cggaaacgtg tgtccaagta a                                             1521
```

<210> SEQ ID NO 16
<211> LENGTH: 1476
<212> TYPE: DNA
<213> ORGANISM: Artificial Sequence
<220> FEATURE:
<223> OTHER INFORMATION: The DNA sequence encoding H39N15-68T1

<400> SEQUENCE: 16

| | |
|---|---|
| atgcccagcg tcgccaaggt cgtgaacacc gacgactacg tcacccgcac cgggatctac | 60 |
| tactacgccg gtccagccg cctgctgacc gtgggccacc cctacttcaa ggtgcccatg | 120 |
| agcggcggca gaaagcaggg catccccaag gtgtccgcct accagtaccg cgtgttccgc | 180 |
| gtcaccctcc cagaccccaa caagttctcc atccccgacg ccagcctgta caaccccgag | 240 |
| acccagcgcc tggtgtgggc ctgcgtgggc gtcgaagtcg ggcgcgggca gcccctcggc | 300 |
| gtcggcatct ccggccaccc cctgtacaac cgccaggacg acaccgagaa tagccccttc | 360 |
| agcagcacaa caaacaagga ttcccgcgac aacgtcagcg tcgactacaa gcagacccag | 420 |
| ctctgtatca tcgggtgcgt cccagcaatc ggcgaacact ggggcaaggg caaggcctgt | 480 |
| aagccaaaca acgtgagcac cggcgattgc ccccccctgg agctggtgaa tacacccatc | 540 |
| gaagacggcg acatgatcga caccgggtac ggcgccatgg atttcggcgc cctccaggag | 600 |
| acaaagtccg aagtcccccct ggacatctgc cagagcatct gcaagtaccc cgactacctc | 660 |
| cagatgagcg ccgacgtcta cggcgattcc atgttcttct gcctgcgccg cgagcagctc | 720 |
| ttcgcccgcc acttctggaa ccgcggcggc atggtcggcg atgcaatccc cgcacagctc | 780 |
| tacatcaagg ggaccgacat ccgcgccaat ccaggctcca gcgtgtattg tccaagccca | 840 |
| tccggcagca tggtgacaag cgacagccag ctgttcaaca gcccctactg gctgcacaag | 900 |
| gcacaggggc ataataacgg catctgctgg cacaaccagc tgttcctgac cgtcgtcgat | 960 |
| accacacgct ccacaaattt cacccctgagc acaagcatcg aaagcagcat ccccagcacc | 1020 |
| tacgacccca gcaagttcaa ggagtacaca cgccacgtcg aagaatacga cctgcagttc | 1080 |
| atcttccagc tctgcaccgt gaccctgacc accgacgtca tgagctacat ccacaccatg | 1140 |
| aacagcagca cctcgataa ctggaacttc gccgtggccc ccccccccag cgcatccctc | 1200 |
| gtggatacct atcgctatct gcagagcgcc gcaatcacct gccagaagga cgcccccgcc | 1260 |
| cccgagaaga aggaccccta cgatggcctg aagttctgga acgtcgatct gcgcgagaag | 1320 |
| ttctcccctgg agctggacca gttcccccctc ggccgcaagt cctcctcca ggcacgcgtg | 1380 |
| cgccgccgcc ccaccatcgg cccacgcaag cgccccgccg ccagcaccag cagcagcagc | 1440 |
| gccaccaagc acaagcgcaa gcgcgtcagc aagtga | 1476 |

<210> SEQ ID NO 17
<211> LENGTH: 1479
<212> TYPE: DNA
<213> ORGANISM: Artificial Sequence
<220> FEATURE:
<223> OTHER INFORMATION: The DNA sequence encoding H39N15-68T2

<400> SEQUENCE: 17

| | |
|---|---|
| atgcccagcg tcgccaaggt cgtgaacacc gacgactacg tcacccgcac cgggatctac | 60 |
| tactacgccg gtccagccg cctgctgacc gtgggccacc cctacttcaa ggtcggcatg | 120 |
| aacggcgggc gcaagcagga tatccccaag gtcagcgcct accagtaccg cgtgttccgc | 180 |
| gtcaccctcc cagaccccaa caagttctcc atccccgacg ccagcctgta caaccccgag | 240 |
| acccagcgcc tggtgtgggc ctgcgtgggc gtcgaagtcg gcagaggcca gcccctgggc | 300 |

| | |
|---|---|
| gtgggcctga gcggccaccc cctgtacaat cggctggacg acaccgagaa cagccccttc | 360 |
| agcagcaaca agaaccccaa ggacagccgg gacaacgtgg ccgtggactg caagcagacc | 420 |
| cagctctgta tcatcgggtg cgtcccagca atcggcgaac actggggcaa gggcaaggcc | 480 |
| tgtaagccaa acaacgtgag caccggcgat tgccccccc tggagctggt gaatacaccc | 540 |
| atcgaagacg gcgacatgat cgacaccggg tacggcgcca tggatttcgg cgccctccag | 600 |
| gagacaaagt ccgaagtccc cctggacatc tgccagagca tctgcaagta ccccgactac | 660 |
| ctccagatga gcgccgacgt ctacggcgat tccatgttct tctgcctgcg ccgcgagcag | 720 |
| ctcttcgccc gccacttctg gaaccgcggc ggcatggtcg gcgatgcaat ccccgcacag | 780 |
| ctctacatca aggggaccga catccgcgcc aatccaggct ccagcgtgta ttgtccaagc | 840 |
| ccatccggca gcatggtgac aagcgacagc cagctgttca acaagcccta ctggctgcac | 900 |
| aaggcacagg gcataataa cggcatctgc tggcacaacc agctgttcct gaccgtcgtc | 960 |
| gataccacac gctccacaaa tttcacccctg agcacaagca tcgaaagcag catccccagc | 1020 |
| acctacgacc ccagcaagtt caaggagtac acacgccacg tcgaagaata cgacctgcag | 1080 |
| ttcatcttcc agctctgcac cgtgaccctg accaccgacg tcatgagcta catccacacc | 1140 |
| atgaacagca gcatcctcga taactggaac ttcgccgtgg ccccccccc cagcgcatcc | 1200 |
| ctcgtggata cctatcgcta tctgcagagc gccgcaatca cctgccagaa ggacgccccc | 1260 |
| gcccccgaga agaaggaccc ctacgatggc ctgaagttct ggaacgtcga tctgcgcgag | 1320 |
| aagttctccc tggagctgga ccagttcccc ctcggccgca agttcctcct ccaggcacgc | 1380 |
| gtgcgccgcc gccccaccat cggcccacgc aagcgccccg ccgccagcac cagcagcagc | 1440 |
| agcgccacca agcacaagcg caagcgcgtc agcaagtga | 1479 |

<210> SEQ ID NO 18
<211> LENGTH: 1476
<212> TYPE: DNA
<213> ORGANISM: Artificial Sequence
<220> FEATURE:
<223> OTHER INFORMATION: The DNA sequence encoding H39N15-68T3

<400> SEQUENCE: 18

| | |
|---|---|
| atgcccagcg tcgccaaggt cgtgaacacc gacgactacg tcacccgcac cgggatctac | 60 |
| tactacgccg gtccagccg cctgctgacc gtgggccacc cctacttcaa ggtcggcatg | 120 |
| aacggcgggc gcaagcagga tatccccaag gtcagcgcct accagtaccg cgtgttccgc | 180 |
| gtcaccctcc cagaccccaa caagttctcc atccccgacg ccagcctgta caaccccgag | 240 |
| acccagcgcc tggtgtgggc ctgcgtgggc gtcgaagtcg ggcgcgggca gccccctcggc | 300 |
| gtcggcatct ccggccaccc cctgtacaac cgccaggacg acaccgagaa tagcccccttc | 360 |
| agcagcacaa caaacaagga ttcccgcgac aacgtcagcg tcgactacaa gcagacccag | 420 |
| ctctgtatca tcgggtgcgt cccagcaatc ggcgaacact gggccaaggg caagagctgc | 480 |
| aagcccacca acgtgcagca gggcgactgc ccccctctgg agctggtgaa tacacccatc | 540 |
| gaagacggcg acatgatcga caccgggtac ggcgccatgg atttcggcgc cctccaggag | 600 |
| acaaagtccg aagtcccccct ggacatctgc cagagcatct gcaagtaccc cgactacctc | 660 |
| cagatgagcg ccgacgtcta cggcgattcc atgttcttct gcctgcgccg cgagcagctc | 720 |
| ttcgcccgcc acttctggaa ccgcggcggc atggtcggcg atgcaatccc cgcacagctc | 780 |
| tacatcaagg ggaccgacat ccgcgccaat ccaggctcca gcgtgtattg tccaagccca | 840 |
| tccggcagca tggtgacaag cgacagccag ctgttcaaca agccctactg gctgcacaag | 900 |

```
gcacaggggc ataataacgg catctgctgg cacaaccagc tgttcctgac cgtcgtcgat      960
accacacgct ccacaaattt caccctgagc acaagcatcg aaagcagcat ccccagcacc     1020
tacgacccca gcaagttcaa ggagtacaca cgccacgtcg aagaatacga cctgcagttc     1080
atcttccagc tctgcaccgt gaccctgacc accgacgtca tgagctacat ccacaccatg     1140
aacagcagca tcctcgataa ctggaacttc gccgtggccc cccccccag cgcatccctc      1200 gtggatacct atcgctatct gcagagcgcc gcaatcacct gccagaagga cgcccccgcc     1260
cccgagaaga aggacccta cgatggcctg aagttctgga acgtcgatct gcgcgagaag     1320
ttctccctgg agctggacca gttccccctc ggccgcaagt tcctcctcca ggcacgcgtg     1380
cgccgccgcc ccaccatcgg cccacgcaag cgccccgccg ccagcaccag cagcagcagc     1440
gccaccaagc acaagcgcaa gcgcgtcagc aagtga                              1476
```

<210> SEQ ID NO 19
<211> LENGTH: 1476
<212> TYPE: DNA
<213> ORGANISM: Artificial Sequence
<220> FEATURE:
<223> OTHER INFORMATION: The DNA sequence encoding H39N15-68T4

<400> SEQUENCE: 19

```
atgcccagcg tcgccaaggt cgtgaacacc gacgactacg tcacccgcac cgggatctac       60
tactacgccg gtccagccg cctgctgacc gtgggccacc cctacttcaa ggtcggcatg      120
aacggcgggc gcaagcagga tatccccaag gtcagcgcct accagtaccg cgtgttccgc      180
gtcaccctcc cagaccccaa caagttctcc atccccgacg ccagcctgta caaccccgag      240
acccagcgcc tggtgtgggc ctgcgtgggc gtcgaagtcg ggcgcgggca gccccctcggc      300 gtcggcatct ccggccaccc cctgtacaac cgccaggacg acaccgagaa tagcccct tc      360 agcagcacaa caaacaagga ttcccgcgac aacgtcagcg tcgactacaa gcagacccag      420
ctctgtatca tcgggtgcgt cccagcaatc ggcgaacact ggggcaaggg caaggcctgt      480
aagccaaaca cgtgagcac cggcgattgc ccccccctgg agctggtgaa tacacccatc      540
gaagacggcg acatgatcga caccgggtac ggcgccatgg atttcggcgc cctccaggag      600
acaaagtccg aagtccccct ggacatctgc cagagcatct gcaagtaccc cgactacctc      660
cagatgagcg ccgacgtcta cggcgattcc atgttcttct gcctgcgccg cgagcagctc      720
ttcgcccgcc acttctggaa cagaggcggc atggtcggcg acaccatccc caccgacatg      780
tacatcaagg gcaccgacat cagagagaca cccagcagct acgtgtactg tccaagccca      840
tccggcagca tggtgacaag cgacagccag ctgttcaaca gccctactg gctgcacaag      900 gcacaggggc ataataacgg catctgctgg cacaaccagc tgttcctgac cgtcgtcgat      960
accacacgct ccacaaattt caccctgagc acaagcatcg aaagcagcat ccccagcacc     1020
tacgacccca gcaagttcaa ggagtacaca cgccacgtcg aagaatacga cctgcagttc     1080
atcttccagc tctgcaccgt gaccctgacc accgacgtca tgagctacat ccacaccatg     1140
aacagcagca tcctcgataa ctggaacttc gccgtggccc cccccccag cgcatccctc      1200 gtggatacct atcgctatct gcagagcgcc gcaatcacct gccagaagga cgcccccgcc     1260
cccgagaaga aggacccta cgatggcctg aagttctgga acgtcgatct gcgcgagaag     1320
ttctccctgg agctggacca gttccccctc ggccgcaagt tcctcctcca ggcacgcgtg     1380
cgccgccgcc ccaccatcgg cccacgcaag cgccccgccg ccagcaccag cagcagcagc     1440
```

```
gccaccaagc acaagcgcaa gcgcgtcagc aagtga                              1476
```

<210> SEQ ID NO 20
<211> LENGTH: 1476
<212> TYPE: DNA
<213> ORGANISM: Artificial Sequence
<220> FEATURE:
<223> OTHER INFORMATION: The DNA sequence encoding H39N15-68T5

<400> SEQUENCE: 20

```
atgcccagcg tcgccaaggt cgtgaacacc gacgactacg tcacccgcac cgggatctac     60
tactacgccg gtccagccg cctgctgacc gtgggccacc cctacttcaa ggtcggcatg     120
aacggcgggc gcaagcagga tatccccaag gtcagcgcct accagtaccg cgtgttccgc    180
gtcaccctcc cagaccccaa caagttctcc atccccgacg ccagcctgta caaccccgag    240
acccagcgcc tggtgtgggc ctgcgtgggc gtcgaagtcg ggcgcgggca gcccctcggc    300
gtcggcatct ccggccaccc cctgtacaac cgcaggacg acaccgagaa tagccccttc    360
agcagcacaa caaacaagga ttcccgcgac aacgtcagct cgactacaa gcagacccag    420
ctctgtatca tcgggtgcgt cccagcaatc ggcgaacact ggggcaaggg caaggcctgt    480
aagccaaaca cgtgagcac cggcgattgc ccccccctgg agctggtgaa tacacccatc    540
gaagacggcg acatgatcga caccgggtac ggcgccatgg atttcggcgc cctccaggag    600
acaaagtccg aagtccccct ggacatctgc cagagcatct gcaagtaccc cgactacctc    660
cagatgagcg ccgacgtcta cggcgattcc atgttcttct gcctgcgccg cgagcagctc    720
ttcgcccgcc acttctggaa ccgcggcggc atggtcggcg atgcaatccc cgcacagctc    780
tacatcaagg ggaccgacat ccgcgccaat ccaggctcca gcgtgtattg tccaagccca    840
tccggcagca tggtgacaag cgacagccag ctgttcaaca gcccctactg gctgcacaag    900
gcacaggggc ataataacgg catctgctgg cacaaccagc tgttcctgac cgtcgtcgat    960
accacacgct ccacaaattt caccctgagc acaagcaccg acagcaccgt gcccgccgtg    1020
tacgacagca ataagttcaa ggagtacaca cgccacgtcg aagaatacga cctgcagttc    1080
atcttccagc tctgcaccgt gaccctgacc accgacgtca tgagctacat ccacaccatg    1140
aacagcagca tcctcgataa ctggaacttc gccgtggccc ccccccccag cgcatccctc    1200
gtggatacct atcgctatct gcagagcgcc gcaatcacct gccagaagga cgcccccgcc    1260
cccgagaaga aggacccta cgatggcctg aagttctgga acgtcgatct gcgcgagaag    1320
ttctccctgg agctggacca gttccccctc ggccgcaagt cctcctccca ggcacgcgtg    1380
cgccgccgcc ccaccatcgg cccacgcaag cgccccgccg ccagcaccag cagcagcagc    1440
gccaccaagc acaagcgcaa gcgcgtcagc aagtga                              1476
```

<210> SEQ ID NO 21
<211> LENGTH: 1476
<212> TYPE: DNA
<213> ORGANISM: Artificial Sequence
<220> FEATURE:
<223> OTHER INFORMATION: The DNA sequence encoding H39N15-68T4-70S1

<400> SEQUENCE: 21

```
atgcccagcg tcgccaaggt cgtgaacacc gacgactacg tcacccgcac cgggatctac     60
tactacgccg gtccagccg cctgctgacc gtgggccacc cctactttaa ggtacctgta    120
aatggtggcc gcaagcagga aatacctaag gtgtctgcct accagtaccg cgtgttccgc    180
gtcaccctcc cagaccccaa caagttctcc atccccgacg ccagcctgta caaccccgag    240
```

```
acccagcgcc tggtgtgggc ctgcgtgggc gtcgaagtcg ggcgcgggca gcccctcggc    300
gtcggcatct ccggccaccc cctgtacaac cgccaggacg acaccgagaa tagcccttc    360 agcagcacaa caaacaagga ttcccgcgac aacgtcagcg tcgactacaa gcagacccag    420
ctctgtatca tcgggtgcgt cccagcaatc ggcgaacact ggggcaaggg caaggcctgt    480
aagccaaaca cgtgagcac cggcgattgc ccccccctgg agctggtgaa tacacccatc    540
gaagacggcg acatgatcga caccgggtac ggcgccatgg atttcggcgc cctccaggag    600
acaaagtccg aagtcccct ggacatctgc cagagcatct gcaagtaccc cgactacctc    660
cagatgagcg ccgacgtcta cggcgattcc atgttcttct gcctgcgccg cgagcagctc    720
ttcgcccgcc acttctggaa cagaggcggc atggtcggcg acaccatccc caccgacatg    780
tacatcaagg gcaccgacat cagagagaca cccagcagct acgtgtactg tccaagccca    840
tccggcagca tggtgacaag cgacagccag ctgttcaaca gccctactg gctgcacaag    900 gcacagggga taataacgg catctgctgg cacaaccagc tgttcctgac cgtcgtcgat    960
accacacgct ccacaaattt caccctgagc acaagcatcg aaagcagcat ccccagcacc   1020
tacgacccca gcaagttcaa ggagtacaca cgccacgtcg aagaatacga cctgcagttc   1080
atcttccagc tctgcaccgt gaccctgacc accgacgtca tgagctacat ccacaccatg   1140
aacagcagca tcctcgataa ctggaacttc gccgtggccc ccccccccag cgcatccctc   1200
gtggatacct atcgctatct gcagagcgcc gcaatcacct gccagaagga cgcccccgcc   1260
cccgagaaga aggaccccta cgatggcctg aagttctgga acgtcgatct gcgcgagaag   1320
ttctccctgg agctggacca gttccccctc ggccgcaagt tcctcctcca ggcacgcgtg   1380
cgccgccgcc ccaccatcgg cccacgcaag cgccccgccg ccagcaccag cagcagcagc   1440
gccaccaagc acaagcgcaa gcgcgtcagc aagtga                              1476
```

<210> SEQ ID NO 22
<211> LENGTH: 1479
<212> TYPE: DNA
<213> ORGANISM: Artificial Sequence
<220> FEATURE:
<223> OTHER INFORMATION: The DNA sequence encoding H39N15-68T4-70S2

<400> SEQUENCE: 22

```
atgcccagcg tcgccaaggt cgtgaacacc gacgactacg tcacccgcac cgggatctac     60
tactacgccg ggtccagccg cctgctgacc gtgggccacc cctacttcaa ggtcggcatg    120
aacggcgggc gcaagcagga tatccccaag gtcagcgcct accagtaccg cgtgttccgc    180
gtcaccctcc cagaccccaa caagttctcc atccccgacg ccagcctgta caaccccgag    240
acccagcgcc tggtgtgggc ctgcgtgggc gtcgaagtcg gtagaggcca gccattgggc    300
gttggtgtta gtggacatcc tttatataat agattggatg atactgaaaa ttcacatttt    360
tcctctgctg ttaatacaca ggacagtagg acaatgtgt ctgtggacta taagcagacc    420
cagctctgta tcatcgggtg cgtcccagca atcggcgaac actggggcaa gggcaaggcc    480
tgtaagccaa acaacgtgag caccggcgat tgcccccccc tggagctggt gaatacaccc    540
atcgaagacg gcgacatgat cgacaccggg tacgcgcca tggatttcgg cgccctccag    600
gagacaaagt ccgaagtccc cctggacatc tgccagagca tctgcaagta ccccgactac    660
ctccagatga gcgccgacgt ctacggcgat tccatgttct tctgcctgcg ccgcgagcag    720
ctcttcgccc gccacttctg gaacagaggc ggcatggtcg gcgacaccat ccccaccgac    780
```

-continued

| | |
|---|---|
| atgtacatca agggcaccga catcagagag acacccagca gctacgtgta ctgtccaagc | 840 |
| ccatccggca gcatggtgac aagcgacagc cagctgttca acaagcccta ctggctgcac | 900 |
| aaggcacagg ggcataataa cggcatctgc tggcacaacc agctgttcct gaccgtcgtc | 960 |
| gataccacac gctccacaaa tttcaccctg agcacaagca tcgaaagcag catccccagc | 1020 |
| acctacgacc ccagcaagtt caaggagtac acacgccacg tcgaagaata cgacctgcag | 1080 |
| ttcatcttcc agctctgcac cgtgaccctg accaccgacg tcatgagcta catccacacc | 1140 |
| atgaacagca gcatcctcga taactggaac ttcgccgtgg ccccccccc cagcgcatcc | 1200 |
| ctcgtggata cctatcgcta tctgcagagc gccgcaatca cctgccagaa ggacgccccc | 1260 |
| gcccccgaga agaaggaccc ctacgatggc ctgaagttct ggaacgtcga tctgcgcgag | 1320 |
| aagttctccc tggagctgga ccagttcccc ctcggccgca gttcctcct ccaggcacgc | 1380 |
| gtgcgccgcc gccccaccat cggcccacgc aagcgccccg ccgccagcac cagcagcagc | 1440 |
| agcgccacca gcacaagcg caagcgcgtc agcaagtga | 1479 |

<210> SEQ ID NO 23
<211> LENGTH: 1476
<212> TYPE: DNA
<213> ORGANISM: Artificial Sequence
<220> FEATURE:
<223> OTHER INFORMATION: The DNA sequence encoding H39N15-68T4-70S3

<400> SEQUENCE: 23

| | |
|---|---|
| atgcccagcg tcgccaaggt cgtgaacacc gacgactacg tcacccgcac cgggatctac | 60 |
| tactacgccg gtccagccg cctgctgacc gtgggccacc cctacttcaa ggtcggcatg | 120 |
| aacggcgggc gcaagcagga tatccccaag gtcagcgcct accagtaccg cgtgttccgc | 180 |
| gtcaccctcc cagaccccaa caagttctcc atccccgacg ccagcctgta caaccccgag | 240 |
| acccagcgcc tggtgtgggc ctgcgtgggc gtcgaagtcg ggcgcgggca gcccctcggc | 300 |
| gtcggcatct ccgccacccc cctgtacaac cgccaggacg acaccgagaa tagcccttc | 360 |
| agcagcacaa caaacaagga ttcccgcgac aacgtcagcg tcgactacaa gcagacccag | 420 |
| ctctgtatca tcgggtgcgt cccagcaatc ggcgaacact gggcaaaggg caaggcctgt | 480 |
| aagtccacta ctgtacaaca gggcgattgt ccaccactgg agctggtgaa tacacccatc | 540 |
| gaagacggcg acatgatcga caccgggtac ggcgccatgg atttcggcgc cctccaggag | 600 |
| acaaagtccg aagtccccct ggacatctgc cagagcatct gcaagtaccc cgactacctc | 660 |
| cagatgagcg ccgacgtcta cggcgattcc atgttcttct gcctgcgccg cgagcagctc | 720 |
| ttcgcccgcc acttctggaa cagaggcggc atggtcggcg acaccatccc caccgacatg | 780 |
| tacatcaagg gcaccgacat cagagagaca cccagcagct acgtgtactg tccaagccca | 840 |
| tccggcagca tggtgacaag cgacagccag ctgttcaaca gccctactg gctgcacaag | 900 |
| gcacaggggc ataataacgg catctgctgg cacaaccagc tgttcctgac cgtcgtcgat | 960 |
| accacacgct ccacaaattt caccctgagc acaagcatcg aaagcagcat ccccagcacc | 1020 |
| tacgacccca gcaagttcaa ggagtacaca cgccacgtcg aagaatacga cctgcagttc | 1080 |
| atcttccagc tctgcaccgt gaccctgacc accgacgtca tgagctacat ccacaccatg | 1140 |
| aacagcagca tcctcgataa ctggaacttc gccgtggccc cccccccag cgcatccctc | 1200 |
| gtggatacct atcgctatct gcagagcgcg gcaatcacct gccagaagga cgcccccgcc | 1260 |
| cccgagaaga aggaccccta cgatggcctg aagttctgga acgtcgatct gcgcgagaag | 1320 |
| ttctccctgg agctggacca gttcccctc ggccgcaagt tcctcctcca ggcacgcgtg | 1380 |

```
cgccgccgcc ccaccatcgg cccacgcaag cgccccgccg ccagcaccag cagcagcagc    1440
gccaccaagc acaagcgcaa gcgcgtcagc aagtga                              1476

<210> SEQ ID NO 24
<211> LENGTH: 1476
<212> TYPE: DNA
<213> ORGANISM: Artificial Sequence
<220> FEATURE:
<223> OTHER INFORMATION: The DNA sequence encoding H39N15-68T4-70S5

<400> SEQUENCE: 24
atgcccagcg tcgccaaggt cgtgaacacc gacgactacg tcacccgcac cgggatctac      60
tactacgccg gtccagccg cctgctgacc gtgggccacc cctacttcaa ggtcggcatg      120
aacggcgggc gcaagcagga tatccccaag gtcagcgcct accagtaccg cgtgttccgc    180
gtcaccctcc cagaccccaa caagttctcc atccccgacg ccagcctgta acccccgag      240 acccagcgc tggtgtgggc ctgcgtgggc gtcgaagtcg ggcgcgggca gccctcggc      300 gtcggcatct ccggccaccc cctgtacaac cgccaggacg acaccgagaa tagccccttc    360
agcagcacaa caaacaagga ttcccgcgac aacgtcagcg tcgactacaa gcagacccag    420
ctctgtatca tcgggtgcgt cccagcaatc ggcgaacact ggggcaaggg caaggcctgt    480
aagccaaaca cgtgagcac cggcgattgc ccccccctgg agctggtgaa tacacccatc     540
gaagacggcg acatgatcga caccgggtac ggcgccatgg atttcggcgc cctccaggag    600
acaaagtccg aagtccccct ggacatctgc cagagcatct gcaagtaccc cgactacctc    660
cagatgagcg ccgacgtcta cggcgattcc atgttcttct gcctgcgccg cgagcagctc    720
ttcgcccgcc acttctggaa cagaggcggc atggtcggcg acaccatccc caccgacatg    780
tacatcaagg gcaccgacat cagagagaca cccagcagct acgtgtactg tccaagccca    840
tccggcagca tggtgacaag cgacagccag ctgttcaaca gccctactg ctgcacaag      900 gcacaggggc ataataacgg catctgctgg cacaaccagc tgttcctgac cgtcgtcgat    960
accacacgct ccacaaattt caccctgagc acaagcaccg aaacagccat acctgctgta   1020
tatagcccta caaagttcaa ggagtacaca cgccacgtcg aagaatacga cctgcagttc   1080
atcttccagc tctgcaccgt gaccctgacc accgacgtca tgagctacat ccacaccatg   1140
aacagcagca tcctcgataa ctggaacttc gccgtggccc ccccccccag cgcatccctc   1200
gtggatacct atcgctatct gcagagcgcc gcaatcacct gccagaagga cgccccgcc   1260 cccgagaaga aggaccccta cgatggcctg aagttctgga acgtcgatct cgcgagaag   1320 ttctcccctgg agctggacca gttccccctc ggccgcaagt tcctcctcca ggcacgcgtg   1380
cgccgccgcc ccaccatcgg cccacgcaag cgccccgccg ccagcaccag cagcagcagc   1440
gccaccaagc acaagcgcaa gcgcgtcagc aagtga                             1476

<210> SEQ ID NO 25
<211> LENGTH: 20
<212> TYPE: PRT
<213> ORGANISM: Human papillomavirus type 68

<400> SEQUENCE: 25

Thr Ile Pro Thr Asp Met Tyr Ile Lys Gly Thr Asp Ile Arg Glu Thr
1               5                   10                  15

Pro Ser Ser Tyr
            20
```

<210> SEQ ID NO 26
<211> LENGTH: 25
<212> TYPE: PRT
<213> ORGANISM: Human papillomavirus type 70

<400> SEQUENCE: 26

Val Ser Gly His Pro Leu Tyr Asn Arg Leu Asp Asp Thr Glu Asn Ser
1               5                   10                  15

His Phe Ser Ser Ala Val Asn Thr Gln
            20                  25

<210> SEQ ID NO 27
<211> LENGTH: 13
<212> TYPE: PRT
<213> ORGANISM: Human papillomavirus type 70

<400> SEQUENCE: 27

Ala Lys Gly Lys Ala Cys Lys Ser Thr Thr Val Gln Gln
1               5                   10

<210> SEQ ID NO 28
<211> LENGTH: 12
<212> TYPE: PRT
<213> ORGANISM: Human papillomavirus type 70

<400> SEQUENCE: 28

Thr Glu Thr Ala Ile Pro Ala Val Tyr Ser Pro Thr
1               5                   10

<210> SEQ ID NO 29
<211> LENGTH: 491
<212> TYPE: PRT
<213> ORGANISM: Human papillomavirus type 39

<400> SEQUENCE: 29

Met Pro Ser Val Ala Lys Val Val Asn Thr Asp Asp Tyr Val Thr Arg
1               5                   10                  15

Thr Gly Ile Tyr Tyr Tyr Ala Gly Ser Ser Arg Leu Leu Thr Val Gly
            20                  25                  30

His Pro Tyr Phe Lys Val Gly Met Asn Gly Gly Arg Lys Gln Asp Ile
        35                  40                  45

Pro Lys Val Ser Ala Tyr Gln Tyr Arg Val Phe Arg Val Thr Leu Pro
    50                  55                  60

Asp Pro Asn Lys Phe Ser Ile Pro Asp Ala Ser Leu Tyr Asn Pro Glu
65                  70                  75                  80

Thr Gln Arg Leu Val Trp Ala Cys Val Gly Val Glu Val Gly Arg Gly
                85                  90                  95

Gln Pro Leu Gly Val Gly Ile Ser Gly His Pro Leu Tyr Asn Arg Gln
            100                 105                 110

Asp Asp Thr Glu Asn Ser Pro Phe Ser Ser Thr Thr Asn Lys Asp Ser
        115                 120                 125

Arg Asp Asn Val Ser Val Asp Tyr Lys Gln Thr Gln Leu Cys Ile Ile
    130                 135                 140

Gly Cys Val Pro Ala Ile Gly Glu His Trp Gly Lys Gly Lys Ala Cys
145                 150                 155                 160

Lys Pro Asn Asn Val Ser Thr Gly Asp Cys Pro Pro Leu Glu Leu Val
                165                 170                 175

Asn Thr Pro Ile Glu Asp Gly Asp Met Ile Asp Thr Gly Tyr Gly Ala
            180                 185                 190

```
Met Asp Phe Gly Ala Leu Gln Glu Thr Lys Ser Glu Val Pro Leu Asp
        195                 200                 205

Ile Cys Gln Ser Ile Cys Lys Tyr Pro Asp Tyr Leu Gln Met Ser Ala
        210                 215                 220

Asp Val Tyr Gly Asp Ser Met Phe Phe Cys Leu Arg Arg Glu Gln Leu
225                 230                 235                 240

Phe Ala Arg His Phe Trp Asn Arg Gly Gly Met Val Gly Asp Ala Ile
                245                 250                 255

Pro Ala Gln Leu Tyr Ile Lys Gly Thr Asp Ile Arg Ala Asn Pro Gly
                260                 265                 270

Ser Ser Val Tyr Cys Pro Ser Pro Ser Gly Ser Met Val Thr Ser Asp
                275                 280                 285

Ser Gln Leu Phe Asn Lys Pro Tyr Trp Leu His Lys Ala Gln Gly His
        290                 295                 300

Asn Asn Gly Ile Cys Trp His Asn Gln Leu Phe Leu Thr Val Val Asp
305                 310                 315                 320

Thr Thr Arg Ser Thr Asn Phe Thr Leu Ser Thr Ile Glu Ser Ser
                325                 330                 335

Ile Pro Ser Thr Tyr Asp Pro Ser Lys Phe Lys Glu Tyr Thr Arg His
                340                 345                 350

Val Glu Glu Tyr Asp Leu Gln Phe Ile Phe Gln Leu Cys Thr Val Thr
        355                 360                 365

Leu Thr Thr Asp Val Met Ser Tyr Ile His Thr Met Asn Ser Ser Ile
        370                 375                 380

Leu Asp Asn Trp Asn Phe Ala Val Ala Pro Pro Ser Ala Ser Leu
385                 390                 395                 400

Val Asp Thr Tyr Arg Tyr Leu Gln Ser Ala Ala Ile Thr Cys Gln Lys
                405                 410                 415

Asp Ala Pro Ala Pro Glu Lys Lys Asp Pro Tyr Asp Gly Leu Lys Phe
                420                 425                 430

Trp Asn Val Asp Leu Arg Glu Lys Phe Ser Leu Glu Leu Asp Gln Phe
        435                 440                 445

Pro Leu Gly Arg Lys Phe Leu Leu Gln Ala Arg Val Arg Arg Pro
        450                 455                 460

Thr Ile Gly Pro Arg Lys Arg Pro Ala Ala Ser Thr Ser Ser Ser Ser
465                 470                 475                 480

Ala Thr Lys His Lys Arg Lys Arg Val Ser Lys
                485                 490

<210> SEQ ID NO 30
<211> LENGTH: 1476
<212> TYPE: DNA
<213> ORGANISM: Human papillomavirus type 39

<400> SEQUENCE: 30
atgcccagcg tcgccaaggt cgtgaacacc gacgactacg tcacccgcac cgggatctac      60
tactacgccg gtccagccg cctgctgacc gtgggccacc cctacttcaa ggtcggcatg      120
aacggcgggc gcaagcagga tatccccaag gtcagcgcct accagtaccg cgtgttccgc      180
gtcaccctcc cagaccccaa caagttctcc atccccgacg ccagcctgta caaccccgag      240
acccagcgcc tggtgtgggc ctgcgtgggc gtcgaagtcg ggcgcgggca gccctcggc      300 gtcggcatct ccgccacccc ctgtacaac cgccaggacg acaccgagaa tagcccttc      360 agcagcacaa caaacaagga ttcccgcgac aacgtcagcg tcgactacaa gcagacccag      420
```

```
ctctgtatca tcgggtgcgt cccagcaatc ggcgaacact ggggcaaggg caaggcctgt    480
aagccaaaca acgtgagcac cggcgattgc ccccccctgg agctggtgaa tacacccatc    540
gaagacggcg acatgatcga caccgggtac ggcgccatgg atttcggcgc cctccaggag    600
acaaagtccg aagtccccct ggacatctgc cagagcatct gcaagtaccc cgactacctc    660
cagatgagcg ccgacgtcta cggcgattcc atgttcttct gcctgcgccg cgagcagctc    720
ttcgcccgcc acttctggaa ccgcggcggc atggtcggcg atgcaatccc cgcacagctc    780
tacatcaagg ggaccgacat ccgcgccaat ccaggctcca gcgtgtattg ccaagcccca    840
tccggcagca tggtgacaag cgacagccag ctgttcaaca gcccctactg gctgcacaag    900
gcacaggggc ataataacgg catctgctgg cacaaccagc tgttcctgac cgtcgtcgat    960
accacacgct ccacaaattt cacccctgagc acaagcatcg aaagcagcat ccccagcacc   1020
tacgacccca gcaagttcaa ggagtacaca cgccacgtcg aagaatacga cctgcagttc   1080
atcttccagc tctgcaccgt gaccctgacc accgacgtca tgagctacat ccacaccatg   1140
aacagcagca tcctcgataa ctggaacttc gccgtggccc cccccccag cgcatccctc    1200 gtggatacct atcgctatct gcagagcgcc gcaatcacct gccagaagga cgcccccgcc   1260
cccgagaaga aggaccccta cgatggcctg aagttctgga acgtcgatct cgcgcgagaag   1320 ttctccctgg agctggacca gttccccctc ggccgcaagt cctcctcca ggcacgcgtg     1380 cgccgccgcc ccaccatcgg cccacgcaag cgccccgccg ccagcaccag cagcagcagc   1440
gccaccaagc acaagcgcaa gcgcgtcagc aagtga                              1476
```

<210> SEQ ID NO 31
<211> LENGTH: 497
<212> TYPE: PRT
<213> ORGANISM: Human papillomavirus type 70

<400> SEQUENCE: 31

```
Met Val Tyr Leu Pro Pro Ser Val Ala Lys Val Val Asn Thr Asp
1               5                   10                  15

Asp Tyr Val Thr Arg Thr Gly Ile Tyr Tyr Tyr Ala Gly Ser Ser Arg
            20                  25                  30

Leu Leu Thr Val Gly His Pro Tyr Phe Lys Val Pro Val Asn Gly Gly
        35                  40                  45

Arg Lys Gln Glu Ile Pro Lys Val Ser Ala Tyr Gln Tyr Arg Val Phe
    50                  55                  60

Arg Val Ser Leu Pro Asp Pro Asn Lys Phe Gly Leu Pro Asp Pro Ser
65                  70                  75                  80

Leu Tyr Asn Pro Asp Thr Gln Arg Leu Val Trp Ala Cys Ile Gly Val
                85                  90                  95

Glu Ile Gly Arg Gly Gln Pro Leu Gly Val Gly Val Ser Gly His Pro
            100                 105                 110

Leu Tyr Asn Arg Leu Asp Asp Thr Glu Asn Ser His Phe Ser Ser Ala
        115                 120                 125

Val Asn Thr Gln Asp Ser Arg Asp Asn Val Ser Val Asp Tyr Lys Gln
    130                 135                 140

Thr Gln Leu Cys Ile Ile Gly Cys Val Pro Ala Met Gly Glu His Trp
145                 150                 155                 160

Ala Lys Gly Lys Ala Cys Lys Ser Thr Thr Val Gln Gln Gly Asp Cys
                165                 170                 175

Pro Pro Leu Glu Leu Val Asn Thr Ala Ile Glu Asp Gly Asp Met Ile
```

```
            180                 185                 190
Asp Thr Gly Tyr Gly Ala Met Asp Phe Arg Thr Leu Gln Glu Thr Lys
            195                 200                 205
Ser Glu Val Pro Leu Asp Ile Cys Gln Ser Val Cys Lys Tyr Pro Asp
            210                 215                 220
Tyr Leu Gln Met Ser Ala Asp Val Tyr Gly Asp Ser Met Phe Phe Cys
225                 230                 235                 240
Leu Arg Lys Glu Gln Leu Phe Ala Arg His Phe Trp Asn Arg Gly Gly
                245                 250                 255
Met Val Gly Asp Thr Ile Pro Ser Glu Leu Tyr Ile Lys Gly Thr Asp
            260                 265                 270
Ile Arg Asp Arg Pro Gly Thr His Val Tyr Ser Pro Ser Pro Ser Gly
            275                 280                 285
Ser Met Val Ser Ser Asp Ser Gln Leu Phe Asn Lys Pro Tyr Trp Leu
            290                 295                 300
His Lys Ala Gln Gly His Asn Asn Gly Ile Cys Trp His Asn Gln Leu
305                 310                 315                 320
Phe Ile Thr Val Val Asp Thr Thr Arg Ser Thr Asn Phe Thr Leu Ser
                325                 330                 335
Ala Cys Thr Glu Thr Ala Ile Pro Ala Val Tyr Ser Pro Thr Lys Phe
                340                 345                 350
Lys Glu Tyr Thr Arg His Val Glu Glu Tyr Asp Leu Gln Phe Ile Phe
                355                 360                 365
Gln Leu Cys Thr Ile Thr Leu Thr Ala Asp Val Met Ala Tyr Ile His
            370                 375                 380
Thr Met Asn Pro Ala Ile Leu Asp Asn Trp Asn Ile Gly Val Thr Pro
385                 390                 395                 400
Pro Pro Ser Ala Ser Leu Val Asp Thr Tyr Arg Tyr Leu Gln Ser Ala
                405                 410                 415
Ala Ile Ala Cys Gln Lys Asp Ala Pro Ala Pro Glu Lys Lys Asp Pro
                420                 425                 430
Tyr Asp Asp Leu Lys Phe Trp Asn Val Asp Leu Lys Glu Lys Phe Ser
                435                 440                 445
Thr Glu Leu Asp Gln Phe Pro Leu Gly Arg Lys Phe Leu Leu Gln Val
            450                 455                 460
Gly Ala Arg Arg Arg Pro Thr Ile Gly Pro Arg Lys Arg Pro Ala Ser
465                 470                 475                 480
Ala Lys Ser Ser Ser Ala Ser Lys His Lys Arg Lys Arg Val Ser
                485                 490                 495
Lys

<210> SEQ ID NO 32
<211> LENGTH: 1494
<212> TYPE: DNA
<213> ORGANISM: Human papillomavirus type 70

<400> SEQUENCE: 32
atggtgtatt tgccaccccc ttctgtggcg aaggttgtca atacagatga ttatgtaaca      60
cgtacaggca tatattatta tgctggaagc tctcgcttat taacagtagg gcatccttat     120
tttaaggtac ctgtaaatgg tggccgcaag caggaaatac ctaaggtgtc tgcatatcag     180
tatagggtat ttagggtatc cctacctgat cctaataagt ttggccttcc ggatccttcc     240
ctttataatc ctgacacaca acgcctggta tgggcctgta taggtgtgga aattggtaga     300
```

| | |
|---|---|
| ggccagccat tgggcgttgg tgttagtgga catcctttat ataatagatt ggatgatact | 360 |
| gaaaattcac attttttcctc tgctgttaat acacaggaca gtagggacaa tgtgtctgtg | 420 |
| gactataagc agacacagtt atgtattata ggctgtgttc ctgctatggg agagcactgg | 480 |
| gcaaagggca aggcctgtaa gtccactact gtacaacagg gcgattgtcc accattagaa | 540 |
| ttagttaata ctgcaattga ggatggcgat atgatagata caggctatgg agccatggac | 600 |
| tttcgtacat tgcaggaaac caaaagtgag gtaccactag atatttgcca atccgtgtgt | 660 |
| aaatatcctg attatttgca gatgtctgct gatgtatatg gggacagtat gtttttttgt | 720 |
| ttgcgcaagg aacagttatt tgccagacac ttttggaata gaggtggcat ggtgggcgac | 780 |
| acaataccct cagagttata tattaaaggc acggatatac gtgatcgtcc tggtactcat | 840 |
| gtatattccc cttccccaag tggctctatg gtttcttctg attcccagtt gtttaataag | 900 |
| ccctattggt tgcataaggc ccagggacac aataatggca tttgttggca taaccagttg | 960 |
| tttattactg tggtggacac tacacgtagt actaatttta cattgtctgc ctgcaccgaa | 1020 |
| acagccatac ctgctgtata tagccctaca aagtttaagg aatatactag gcatgtggag | 1080 |
| gaatatgatt tacaatttat atttcagttg tgtactatca cattaactgc agacgttatg | 1140 |
| gcctacatcc atactatgaa tcctgcaatt ttggacaatt ggaatatagg cgttaccct | 1200 |
| ccaccatctg caagcttggt ggacacgtat aggtatttac aatcagcagc tatagcatgt | 1260 |
| cagaaggatg ctcctgcacc tgaaaaaaag gatccctatg acgatttaaa attttggaat | 1320 |
| gttgatttaa aggaaaagtt tagtacagaa ctagatcagt ttcctttggg gcgcaaattt | 1380 |
| ttactacagg taggggctcg cagacgtcct actataggcc ctcgcaaacg ccctgcatca | 1440 |
| gctaaatcgt cttcctcagc ctctaaacac aaacggaaac gtgtgtccaa gtaa | 1494 |

<210> SEQ ID NO 33
<211> LENGTH: 9
<212> TYPE: PRT
<213> ORGANISM: Human papillomavirus type 68

<400> SEQUENCE: 33

Pro Met Ser Gly Gly Arg Lys Gln Gly
1               5

<210> SEQ ID NO 34
<211> LENGTH: 35
<212> TYPE: PRT
<213> ORGANISM: Human papillomavirus type 68

<400> SEQUENCE: 34

Leu Ser Gly His Pro Leu Tyr Asn Arg Leu Asp Asp Thr Glu Asn Ser
1               5                   10                  15

Pro Phe Ser Ser Asn Lys Asn Pro Lys Asp Ser Arg Asp Asn Val Ala
            20                  25                  30

Val Asp Cys
        35

<210> SEQ ID NO 35
<211> LENGTH: 13
<212> TYPE: PRT
<213> ORGANISM: Human papillomavirus type 68

<400> SEQUENCE: 35

Ala Lys Gly Lys Ser Cys Lys Pro Thr Asn Val Gln Gln
1               5                   10

<210> SEQ ID NO 36
<211> LENGTH: 12
<212> TYPE: PRT
<213> ORGANISM: Human papillomavirus type 68

<400> SEQUENCE: 36

Thr Asp Ser Thr Val Pro Ala Val Tyr Asp Ser Asn
1               5                   10

<210> SEQ ID NO 37
<211> LENGTH: 9
<212> TYPE: PRT
<213> ORGANISM: Human papillomavirus type 70

<400> SEQUENCE: 37

Pro Val Asn Gly Gly Arg Lys Gln Glu
1               5

<210> SEQ ID NO 38
<211> LENGTH: 48
<212> TYPE: DNA
<213> ORGANISM: Artificial Sequence
<220> FEATURE:
<223> OTHER INFORMATION: Primer

<400> SEQUENCE: 38
ttcaaggtcc ccatgagcgg cgggcgcaag caggatatcc ccaaggtc          48

<210> SEQ ID NO 39
<211> LENGTH: 48
<212> TYPE: DNA
<213> ORGANISM: Artificial Sequence
<220> FEATURE:
<223> OTHER INFORMATION: Primer

<400> SEQUENCE: 39
cccgccgctc atggggacct tgaagtaggg gtggcccacg gtcagcag          48

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
gacttcgacg cccacgcagg ccca                                    24

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
aagcagaccc agctctgtat catc                                    24

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
ttcgccgatt gctgggacgc accc                                        24

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
ctggagctgg tgaatacacc catc                                        24

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
gtggcgggcg aagagctgct cgcg                                        24

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
tgtccaagcc catccggcag catg                                        24

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
gcttgtgctc agggtgaaat ttgtggagcg                                  30

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
ttcaaggagt acacacgcca cgtcgaagaa                                  30

<210> SEQ ID NO 48
<211> LENGTH: 45
<212> TYPE: DNA
<213> ORGANISM: Artificial Sequence
<220> FEATURE:
<223> OTHER INFORMATION: Primer

<400> SEQUENCE: 48
tgggcctgcg tgggcgtcga agtcggcaga ggccagcccc tgggc                 45

<210> SEQ ID NO 49
<211> LENGTH: 45
<212> TYPE: DNA

```
<213> ORGANISM: Artificial Sequence
<220> FEATURE:
<223> OTHER INFORMATION: Primer

<400> SEQUENCE: 49
gatgatacag agctgggtct gcttgcagtc cacggccacg ttgtc            45

<210> SEQ ID NO 50
<211> LENGTH: 45
<212> TYPE: DNA
<213> ORGANISM: Artificial Sequence
<220> FEATURE:
<223> OTHER INFORMATION: Primer

<400> SEQUENCE: 50
gggtgcgtcc cagcaatcgg cgaacactgg gccaagggca agagc            45

<210> SEQ ID NO 51
<211> LENGTH: 45
<212> TYPE: DNA
<213> ORGANISM: Artificial Sequence
<220> FEATURE:
<223> OTHER INFORMATION: Primer

<400> SEQUENCE: 51
gatgggtgta ttcaccagct ccagaggggg gcagtcgccc tgctg            45

<210> SEQ ID NO 52
<211> LENGTH: 45
<212> TYPE: DNA
<213> ORGANISM: Artificial Sequence
<220> FEATURE:
<223> OTHER INFORMATION: Primer

<400> SEQUENCE: 52
cgcgagcagc tcttcgcccg ccacttctgg aacagaggcg gcatg            45

<210> SEQ ID NO 53
<211> LENGTH: 45
<212> TYPE: DNA
<213> ORGANISM: Artificial Sequence
<220> FEATURE:
<223> OTHER INFORMATION: Primer

<400> SEQUENCE: 53
catgctgccg gatgggcttg gacagtacac gtagctgctg ggtgt            45

<210> SEQ ID NO 54
<211> LENGTH: 51
<212> TYPE: DNA
<213> ORGANISM: Artificial Sequence
<220> FEATURE:
<223> OTHER INFORMATION: Primer

<400> SEQUENCE: 54
cgctccacaa atttcaccct gagcacaagc accgacagca ccgtgcccgc c      51

<210> SEQ ID NO 55
<211> LENGTH: 51
<212> TYPE: DNA
<213> ORGANISM: Artificial Sequence
<220> FEATURE:
<223> OTHER INFORMATION: Primer

<400> SEQUENCE: 55
ttcttcgacg tggcgtgtgt actccttgaa cttattgctg tcgtacacgg c      51
```

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56 gtagggtgg cccacggtca g                    21

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
gcctaccagt accgcgtgtt c                    21

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
gacttcgacg cccacgcagg c                    21

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
aagcagaccc agctctgtat c                    21

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
ttcgccgatt gctgggacgc a                    21

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
ctggagctgg tgaatacacc c                    21

<210> SEQ ID NO 62
<211> LENGTH: 21
<212> TYPE: DNA
<213> ORGANISM: Artificial Sequence
<220> FEATURE:

<223> OTHER INFORMATION: Primer

<400> SEQUENCE: 62
gcttgtgctc agggtgaaat t                                         21

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
ttcaaggagt acacacgcca c                                         21

<210> SEQ ID NO 64
<211> LENGTH: 42
<212> TYPE: DNA
<213> ORGANISM: Artificial Sequence
<220> FEATURE:
<223> OTHER INFORMATION: Primer

<400> SEQUENCE: 64
ctgaccgtgg gccacccta ctttaaggta cctgtaaatg gt                   42

<210> SEQ ID NO 65
<211> LENGTH: 42
<212> TYPE: DNA
<213> ORGANISM: Artificial Sequence
<220> FEATURE:
<223> OTHER INFORMATION: Primer

<400> SEQUENCE: 65
gaacacgcgg tactggtagg cagacacctt aggtatttcc tg                  42

<210> SEQ ID NO 66
<211> LENGTH: 42
<212> TYPE: DNA
<213> ORGANISM: Artificial Sequence
<220> FEATURE:
<223> OTHER INFORMATION: Primer

<400> SEQUENCE: 66
gcctgcgtgg gcgtcgaagt cggtagaggc cagccattgg gc                  42

<210> SEQ ID NO 67
<211> LENGTH: 42
<212> TYPE: DNA
<213> ORGANISM: Artificial Sequence
<220> FEATURE:
<223> OTHER INFORMATION: Primer

<400> SEQUENCE: 67
gatacagagc tgggtctgct tatagtccac agacacattg tc                  42

<210> SEQ ID NO 68
<211> LENGTH: 42
<212> TYPE: DNA
<213> ORGANISM: Artificial Sequence
<220> FEATURE:
<223> OTHER INFORMATION: Primer

<400> SEQUENCE: 68
tgcgtcccag caatcggcga acactgggca aagggcaagg cc                  42

```
<210> SEQ ID NO 69
<211> LENGTH: 45
<212> TYPE: DNA
<213> ORGANISM: Artificial Sequence
<220> FEATURE:
<223> OTHER INFORMATION: Primer

<400> SEQUENCE: 69
gggtgtattc accagctcca gtggtggaca atcgccctgt tgtac          45

<210> SEQ ID NO 70
<211> LENGTH: 42
<212> TYPE: DNA
<213> ORGANISM: Artificial Sequence
<220> FEATURE:
<223> OTHER INFORMATION: Primer

<400> SEQUENCE: 70
aatttcaccc tgagcacaag caccgaaaca gccatacctg ct             42

<210> SEQ ID NO 71
<211> LENGTH: 42
<212> TYPE: DNA
<213> ORGANISM: Artificial Sequence
<220> FEATURE:
<223> OTHER INFORMATION: Primer

<400> SEQUENCE: 71
gtggcgtgtg tactccttga actttgtagg gctatataca gc             42
```

MUTANT OF L1 PROTEIN OF HUMAN PAPILLOMAVIRUS TYPE 39

The present application is a National Stage application of International Application No. PCT/CN2019/089988, filed Jun. 4, 2019, which is based on and claims the benefit of priority from Chinese application No. 201810563378.0, filed on Jun. 4, 2018, the disclosures of both of which are incorporated herein by reference in their entirety.

SEQUENCE LISTING

The instant application contains a Sequence Listing, which has been submitted electronically in ASCII format and is hereby incorporated by reference in its entirety. Said ASCII copy, created Dec. 1, 2020, is named IEC180088PCT-seq1-EN and is 98,304 bytes in size.

TECHNICAL FIELD

The invention relates to the field of molecular virology and immunology. In particular, the invention relates to a mutated HPV39 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV39 and HPV68, or HPV39, HPV68 and HPV70), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

BACKGROUND ART

Human Papillomavirus (HPV) mainly causes warts in skin and mucosa. HPV types are divided into high-risk types and low-risk types depending on their association with tumorigenesis. Among them, infection by high-risk HPV types has been demonstrated to be the leading cause of genital cancer including cervical cancer in women; and low-risk HPV types mainly cause condyloma acuminatum. The most effective way to prevent and control HPV infection is to vaccinate HPV vaccines, particularly vaccines against high-risk HPV types causing cervical cancer.

Major capsid protein L1 of HPV has the characteristic of self-assembling into hollow Virus-Like Particle (VLP). HPV VLP has a symmetrical icosahedral structure composed of 72 pentamers of major capsid protein L1 (Doorbar, J. and P. H. Gallimore. 1987. J Virol, 61(9): 2793-9). HPV VLP is highly similar to natural HPV in terms of structure, retains most of the neutralizing epitopes of natural virus, and can induce the generation of high-titer neutralizing antibodies (Kirnbauer, R., F. Booy, et al. 1992 Proc Natl Acad Sci USA 89(24): 12180-4).

However, the existing studies show that HPV VLPs mainly induce the generation of neutralizing antibodies against the same HPV type, produce the protective immunity against the same HPV type, and only have low cross-protective effect among a few highly homologous HPV types (Sara L. Bissett, Giada Mattiuzzo, et al. 2014 Vaccine. 32:6548-6555). Therefore, the existing HPV vaccines have a very limited protection range. In general, VLP of one HPV type can only be used to prevent infection by the same HPV type. In this case, if it needs to broaden the protection range of HPV vaccines, the only way is to add VLPs of more HPV types in vaccines. Currently, the commercially available HPV vaccines, including Gardasil® from Merck (which is a quadrivalent vaccine against HPV16, 18, 6 and 11), Cervarix® from GSK (which is a bivalent vaccine against HPV16 and 18), and Gardasil®9 from Merck (which is a 9-valent vaccine against HPV6, 11, 16, 18, 31, 33, 45, 52 and 58), are prepared by combining VLPs of multiple HPV types. However, such a solution would greatly increase the production cost of HPV vaccines, and might cause safety problem due to an increase in immunizing dose.

Therefore, it is urgent in the art to develop HPV virus-like particles capable of inducing the generation of protective neutralizing antibodies against multiple HPV types, so as to prevent infection by multiple HPV types, and a disease caused by the infection, such as cervical cancer and condyloma acuminatum, more economically and effectively.

CONTENTS OF INVENTION

The invention is at least partially based on the inventors' surprising discovery: after substitution of a specific segment of L1 protein of Human Papillomavirus (HPV) Type 39 with the corresponding segment of L1 protein of a second HPV type (such as HPV68), the mutated HPV39 L1 protein thus obtained can induce the generation of high-titer neutralizing antibodies against HPV39 and the second HPV type (such as HPV68) in organisms, and its protection effect is comparable to that of a mixture of HPV39 VLP and VLP of the second HPV type, its protection effect against HPV68 is comparable to that of HPV68 VLP alone, and its protection effect against the second HPV type (such as HPV68) is comparable to that of the VLP of the second HPV type alone.

In addition, based on the substitution above, another specific segment of HPV39 L1 protein can be further substituted with the corresponding segment of L1 protein of a third HPV type (such as HPV70), and the mutated HPV39 L1 protein having double substitutions thus obtained can induce the generation of high-titer neutralizing antibodies against HPV39, the second HPV type (such as HPV68) and the third HPV type (such as HPV70); and its protection effect is comparable to that of a mixture of HPV39 VLP, VLP of the second HPV type and VLP of the third HPV type, its protection effect against HPV39 is comparable to that of HPV39 VLP alone, its protection effect against the second HPV type (such as HPV68) is comparable to that of the VLP of the second HPV type alone, and its protection effect against the third HPV type (such as HPV70) is comparable to that of the VLP of the third HPV type alone.

Therefore, in an aspect, the invention provides a mutated HPV39 L1 protein or a variant thereof, wherein as compared with a wild type HPV39 L1 protein, the mutated HPV39 L1 protein has the following mutations:

(1) N-terminal truncation of 1-25 amino acids, for example 1-5, 1-10, 1-15, 1-20, 5-15, 10-15, 10-20, or 15-20 amino acids; and (2) substitution of amino acid residues at positions 269-288 of the wild type HPV39 L1 protein with amino acid residues at the corresponding positions of a L1 protein of a second type of wild-type HPV;

and, the variant differs from the mutated HPV39 L1 protein only by substitution (preferably conservative substitution), addition or deletion of one or more (e.g. 1, 2, 3, 4, 5, 6, 7, 8 or 9) amino acids, and retains the function of the mutated HPV39 L1 protein, i.e. capability of inducing generation of neutralizing antibodies against at least two HPV types (e.g. HPV39 and HPV68, or HPV39, HPV68 and HPV70).

In some preferred embodiments, the mutated HPV39 L1 protein optionally further has the following mutation:

(3)(a) substitution of amino acid residues at positions 117-140 of the wild type HPV39 L1 protein with amino acid residues at the corresponding positions of a L1 protein of a third type of wild-type HPV; or (b) substitution of amino acid residues at positions 169-181 of the wild type HPV39 L1 protein with amino acid residues at the corresponding positions of a L1 protein of a third type of wild-type HPV; or (c) substitution of amino acid residues at positions 347-358 of the wild type HPV39 L1 protein with amino acid residues at the corresponding positions of a L1 protein of a third type of wild-type HPV.

In some preferred embodiments, the mutated HPV39 L1 protein has 3, 5, 8, 10, 12, 15, 18, 20 or 22 amino acids truncated at N-terminal, as compared with the wild type HPV39 L1 protein. In some preferred embodiments, the mutated HPV39 L1 protein has 15 amino acids truncated at N-terminal, as compared with the wild type HPV39 L1 protein.

In some preferred embodiments, the second type of wild-type HPV is HPV68. In some preferred embodiments, the amino acid residues at the corresponding positions as described in (2) are amino acid residues at positions 270-289 of a wild type HPV68 L1 protein. In some preferred embodiments, the third type of wild-type HPV is HPV70. In some preferred embodiments, the amino acid residues at the corresponding positions as described in (3) (a) are amino acid residues at positions 117-141 of a wild type HPV70 L1 protein. In some preferred embodiments, the amino acid residues at the corresponding positions as described in (3) (b) are amino acid residues at positions 170-182 of a wild type HPV70 L1 protein. In some preferred embodiments, the amino acid residues at the corresponding positions as described in (3) (c) are amino acid residues at positions 348-359 of a wild type HPV70 L1 protein.

In some preferred embodiments, the wild type HPV39 L1 protein has an amino acid sequence as set forth in SEQ ID NO: 1.

In some preferred embodiments, the wild type HPV68 L1 protein has an amino acid sequence as set forth in SEQ ID NO: 2.

In some preferred embodiments, the wild type HPV70 L1 protein has an amino acid sequence as set forth in SEQ ID NO: 3.

In some preferred embodiments, the amino acid residues at positions 270-289 of the wild type HPV68 L1 protein have a sequence as set forth in SEQ ID NO: 25.

In some preferred embodiments, the amino acid residues at positions 117-141 of the wild type HPV70 L1 protein have a sequence as set forth in SEQ ID NO: 26.

In some preferred embodiments, the amino acid residues at positions 170-182 of the wild type HPV70 L1 protein have a sequence as set forth in SEQ ID NO: 27.

In some preferred embodiments, the amino acid residues at positions 348-359 of the wild type HPV70 L1 protein have a sequence as set forth in SEQ ID NO: 28.

In some preferred embodiments, the mutated HPV39 L1 protein has an amino acid sequence selected from the group consisting of: SEQ ID NO: 7, 10, 11 and 12.

In another aspect, the invention provides an isolated nucleic acid, encoding the mutated HPV39 L1 protein or a variant thereof as described above. In another aspect, the invention provides a vector comprising the isolated nucleic acid. In some preferred embodiments, the isolated nucleic acid according to the invention has a nucleotide sequence selected from the group consisting of: SEQ ID NO: 19, 22, 23 and 24.

Vectors useful for insertion of a polynucleotide of interest are well known in the art, including, but not limited to cloning vectors and expression vectors. In one embodiment, the vectors are, for example, plasmids, cosmids, phages, etc.

In another aspect, the invention further relates to a host cell comprising the isolated nucleic acid or the vector. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell and 293TT cell.

In another aspect, the invention relates to a HPV virus-like particle, comprising or consisting of the mutated HPV39 L1 protein or a variant thereof according to the invention.

In some preferred embodiments, the HPV virus-like particle according to the invention comprises the mutated HPV39 L1 protein, which has N-terminal truncation of 1-25 amino acids, for example, 1-5, 1-10, 1-15, 1-20, 5-15, 10-15, 10-20 or 15-20 amino acids, e.g. 3, 5, 8, 11, 13, 15, 18, 20 or 22 amino acids, as compared to a wild type HPV39 L1 protein, and substitution of the amino acid residues at positions 269-288 of the wild type HPV39 L1 protein with the amino acid residues at positions 270-289 of a wild type HPV68 L1 protein.

In some preferred embodiments, the HPV virus-like particle according to the invention comprises the mutated HPV39 L1 protein, which has N-terminal truncation of 1-25 amino acids, for example, 1-5, 1-10, 1-15, 1-20, 5-15, 10-15, 10-20 or 15-20 amino acids, e.g. 3, 5, 8, 11, 13, 15, 18, 20 or 22 amino acids, as compared to a wild type HPV39 L1 protein, and substitution of the amino acid residues at positions 269-288 of the wild type HPV39 L1 protein with the amino acid residues at positions 270-289 of a wild type HPV68 L1 protein, and substitution of the amino acid residues at positions 117-140 of the wild type HPV39 L1 protein with the amino acid residues at positions 117-141 of a wild type HPV70 L1 protein.

In some preferred embodiments, the HPV virus-like particle according to the invention comprises the mutated HPV39 L1 protein, which has N-terminal truncation of 1-25 amino acids, for example, 1-5, 1-10, 1-15, 1-20, 5-15, 10-15, 10-20 or 15-20 amino acids, e.g. 3, 5, 8, 11, 13, 15, 18, 20 or 22 amino acids, as compared to a wild type HPV39 L1 protein, and substitution of the amino acid residues at positions 269-288 of the wild type HPV39 L1 protein with the amino acid residues at positions 270-289 of a wild type HPV68 L1 protein, and substitution of the amino acid residues at positions 169-181 of the wild type HPV39 L1 protein with the amino acid residues at positions 170-182 of a wild type HPV70 L1 protein.

In some preferred embodiments, the HPV virus-like particle according to the invention comprises the mutated HPV39 L1 protein, which has N-terminal truncation of 1-25 amino acids, for example, 1-5, 1-10, 1-15, 1-20, 5-15, 10-15, 10-20 or 15-20 amino acids, e.g. 3, 5, 8, 11, 13, 15, 18, 20 or 22 amino acids, as compared to a wild type HPV39 L1 protein, and substitution of the amino acid residues at positions 269-288 of the wild type HPV39 L1 protein with the amino acid residues at positions 270-289 of a wild type HPV68 L1 protein, and substitution of the amino acid residues at positions 347-358 of the wild type HPV39 L1 protein with the amino acid residues at positions 348-359 of a wild type HPV70 L1 protein.

In a particularly preferred embodiment, the HPV virus-like particle according to the invention comprises the mutated HPV39 L1 protein, which has a sequence as set forth in SEQ ID NO: 7, 10, 11 or 12.

In another aspect, the invention further relates to a composition comprising the mutated HPV39 L1 protein or a variant thereof, the isolated nucleic acid, the vector, the host cell, or the HPV virus-like particle. In some preferred embodiments, the composition comprises the mutated HPV39 L1 protein or a variant thereof according to the invention. In some preferred embodiments, the composition comprises the HPV virus-like particle according to the invention.

In another aspect, the invention further relates to a pharmaceutical composition or vaccine, comprising the HPV virus-like particle according to the invention, and optionally a pharmaceutically acceptable carrier and/or excipient. The pharmaceutical composition or vaccine according to the invention can be used for preventing HPV infection, or a disease caused by HPV infection, such as cervical cancer and condyloma acuminatum.

In some preferred embodiments, the HPV virus-like particle is present in an amount effective for preventing HPV infection or a disease caused by HPV infection. In some preferred embodiments, the HPV infection is infection by one or more HPV types (e.g. HPV39 infection, HPV68 infection and/or HPV70 infection). In some preferred embodiments, the disease caused by HPV infection is selected from the group consisting of cervical cancer and condyloma acuminatum.

The pharmaceutical composition or vaccine according to the invention may be administered by methods well known in the art, for example, but not limited to, orally or by injection. In the invention, a particularly preferred administration route is injection.

In some preferred embodiments, the pharmaceutical composition or vaccine according to the invention is administrated in a form of a unit dosage. For example, but not for limiting the invention, each unit dosage contains 5 µg-80 µg, preferably 20 µg-40 µg of HPV virus-like particle.

In another aspect, the invention relates to a method for preparing the mutated HPV39 L1 protein or a variant thereof as described above, comprising expressing the mutated HPV39 L1 protein or a variant thereof in a host cell, and then recovering the mutated HPV39 L1 protein or a variant thereof from a culture of the host cell.

In some preferred embodiments, the host cell is *E. coli*.

In some preferred embodiments, the method comprises the steps of: expressing the mutated HPV39 L1 protein or a variant thereof in *E. coli*, and then obtaining the mutated HPV39 L1 protein or a variant thereof by purifying a lysate supernatant of the *E. coli*. In some preferred embodiments, the mutated HPV39 L1 protein or a variant thereof is recovered from the lysate supernatant of the *E. coli* by chromatography (e.g. cation-exchange chromatography, hydroxyapatite chromatography and/or hydrophobic interaction chromatography).

In another aspect, the invention relates to a method for preparing a vaccine, comprising combining the HPV virus-like particle according to the invention with a pharmaceutically acceptable carrier and/or excipient.

In another aspect, the invention relates to a method for preventing HPV infection or a disease caused by HPV infection, comprising administering to a subject a prophylactically effective amount of the HPV virus-like particle or the pharmaceutical composition or vaccine according to the invention. In a preferred embodiment, the HPV infection is infection by one or more HPV types (e.g. HPV39 infection, HPV68 infection and/or HPV70 infection). In another preferred embodiment, the disease caused by HPV infection includes, but is not limited to cervical cancer and condyloma acuminatum. In another preferred embodiment, the subject is mammal, such as human.

In another aspect, the invention further relates to use of the mutated HPV39 L1 protein or a variant thereof or the HPV virus-like particle according to the invention in the manufacture of a pharmaceutical composition or vaccine for preventing HPV infection or a disease caused by HPV infection. In a preferred embodiment, the HPV infection is infection by one or more HPV types (e.g. HPV39 infection, HPV68 infection and/or HPV70 infection). In another preferred embodiment, the disease caused by HPV infection includes, but is not limited to, cervical cancer and condyloma acuminatum.

In another aspect, the invention further relates to the mutated HPV39 L1 protein or a variant thereof or the HPV virus-like particle according to the invention for the prevention of HPV infection or a disease caused by HPV infection. In a preferred embodiment, the HPV infection is infection by one or more HPV types (e.g. HPV39 infection, HPV68 infection and/or HPV70 infection). In another preferred embodiment, the disease caused by HPV infection includes, but is not limited to, cervical cancer and condyloma acuminatum.

Definitions of Terms in Present Invention

In the invention, unless otherwise specified, the scientific and technical terms used herein have the meanings generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a second type of wild-type HPV" refers to a wild-type HPV type other than HPV39. In the invention, a second type of wild-type HPV is preferably wild type HPV68.

According to the invention, the term "a third type of wild-type HPV" refers to a wild-type HPV type other than HPV39 and the second type of wild-type HPV. In the invention, a third type of wild-type HPV is preferably wild type HPV70.

According to the invention, the expression "corresponding positions" refers to the equivalent positions of the sequences being compared when the sequences are optimally aligned, i.e. the sequences are aligned to obtain a highest percentage of identity.

According to the invention, the term "wild type HPV39 L1 protein" refers to the naturally-occurring major capsid protein L1 in Human Papillomavirus Type 39 (HPV39). The sequence of wild type HPV39 L1 protein is well known in the art, and can be found in public database (such as Accession No. P24838.1, ARQ82617.1, AGU90549.1 and AEP23084.1 in NCBI database).

In the invention, when an amino acid sequence of wild type HPV39 L1 protein is mentioned, it is described by reference to the sequence as set forth in SEQ ID NO: 1. For example, the expression "amino acid residues at positions 53-61 of a wild type HPV39 L1 protein" refers to the amino acid residues at positions 53-61 of the polypeptide as set forth in SEQ ID NO: 1. However, a person skilled in the art understands that wild type HPV39 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV39 isolates, and have substantively the same biological function. Therefore, in the invention, the term "wild type HPV39 L1 protein" includes not only the protein as set forth in SEQ ID NO: 1, but also L1 protein of various HPV39 isolates (such as HPV39 L1 protein as set forth in No. P24838.1, ARQ82617.1, AGU90549.1 and AEP23084.1). Moreover, when a sequence fragment of a wild type HPV39 L1 protein is described, it includes not only the sequence fragment of SEQ ID NO: 1, but also the corresponding sequence fragment of a L1 protein of various HPV39 isolates. For example, the expression "amino acid residues at positions 53-61 of a wild type HPV39 L1 protein" includes the amino acid residues at positions 53-61 of SEQ ID NO: 1, and the corresponding fragment of a L1 protein of various HPV39 isolates.

According to the invention, the term "wild type HPV68 L1 protein" refers to the naturally-occurring major capsid protein L1 in Human Papillomavirus Type 68 (HPV68). The sequence of wild type HPV68 L1 protein is well known in the art, and can be found in public database (such as Accession No. AAZ39498.1, AGU90717.1, P4669.1 and AGU90703.1 in NCBI database).

In the invention, when an amino acid sequence of wild type HPV68 L1 protein is mentioned, it is described by reference to the sequence as set forth in SEQ ID NO: 2. For example, the expression "amino acid residues at positions 53-61 of a wild type HPV68 L1 protein" refers to the amino acid residues at positions 53-61 of the polypeptide as set forth in SEQ ID NO: 2. However, a person skilled in the art understands that wild type HPV68 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV68 isolates, and have substantively the same biological function. Therefore, in the invention, the term "wild type HPV68 L1 protein" includes not only the protein as set forth in SEQ ID NO: 2, but also L1 protein of various HPV68 isolates (such as HPV68 L1 protein as set forth in AAZ39498.1, AGU90717.1, P4669.1 and AGU90703.1). Moreover, when a sequence fragment of a wild type HPV68 L1 protein is described, it includes not only the sequence fragment of SEQ ID NO: 2, but also the corresponding sequence fragment of a L1 protein of various HPV68 isolates. For example, the expression "amino acid residues at positions 53-61 of a wild type HPV68 L1 protein" includes the amino acid residues at positions 53-61 of SEQ ID NO: 2, and the corresponding fragment of a L1 protein of various HPV68 isolates.

According to the invention, the term "wild type HPV70 L1 protein" refers to the naturally-occurring major capsid protein L1 in Human Papillomavirus Type 70 (HPV70). The sequence of wild type HPV70 L1 protein is well known in the art, and can be found in public database (such as Accession No. AGU90846.1, AGU90854.1, AAC54879.1 and P50793.1 in NCBI database).

In the invention, when an amino acid sequence of wild type HPV70 L1 protein is mentioned, it is described by reference to the sequence as set forth in SEQ ID NO: 3. For example, the expression "amino acid residues at positions 117-141 of a wild type HPV70 L1 protein" refers to amino acid residues at positions 117-141 of the polypeptide as set forth in SEQ ID NO: 3. However, a person skilled in the art understands that wild type HPV70 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV70 isolates, and have substantively the same biological function. Therefore, in the invention, the term "wild type HPV70 L1 protein" includes not only the protein as set forth in SEQ ID NO: 3, but also L1 protein of various HPV70 isolates (such as HPV70 L1 protein as set forth in AGU90846.1, AGU90854.1, AAC54879.1 and P50793.1). Moreover, when a sequence fragment of a wild type HPV70 L1 protein is described, it includes not only the sequence fragment of SEQ ID NO: 3, but also the corresponding sequence fragment of L1 protein of various HPV70 isolates. For example, the expression "amino acid residues at positions 117-141 of a wild type HPV70 L1 protein" includes the amino acid residues at positions 117-141 of SEQ ID NO: 3, and the corresponding fragment of L1 protein of various HPV70 isolates.

According to the invention, the expression "corresponding sequence fragments" or "corresponding fragments" refers to the fragments that are located at equivalent positions of the sequences being compared when the sequences are optimally aligned, i.e. the sequences are aligned to obtain a highest percentage of identity.

According to the invention, the expression "N-terminal truncation of X amino acids" or "having X amino acids truncated at N-terminal" refers to substitution of the amino acid residues from positions 1 to X at the N-terminal of a protein with methionine residue encoded by an initiator codon (for initiating protein translation). For example, a HPV39 L1 protein having 15 amino acids truncated at N-terminal refers to a protein resulted from substituting the amino acid residues from positions 1 to 15 at the N-terminal of wild type HPV39 L1 protein with methionine residue encoded by an initiator codon.

According to the invention, the term "variant" refers to a protein, whose amino acid sequence has substitution (preferably conservative substitution), addition or deletion of one or more (e.g. 1, 2, 3, 4, 5, 6, 7, 8 or 9) amino acids, or has an identity of at least 90%, 95%, 96%, 97%, 98%, or 99%, as compared with the mutated HPV39 L1 protein according to the invention (for example, the protein as set forth in SEQ ID NO: 7, 10, 11 or 12), and which retains a function of the mutated HPV39 L1 protein according to the invention. In the invention, the term "function of the mutated HPV39 L1 protein" refers to a capability of inducing generation of neutralizing antibodies against at least two HPV types (e.g. HPV39 and HPV68, or HPV39, HPV68 and HPV70). The term "identity" refers to a measure of similarity between nucleotide sequences or amino acid sequences. Generally, sequences were aligned to obtain a maximum matching.

"Identity" has well-known meanings in the art and can be calculated by published algorithm (such as BLAST).

According to the invention, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6 or 4 and a length weight of 1, 2, 3, 4, 5 or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, and tryptophan), amino acids having nonpolar side chains (for example, alanine, valine, leucine, isoleucine, proline, phenylalanine, and methionine), amino acids having β-branched side chains (such as threonine, valine, and isoleucine) and amino acids having aromatic side chains (for example, tyrosine, phenylalanine, tryptophan, and histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the invention, the term "E. coli expression system" refers to an expression system consisting of E. coli (strain) and a vector, wherein the E. coli (strain) is derived from the commercially available strains, including, but not limited to: ER2566, BL21 (DE3), B834 (DE3), and BLR (DE3).

According to the invention, the term "vector" refers to a nucleic acid carrier tool which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, etc.

According to the invention, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro Ark., 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants, e.g., Tween-80; adjuvants include, but are not limited to, aluminium adjuvant (e.g., aluminium hydroxide), and Freund's adjuvant (e.g., Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (such as cation-exchange chromatography), hydrophobic interaction chromatography, absorbent chromatography (such as hydroxyapatite chromatography), gel filtration chromatography (gel exclusion chromatography), and affinity chromatography.

According to the invention, the term "lysate supernatant" refers to a solution produced by the following steps: host cells (such as E. coli) are disrupted in a lysis buffer, and the insoluble substances are then removed from the lysed solution containing the disrupted host cells. Various lysis buffers are well known in the art, including, but not limited to Tris buffers, phosphate buffers, HEPES buffers, MOPS buffers, etc. In addition, the disrupting of a host cell can be accomplished by methods well known by a person skilled in the art, including, but not limited to homogenizer disrupting, ultrasonic treatment, grinding, high pressure extrusion, lysozyme treatment, etc. Methods for removing insoluble substances are also well known by a person skilled in the art, including, but not limited to filtration and centrifugation.

Beneficial Effects of Invention

Studies show that although there is certain cross-protection between HPV39 and other HPV type(s) (such as HPV68 and HPV70), such cross-protection is very low, generally lower than one percent, even one thousandth of the protection level of VLP of the same HPV type. Therefore, a subject vaccinated with HPV39 vaccine, still has a high risk of being infected by other HPV type(s) (such as HPV68 and HPV70).

The invention provides a mutated HPV39 L1 protein and a HPV virus-like particle formed by the same. The HPV virus-like particle according to the invention can provide significant cross-protection against HPV39 and other HPV type(s) (such as HPV68 and HPV70). Especially, at the same immunizing dose, the HPV virus-like particle according to the invention can induce the generation of high-titer neutralizing antibodies against at least two HPV types (e.g. HPV39 and HPV68, or HPV39, HPV68 and HPV70) in organisms, and its effect is comparable to that of a mixture of VLPs of multiple HPV types (e.g. a mixture of HPV39 VLP and HPV68 VLP, or a mixture of HPV39 VLP, HPV68 VLP and HPV70 VLP). Therefore, the HPV virus-like particle according to the invention can be used to prevent infection by at least two HPV types (e.g. HPV39 and HPV68, or HPV39, HPV68 and HPV70) at the same time as well as diseases associated with the infection, and has significantly beneficial technical effects. This has particularly significant advantages in terms of extending the protection range of HPV vaccines and reducing the production cost of HPV vaccines.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF DRAWINGS

FIG. 5A, HPV39N15 VLP; FIG. 5B, HPV68L1N0 VLP; FIG. 5C, H39N15-68T1 VLP; FIG. 5D, H39N15-68T2 VLP; FIG. 5E, H39N15-68T3 VLP; FIG. 5F, H39N15-68T4 VLP; FIG. 5G, H39N15-68T5 VLP; FIG. 5H, HPV70N10 VLP; FIG. 5I, H39N15-68T4-70S1 VLP; FIG. 5J, H39N15-68T4-70S2 VLP; FIG. 5K, H39N15-68T4-70S3 VLP; FIG. 5L, H39N15-68T4-70S5 VLP. The results showed that the sedimentation coefficients of H39N15-68T1 VLP, H39N15-68T2 VLP, H39N15-68T3 VLP, H39N15-68T4 VLP, H39N15-68T5 VLP, H39N15-68T4-70S1 VLP, H39N15-68T4-70S2 VLP, H39N15-68T4-70S3 VLP and H39N15-68T4-70S5 VLP were 136S, 151S, 138S, 145S, 135S, 124S, 108S, 99S and 127S, respectively. This showed that the mutated protein H39N15-68T1, H39N15-68T2, H39N15-68T3, H39N15-68T4, H39N15-68T5, H39N15-68T4-70S1, H39N15-68T4-70S2, H39N15-68T4-70S3 and H39N15-68T4-70S5 were able to assemble into virus-like particles that were similar to wild type VLP (HPV39N15 VLP, 115S; HPV68N0 VLP, 153S; HPV70N10 VLP, 144S) in terms of size and morphology.

FIG. 6A, VLP assembled by HPV39N15; FIG. 6B, VLP assembled by HPV68L1N0; FIG. 6C, VLP assembled by HPV70N10; FIG. 6D, VLP assembled by H39N15-68T1; FIG. 6E, VLP assembled by H39N15-68T2; FIG. 6F, VLP assembled by H39N15-68T3; FIG. 6G, VLP assembled by H39N15-68T4; FIG. 6H, VLP assembled by H39N15-68T5; FIG. 6I, VLP assembled by H39N15-68T4-70S1; FIG. 6J, VLP assembled by H39N15-68T4-70S2; FIG. 6K, VLP assembled by H39N15-68T4-70S3; FIG. 6L, VLP assembled by H39N15-68T4-70S5. The results showed that H39N15-68T1, H39N15-68T2, H39N15-68T3, H39N15-68T4, H39N15-

68T5, H39N15-68T4-70S1, H39N15-68T4-70S2, H39N15-68T4-70S3, and H39N15-68T4-70S5 were similar to HPV39N15, HPV68L1N0 and HPV70N10, and were able to assemble into VLPs with a radius of about 25-30 nm.

Figure 7A:
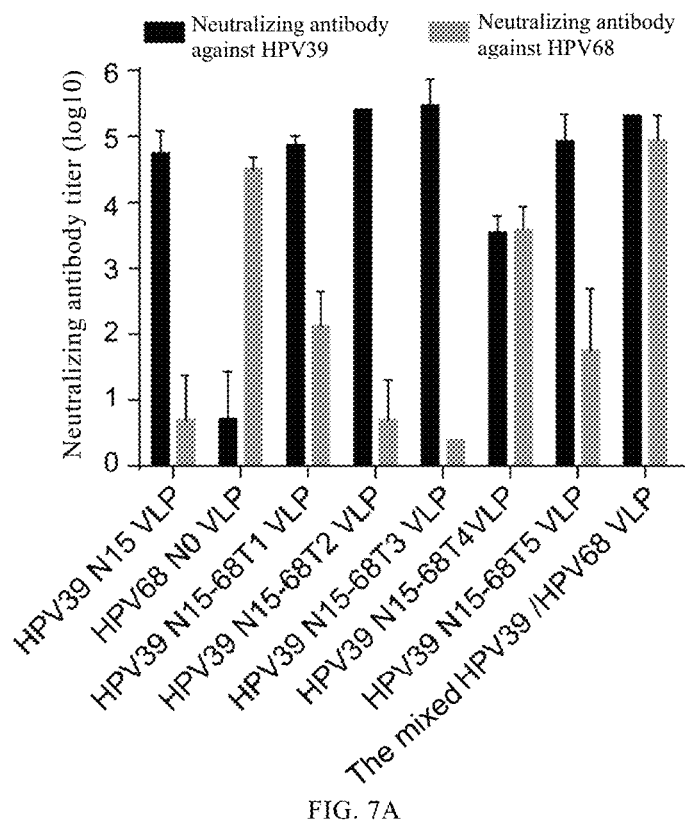
Figure 7B:
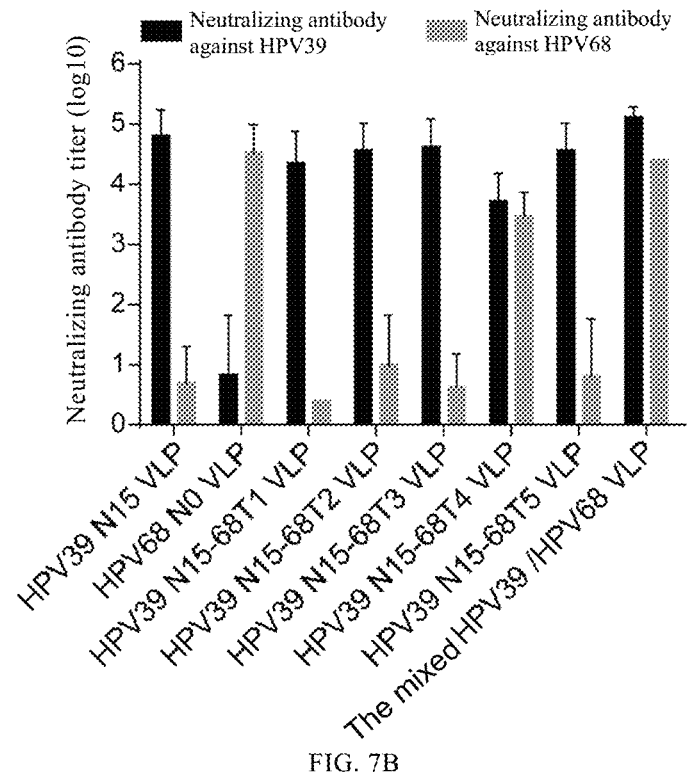
Figure 7C:
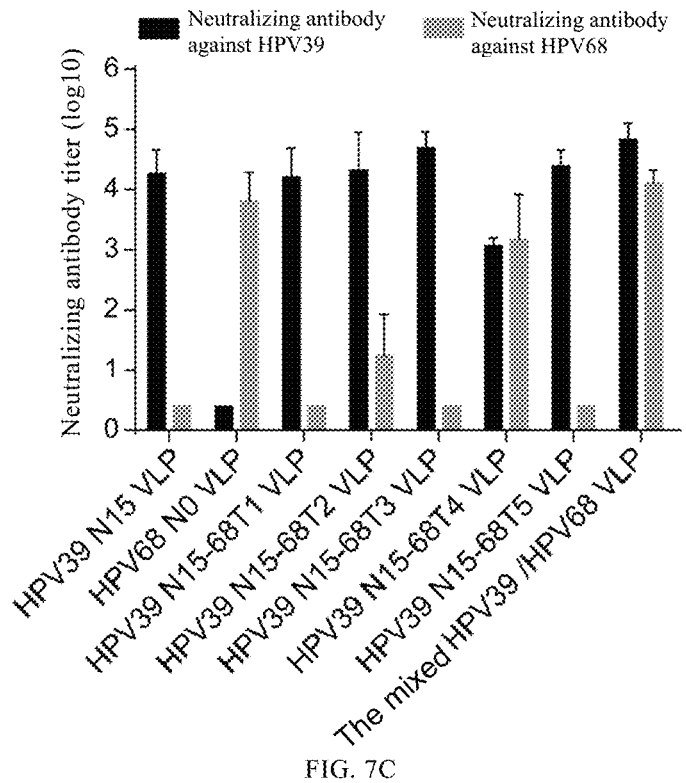

FIGS. 7A-7C show the result of neutralizing antibody titer in mouse serum after vaccination of mice with H39N15-68T1 VLP, H39N15-68T2 VLP, H39N15-68T3 VLP, H39N15-68T4 VLP, or H39N15-68T5 VLP. FIG. 7A: Aluminum adjuvant group 1 (at an immunizing dose of 5 μg, using aluminum adjuvant); FIG. 7B: Aluminum adjuvant group 2 (at an immunizing dose of 1 μg, using aluminum adjuvant); FIG. 7C: Aluminum adjuvant group 3 (at an immunizing dose of 0.2 μg, using aluminum adjuvant). The result showed that H39N15-68T4 VLP could induce the generation of high-titer neutralizing antibodies against HPV39 in mice, and its protective effect was slightly weaker than that of HPV39N15 VLP alone at the same dose, but was significantly superior to that of HPV68N0 VLP alone at the same dose; and it could induce the generation of high-titer neutralizing antibodies against HPV68 in mice, and its protective effect was slightly weaker than that of HPV68N0 VLP alone at the same dose, but was significantly superior to that of HPV39N15 VLP alone at the same dose. This showed that H39N15-68T4 VLP had good cross-immunogenicity and cross-protection against HPV39 and HPV68.

Figure 8A:
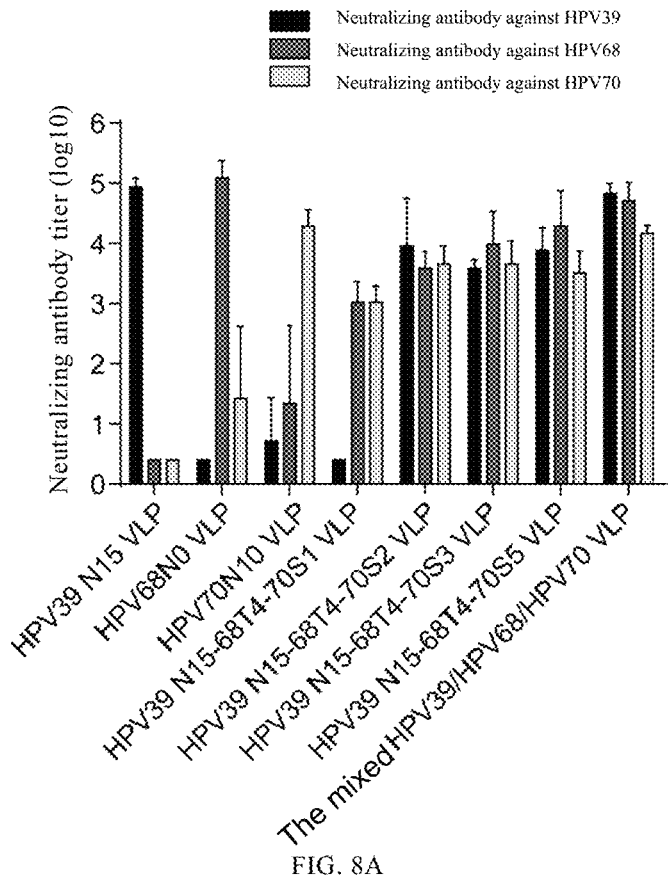
Figure 8B:
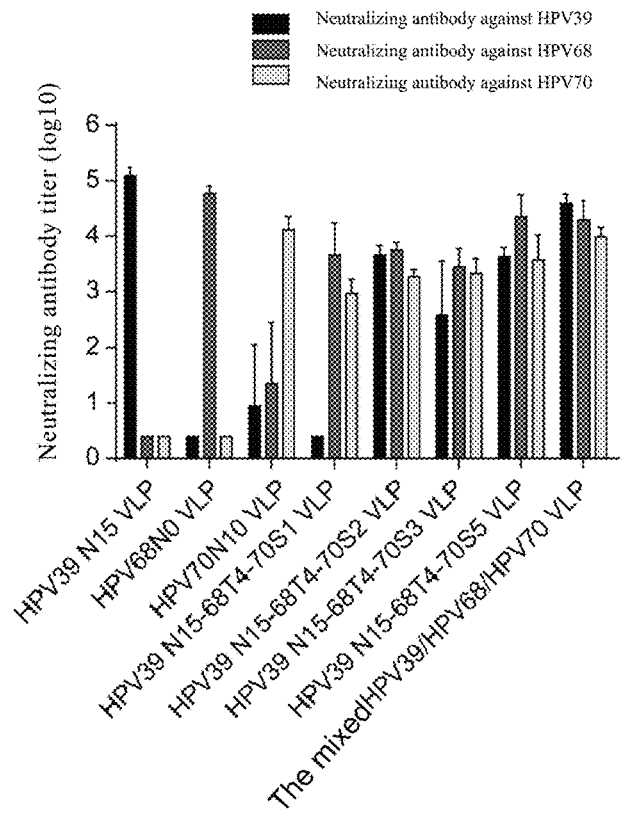
Figure 8C:
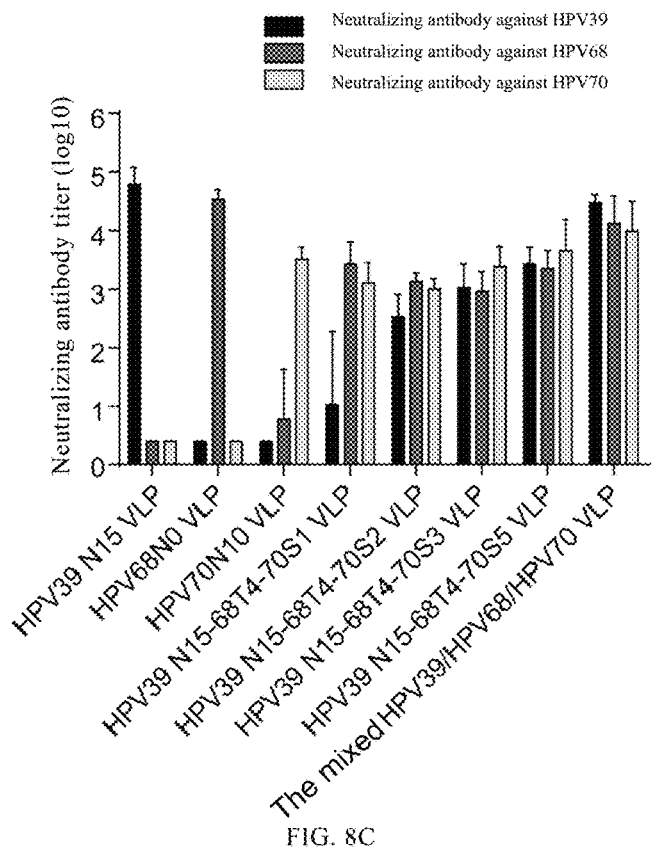

FIGS. 8A-8C show the result of neutralizing antibody titer in mouse serum after vaccination of mice with H39N15-68T4-70S1 VLP, H39N15-68T4-70S2 VLP, H39N15-68T4-70S3 VLP, and H39N15-68T4-70S5 VLP. FIG. 8A: Aluminum adjuvant group 1 (at an immunizing dose of 5 gig, using aluminum adjuvant); FIG. 8B: Aluminum adjuvant group 2 (at an immunizing dose of 1 gig, using aluminum adjuvant); FIG. 8C: Aluminum adjuvant group 3 (at an immunizing dose of 0.2 gig, using aluminum adjuvant). The result showed that H39N15-68T4-70S2, H39N15-68T4-70S3, and H39N15-68T4-70S5 VLP could induce the generation of high-titer neutralizing antibodies against HPV39 in mice, and their protective effects were slightly weaker than that of HPV39N15 VLP alone and that of the mixed HPV39/HPV68/HPV70 VLP at the same dose, but was significantly superior to that of HPV68N0 VLP alone and that of HPV70N10 VLP alone at the same dose; and they could induce the generation of high-titer neutralizing antibodies against HPV68 in mice, and their protective effects were comparable to that of HPV68N0 VLP alone and that of the mixed HPV39/HPV68/HPV70 VLP at the same dose, and was significantly superior to that of HPV39N15 VLP alone and that of HPV70N10 VLP alone at the same dose; and they could induce the generation of high-titer neutralizing antibodies against HPV70 in mice, and their protective effects were comparable to that of HPV70N10 VLP alone and that of the mixed HPV39/HPV68/HPV70 VLP at the same dose, and was significantly superior to that of HPV39N15 VLP alone and that of HPV68N0 VLP alone at the same dose. This showed that H39N15-68T4-70S2 VLP, H39N15-68T4-70S3 VLP and H39N15-68T4-70S5 VLP had good cross-immunogenicity and cross-protection against HPV39, HPV68 and HPV70.

Figure 9:
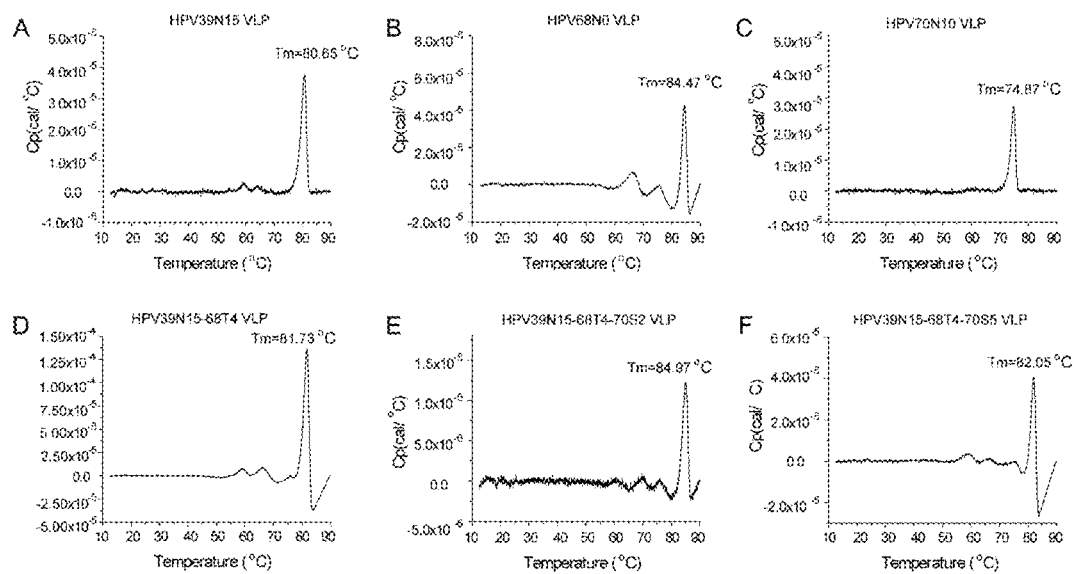

FIG. 9 shows the detection results of thermostability of HPV39N15 VLP, HPV68N0 VLP, HPV70N10 VLP, H39N15-68T4 VLP, H39N15-68T4-70S2 VLP, and H39N15-68T4-70S5 VLP, wherein A shows the detection results of thermostability of HPV39N15 VLP; B shows the detection results of thermostability of HPV68L1N0 VLP; C shows the detection results of thermostability of HPV70N10 VLP; D shows the detection results of thermostability of H39N15-68T4 VLP VLP; E shows the detection results of thermostability of H39N15-68T4-70S2 VLP; F shows the detection results of thermostability of H39N15-68T4-70S5 VLP. The results showed that all the VLPs formed by these proteins had very high thermostability.

Figure 10:
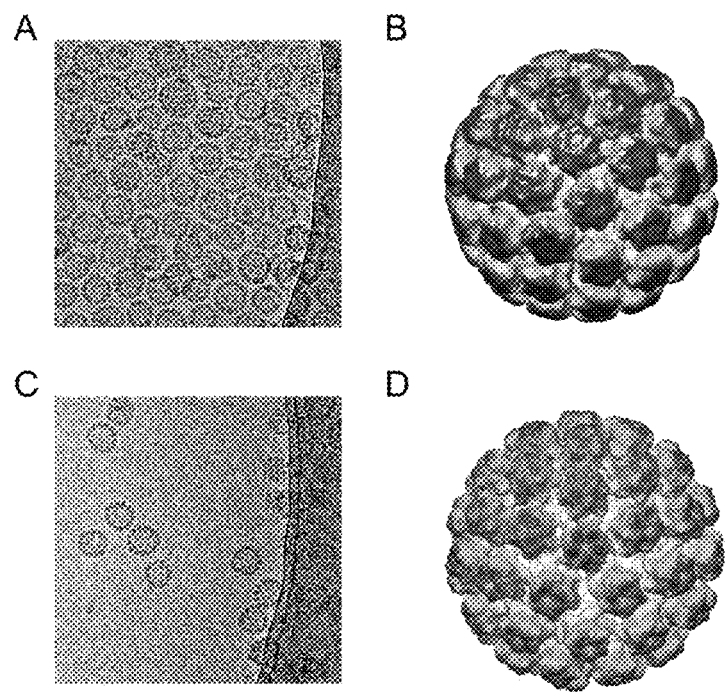

FIG. 10 shows the cryo-electron microscopy (cryo-EM) photographs and the reconstructed three-dimensional structures of H39N15-68T4-70S2 VLP and H39N15-68T4-70S5 VLP, wherein A shows the cryo-electron microscopy (cryo-EM) photograph of H39N15-68T4-70S2 VLP; B shows the reconstructed three-dimensional structure of H39N15-68T4-70S2 VLP; C shows the cryo-electron microscopy (cryo-EM) photograph of H39N15-68T4-70S5 VLP; D shows the reconstructed three-dimensional structure of H39N15-68T4-70S5 VLP. The reconstructed three-dimensional structures showed that both H39N15-68T4-70S2 VLP and H39N15-68T4-70S5 VLP had a T=7 icosahedral structure (h=1, k=2) consisting of 72 capsomers (morphological subunit, pentamer). Unlike conventional icosahedral viral capsids consistent with quasi-equivalence principle, all the constitutive subunits in the structures of H39N15-68T4-70S2 VLP and H39N15-68T4-70S5 VLP were pentamers, without hexamer. Moreover, said two VLPs had an external diameter of about 55 nm. These were similar to the three-dimensional structures of the previously reported natural HPV viral particles and the HPV VLP prepared by eukaryotic expression system (e.g. poxvirus expression system) (Baker T S, Newcomb W W, Olson N H. et al. Biophys J. (1991), 60(6): 1445-1456. Hagensee M E, Olson N H, Baker T S, et al. J Virol. (1994), 68(7):4503-4505. Buck C B, Cheng N, Thompson C D. et al. J Virol. (2008), 82(11): 5190-7).

SEQUENCE INFORMATION

Some of the sequences involved in the invention are provided in the following Table 1.

TABLE 1

| SEQ ID NO: | Description |
|---|---|
| 1 | wild type HPV39 L1 protein |
| 2 | wild type HPV68 L1 protein, HPV68N0 |
| 3 | wild type HPV70 L1 protein |
| 4 | the mutated HPV39 L1 protein comprising Segment 1 of HPV68 L1 protein, H39N15-68T1 |

TABLE 1 -continued

| Description of sequences | |
|---|---|
| SEQ ID NO: | Description |
| 5 | the mutated HPV39 L1 protein comprising Segment 2 of HPV68 L1 protein, H39N15-68T2 |
| 6 | the mutated HPV39 L1 protein comprising Segment 3 of HPV68 L1 protein, H39N15-68T3 |
| 7 | the mutated HPV39 L1 protein comprising Segment 4 of HPV68 L1 protein, H39N15-68T4 |
| 8 | the mutated HPV39 L1 protein comprising Segment 5 of HPV68 L1 protein, H39N15-68T5 |
| 9 | the mutated HPV39 L1 protein comprising Segment 4 of HPV68 L1 protein and Segment 1 of HPV70 L1 protein, H39N15-68T4-70S1 |
| 10 | the mutated HPV39 L1 protein comprising Segment 4 of HPV68 L1 protein and Segment 2 of HPV70 L1 protein, H39N15-68T4-70S2 |
| 11 | the mutated HPV39 L1 protein comprising Segment 4 of HPV68 L1 protein and Segment 3 of HPV70 L1 protein, H39N15-68T4-70S3 |
| 12 | the mutated HPV39 L1 protein comprising Segment 4 of HPV68 L1 protein and Segment 5 of HPV70 L1 protein, H39N15-68T4-70S5 |
| 13 | the DNA sequence encoding SEQ ID NO: 1 |
| 14 | the DNA sequence encoding SEQ ID NO: 2 |
| 15 | the DNA sequence encoding SEQ ID NO: 3 |
| 16 | the DNA sequence encoding SEQ ID NO: 4 |
| 17 | the DNA sequence encoding SEQ ID NO: 5 |
| 18 | the DNA sequence encoding SEQ ID NO: 6 |
| 19 | the DNA sequence encoding SEQ ID NO: 7 |
| 20 | the DNA sequence encoding SEQ ID NO: 8 |
| 21 | the DNA sequence encoding SEQ ID NO: 9 |
| 22 | the DNA sequence encoding SEQ ID NO: 10 |
| 23 | the DNA sequence encoding SEQ ID NO: 11 |
| 24 | the DNA sequence encoding SEQ ID NO: 12 |
| 25 | the sequence of the amino acid residues at positions 270-289 of wild type HPV68 L1 protein, i.e., Segment 4 of HPV68 L1 protein |
| 26 | the sequence of the amino acid residues at positions 117-141 of wild type HPV70 L1 protein, i.e., Segment 2 of HPV70 L1 protein |
| 27 | the sequence of the amino acid residues at positions 170-182 of wild type HPV70 L1 protein, i.e., Segment 3 of HPV70 L1 protein |
| 28 | the sequence of the amino acid residues at positions 348-359 of wild type HPV70 L1 protein, i.e., Segment 5 of HPV70 L1 protein |
| 29 | the HPV39 L1 protein having 15 amino acids truncated at N-terminal, HPV39N15 |
| 30 | the DNA sequence encoding SEQ ID NO:29 |
| 31 | the HPV70 L1 protein having 10 amino acids truncated at N-terminal, HPV70N10 |
| 32 | the DNA sequence encoding SEQ ID NO:31 |
| 33 | the sequence of the amino acid residues at positions 53-61 of wild type HPV68 L1 protein, i.e., Segment 1 of HPV68 L1 protein |

TABLE 1 -continued

Description of sequences

SEQ ID NO: Description 34 the sequence of the amino acid residues at positions 117-151 of wild type HPV68 L1 protein, i.e., Segment 2 of HPV68 L1 protein 35 the sequence of the amino acid residues at positions 170-182 of wild type HPV68 L1 protein, i.e., Segment 3 of HPV68 L1 protein 36 the sequence of the amino acid residues at positions 348-359 of wild type HPV68 L1 protein, i.e., Segment 5 of HPV68 L1 protein 37 the sequence of the amino acid residues at positions 53-61 of wild type HPV70 L1 protein, i.e., Segment 1 of HPV70 L1 protein

```
Sequence 1 (SEQ ID NO: 1):
MALWRSSDSMVYLPPPSVAKVVNTDDYVTRTGIYYYAGSSRLLTVGHPYFKVGMNGGRKQDIPKVS
AYQYRVFRVTLPDPNKFSIPDASLYNPETQRLVWACVGVEVGRGQPLGVGISGHPLYNRQDDTENSP
FSSTTNKDSRDNVSVDYKQTQLCIIGCVPAIGEHWGKGKACKPNNVSTGDCPPLELVNTMEDGDMID
TGYGAMDFGALQETKSEVPLDICQSICKYPDYLQMSADVYGDSNIFFCLRREQLFARHFWNRGGMVG
DAIPAQLYIKGTDIRANPGSSVYCPSPSGSMVTSDSQLFNKPYWLHKAQGHNNGICWHNQLFLTVVD
TTRSTNFTLSTSIESSIPSTYDPSKFKEYTRHVEEYDLQFIFQLCTVTLTTDVMSYIHTMNSSILDNWNF
AVAPPPSASLVDTYRYLQSAAITCQKDAPAPEKKDPYDGLKFWNVDLREKFSLELDQFPLGRKFLLQ
ARVRRRPTIGPRKRPAASTSSSSATKHKRKRVSK
Sequence 2 (SEQ ID NO: 2):
MALWRASDNMVYLPPPSVAKVVNTDDYVTRTGMYYYAGTSRLLTVGHPYFKVPMSGGRKQGIPKV
SAYQYRVFRVTLPDPNKFSVPESTLYNPDTQRMVWACVGVEIGRGQPLGVGLSGHPLYNRLDDTENS
PFSSNKNPKDSRDNVAVDCKQTQLCIIGCVPAIGEHWAKGKSCKPTNVQQGDCPPLELVNTMEDGD
MIDTGYGAMDFGTLQETKSEVPLDICQSVCKYPDYLQMSADVYGDSMFFCLRREQLFARHFWNRGG
MVGDTIPTDMYIKGTDIRETPSSYVYAPSPSGSMVSSDSQLFNKPYWLHKAQGHNNGICWHNQLFLT
VVDTTRSTNFTLSTTTDSTVPAVYDSNKFKEYVRHVEEYDLQFIFQLCTITLSTDVMSYIHTMNPAILD
DWNFGVAPPPSASLVDTYRYLQSAAITCQKDAPAPVKKDPYDGLNFWNVDLKEKFSSELDQFPLGRK
FLLQAGVRRRPTIGPRKRTATAATTSTSKHKRKRVSK
Sequence 3 (SEQ ID NO: 3):
MALWRSSDNTVYLPPPSVAKVVNTDDYVTRTGIYYYAGSSRLLTVGHPYFKVPVNGGRKQEIPKVSA
YQYRVFRVSLPDPNKFGLPDPSLYNPDTQRLVWACIGVEIGRGQPLGVGVSGHPLYNRLDDTENSHFS
SAVNTQDSRDNVSVDYKQTQLCIIGCVPAMGEHWAKGKACKSTTVQQGDCPPLELVNTAIEDGDMI
DTGYGAMDFRTLQETKSEVPLDICQSVCKYPDYLQMSADVYGDSMFFCLRKEQLFARHFWNRGGM
VGDTIPSELYIKGTDIRDRPGTHVYSPSPSGSMVSSDSQLFNKPYWLHKAQGHNNGICWHNQLFITVV
DTTRSTNFTLSACTETAIPAVYSPTKFKEYTRHVEEYDLQFIFQLCTITLTADVMAYIHTMNPAILDNW
NIGVTPPPSASLVDTYRYLQSAAIACQKDAPAPEKKDPYDDLKFWNVDLKEKFSTELDQFPLGRKFLL
QVGARRRPTIGPRKRPASAKSSSSASKHKRKRVSK
Sequence 4 (SEQ ID NO: 4):
NIPSVAKVVNTDDYVTRTGIYYYAGSSRLLTVGHPYFKVPMSGGRKQGIPKVSAYQYRVFRVTLPDP
NKFSIPDASLYNPETQRLVWACVGVEVGRGQPLGVGISGHPLYNRQDDTENSPFSSTTNKDSRDNVS
VDYKQTQLCIIGCVPAIGEHWGKGKACKPNNVSTGDCPPLELVNTPIEDGDMIDTGYGAMDFGALQE
TKSEVPLDICQSICKYPDYLQMSADVYGDSMFFCLRREQLFARHFWNRGGMVGDAIPAQLYIKGTDI
RANPGSSVYCPSPSGSMVTSDSQLFNKPYWLIIKAQGHNNGICWHNQLFLTVVDTTRSTNFTLSTSIES
SIPSTYDPSKFKEYTRHVEEYDLQFIFQLCTVTLTTDVMSYIHTMNSSILDNWNFAVAPPPSASLVDTY
RYLQSAAITCQKDAPAPEKKDPYDGLKFWNVDLREKFSLELDQFPLGRKFLLQARVRRRPTIGPRKRP
AASTSSSSATKHKRKRVSK
Sequence 5 (SEQ ID NO: 5):
NIPSVAKVVNTDDYVTRTGIYYYAGSSRLLTVGHPYFKVGMNGGRKQDIPKVSAYQYRVFRVTLPDP
NKFSIPDASLYNPETQRL VWACVGVEVGRGQPLGVGLSGHPLYNRLDDTENSPFSSNKNPKDSRDNV
AVDCKQTQLCIIGCVPAIGEHWGKGKACKPNNVSTGDCPPLELVNTPIEDGDMIDTGYGAMDFGALQ
ETKSEVPLDICQSICKYPDYLQMSADVYGDSMFFCLRREQLFARHFWNRGGMVGDAIPAQLYIKGTD
IRANPGSSVYCPSPSGSMVTSDSQLFNKPYWLIIKAQGHNNGICWHNQLFLTVVDTTRSTNFTLSTSIE
SSIPSTYDPSKFKEYTRHVEEYDLQFIFQLCTVTLTTDVMSYIHTMNSSILDNWNFAVAPPPSASLVDT
YRYLQSAAITCQKDAPAPEKKDPYDGLKFWNVDLREKFSLELDQFPLGRKFLLQARVRRRPTIGPRK
RPAASTSSSSATKHKRKRVSK
Sequence 6 (SEQ ID NO: 6):
NIP SVAKVVNTDDYVTRTGIYYYAGSSRLLTVGHPYFKVGMNGGRKQDIPKVSAYQYRVFRVTLPDP
NKFSIPDASLYNPETQRLVWACVGVEVGRGQPLGVGISGHPLYNRQDDTENSPFSSTTNKDSRDNVS
VDYKQTQLCIIGCVPAIGEHWAKGKSCKPTNVQQGDCPPLELVNTPIEDGDMIDTGYGAMDFGALQE
TKSEVPLDICQSICKYPDYLQMSADVYGDSMFFCLRREQLFARHFWNRGGMVGDAIPAQLYIKGTDI
RANPGSSVYCPSPSGSMVTSDSQLFNKPYWLIIKAQGHNNGICWHNQLFLTVVDTTRSTNFTLSTSIES
SIPSTYDPSKFKEYTRHVEEYDLQFIFQLCTVTLTTDVMSYIHTMNSSILDNWNFAVAPPPSASLVDTY
RYLQ SAAITCQKDAPAPEKKDPYDGLKFWNVDLREKFSLELDQFPLGRKFLLQARVRRRPTIGPRKRP
AASTSSSSATKHKRKRVSK
Sequence 7 (SEQ ID NO: 7):
NIPSVAKVVNTDDYVTRTGIYYYAGSSRLLTVGHPYFKVGMNGGRKQDIPKVSAYQYRVFRVTLPDP
NKFSIPDASLYNPETQRLVWACVGVEVGRGQPLGVGISGHPLYNRQDDTENSPFSSTTNKDSRDNVS
VDYKQTQLCIIGCVPAIGEHWGKGKACKPNNVSTGDCPPLELVNTPIEDGDMIDTGYGAMDFGALQE
TKSEVPLDICQSICKYPDYLQMSADVYGDSMFFCLRREQLFARHFWNRGGMVGDTIPTDMYIKGTDI
RETPSSYVYCPSPSGSMVTSDSQLFNKPYWLHKAQGHNNGICWHNQLFLTVVDTTRSTNFTLSTSIES
SIPSTYDPSKFKEYTRHVEEYDLQFIFQLCTVTLTTDVMSYIHTMNSSILDNWNFAVAPPPSASLVDTY
```

TABLE 1 -continued

Description of sequences

SEQ ID NO: Description

RYLQSAAITCQKDAPAPEKKDPYDGLKFWNVDLREKFSLELDQFPLGRKFLLQARVRRRPTIGPRKRP
AASTSSSSATKHKRKRVSK
Sequence 8 (SEQ ID NO: 8):
NIPSVAKVVNTDDYVTRTGIYYYAGSSRLLTVGHPYFKVGMNGGRKQDIPKVSAYQYRVFRVTLPDP
NKFSIPDASLYNPETQRLVWACVGVEVGRGQPLGVGISGHPLYNRQDDTENSPFSSTTNKDSRDNVS
VDYKQTQLCIIGCVPAIGEHWGKGKACKPNNVSTGDCPPLELVNTPIEDGDMIDTGYGAMDFGALQE
TKSEVPLDICQSICKYPDYLQMSADVYGDSMFFCLRREQLFARHFWNRGGMVGDAIPAQLYIKGTDI
RANPGSSVYCPSPSGSMVTSDSQLFNKPYWLHKAQGHNNGICWHNQLFLTVVDTTRSTNFTLSTSTD
STVPAVYDSNKFKEYTRHVEEYDLQFIFQLCTVTLTTDVMSYIHTMNSSILDNWNFAVAPPPSASLVD
TYRYLQSAAITCQKDAPAPEKKDPYDGLKFWNVDLREKFSLELDQFPLGRKFLLQARVRRRPTIGPRK
RPAASTSSSSATKHKRKRVSK
Sequence 9 (SEQ ID NO: 9):
NIPSVAKVVNTDDYVTRTGIYYYAGSSRLLTVGHPYFKVPVNGGRKQEIPKVSAYQYRVFRVTLPDPN
KFSIPDASLYNPETQRLVWACVGVEVGRGQPLGVGISGHPLYNRQDDTENSPFSSTTNKDSRDNVSV
DYKQTQLCIIGCVPAIGEHWGKGKACKPNNVSTGDCPPLELVNTPIEDGDMIDTGYGAMDFGALQET
KSEVPLDICQSICKYPDYLQMSADVYGDSMFFCLRREQLFARHFWNRGGMVGDTIPTDMYIKGTDIR
ETPSSYVYCPSPSGSMVTSDSQLFNKPYWLIIKAQGHNNGICWHNQLFLTVVDTTRSTNFTLSTSIESSI
PSTYDPSKFKEYTRHVEEYDLQFIFQLCTVTLTTDVMSYIHTMNSSILDNWNFAVAPPPSASLVDTYR
YLQSAAITCQKDAPAPEKKDPYDGLKFWNVDLREKFSLELDQFPLGRKFLLQARVRRRPTIGPRKRPA
ASTSSSSATKHKRKRVSK
Sequence 10 (SEQ ID NO: 10):
NIPSVAKVVNTDDYVTRTGIYYYAGSSRLLTVGHPYFKVGMNGGRKQDIPKVSAYQYRVFRVTLPDP
NKFSIPDASLYNPETQRLVWACVGVEVGRGQPLGVGVSGHPLYNRLDDTENSHFSSAVNTQDSRDN
VSVDYKQTQLCIIGCVPAIGEHWGKGKACKPNNVSTGDCPPLELVNTPIEDGDMIDTGYGAMDFGAL
QETKSEVPLDICQSICKYPDYLQMSADVYGDSNIFFCLRREQLFARHFWNRGGMVGDTIPTDMYIKGT
DIRETPSSYVYCPSPSGSMVTSDSQLFNKPYWLIIKAQGHNNGICWHNQLFLTVVDTTRSTNFTLSTSI
ESSIPSTYDPSKFKEYTRHVEEYDLQFIFQLCTVTLTTDVMSYIHTMNSSILDNWNFAVAPPPSASLVD
TYRYLQSAAITCQKDAPAPEKKDPYDGLKFWNVDLREKFSLELDQFPLGRKFLLQARVRRRPTIGPRK
RPAASTSSSSATKHKRKRVSK
Sequence 11 (SEQ ID NO: 11):
NIPSVAKVVNTDDYVTRTGIYYYAGSSRLLTVGHPYFKVGMNGGRKQDIPKVSAYQYRVFRVTLPDP
NKFSIPDASLYNPETQRLVWACVGVEVGRGQPLGVGISGHPLYNRQDDTENSPFSSTTNKDSRDNVS
VDYKQTQLCIIGCVPAIGEHWAKGKACKSTTVQQGDCPPLELVNTPIEDGDMIDTGYGAMDFGALQE
TKSEVPLDICQSICKYPDYLQMSADVYGDSMFFCLRREQLFARHFWNRGGMVGDTIPTDMYIKGTDI
RETPSSYVYCPSPSGSMVTSDSQLFNKPYWLHKAQGHNNGICWHNQLFLTVVDTTRSTNFTSTSIES
SIPSTYDPSKFKEYTRHVEEYDLQFIFQLCTVTLTTDVMSYIHTMNSSILDNWNFAVAPPPSASLVDTY
RYLQSAAITCQKDAPAPEKKDPYDGLKFWNVDLREKFSLELDQFPLGRKFLLQARVRRRPTIGPRKRP
AASTSSSSATKHKRKRVSK
Sequence 12 (SEQ ID NO: 12):
NIPSVAKVVNTDDYVTRTGIYYYAGSSRLLTVGHPYFKVGMNGGRKQDIPKVSAYQYRVFRVTLPDP
NKFSIPDASLYNPETQRLVWACVGVEVGRGQPLGVGISGHPLYNRQDDTENSPFSSTTNKDSRDNVS
VDYKQTQLCIIGCVPAIGEHWGKGKACKPNNVSTGDCPPLELVNTPIEDGDMIDTGYGAMDFGALQE
TKSEVPLDICQSICKYPDYLQMSADVYGDSMFFCLRREQLFARHFWNRGGMVGDTIPTDMYIKGTDI
RETPSSYVYCPSPSGSMVTSDSQLFNKPYWLHKAQGHNNGICWHNQLFLTVVDTTRSTNFTLSTSTET
AIPAVYSPTKFKEYTRHVEEYDLQFIFQLCTVTLTTDVMSYIHTMNSSILDNWNFAVAPPPSASLVDTY
RYLQSAAITCQKDAPAPEKKDPYDGLKFWNVDLREKFSLELDQFPLGRKFLLQARVRRRPTIGPRKRP
AASTSSSSATKHKRKRVSK
Sequence 13 (SEQ ID NO: 13):
ATGGCCCTCTGGCGCAGCTCCGATTCCATGGTCTACCTCCCCCCCCCCAGCGTCGCCAAGGTCGT
GAACACCGACGACTACGTCACCCGCACCGGGATCTACTACTACGCGGGTCTCAGCCGCCTGCTGA
CCGTGGGCCACCCCTACTTCAAGGTCGGCATGAACGGCGGGCGCAAGCAGGATATCCCCAAGGT
CAGCGCCTACCAGTACCGCGTGTTCCGCGTCACCCTCCCAGACCCCAACAAGTTCTCCATCCCCG
ACGCCAGCCTGTACAACCCCGAGACCCAGCGCCTGGTGTGGGCCTGCGTGGGCGTCGAAGTCGG
GCGCGGGCAGCCCCTCGGCGTCGGCATCTCCGGCCACCCCCTGTACAACCGCCAGGACGACACC
GAGAATAGCCCCTTCAGCAGCACAACAAACAAGGATTCCCGCGACAACGTCAGCGTCGACTACA
AGCAGACCCAGCTCTGTATCATCGGGTGCGTCCCAGCAATCGGCGAACACTGGGGCAAGGGCAA
GGCCTGTAAGCCAAACAACGTGAGCACCGGCGATTGCCCCCCCCTGGAGCTGGTGAATACACCC
ATCGAAGACGGCGACATGATCGACACCGGGTACGGCGCCATGGATTTCGGCGCCCTCCAGGAGA
CAAAGTCCGAAGTCCCCCTGGACATCTGCCAGAGCATCTGCAAGTACCCCGACTACCTCCAGATG
AGCGCCGACGTCTACGGCGATTCCATGTTCTTCTGCCTGCGCCGCGAGCAGCTCTTCGCCCGCCA
CTTCTGGAACCGCGGCGGCATGGTCGGCGATGCAATCCCCGCACAGCTCTACATCAAGGGGACC
GACATCCGCGCCAATCCAGGCTCCAGCGTGTATTGTCCAAGCCCATCCGGCAGCATGGTGACAAG
CGACAGCCAGCTGTTCAACAAGCCCTACTGGCTGCACAAGGCACAGGGGCATAATAACGGCATC
TGCTGGCACAACCAGCTGTTCCTGACCGTCGTGATACCACACGCTCCACAAATTTCACCCTGAG
CACAAGCATCGAAAGCAGCATCCCCAGCACCTACGACCCCAGCAAGTTCAAGGAGTACACACGC
CACGTCGAAGAATACGACCTGCAGTTCATCTTCCAGCTCTGCACCGTGACCCTGACCACCGACGT
CATGAGCTACATCCACACCATGAACAGCAGCATCCTCGATAACTGGAACTTCGCCGTGGCCCCCC
CCCCCAGCGCATCCCTCGTGGATACCTATCGCTATCTGCAGAGCGCCGCAATCACCTGCCAGAAG
GACGCCCCCGCCCCCGAGAAGAAGGACCCCTACGATGGCCTGAAGTTCTGGAACGTCGATCTGC
GCGAGAAGTTCTCCCTGGAGCTGGACCAGTTCCCCCTCGGCCGCAAGTTCCTCCTCCAGGCACGC
GTGCGCCGCCGCCCCACCATCGGCCCACGCAAGCGCCCCGCCGCCAGCACCAGCAGCAGCAGCG
CCACCAAGCACAAGCGCAAGCGCGTCAGCAAGTGA
Sequence 14 (SEQ ID NO: 14):
ATGGCACTGTGGAGAGCAGCGACAACATGGTGTACCTGCCCCCTCCCAGCGTGGCCAAGGTGG
TCAACACCGACGACTACGTGACCCGGACCGGCATGTACTACTACGCCGGCACCTCTCGGCTCCTG TABLE 1-continued Description of sequences SEQ ID NO: Description ACCGTGGGCCACCCCTACTTCAAGGTGCCCATGAGCGGCGGCAGAAAGCAGGGCATCCCCAAGG
TGTCCGCCTACCAGTACCGGGTGTTCAGAGTGACCCTGCCCGACCCCAACAAGTTCAGCGTGCCC
GAGAGCACCCTGTACAACCCCGACACCCAGCGGATGGTCTGGGCCTGCGTGGGCGTGGAGATCG
GCAGAGGCCAGCCCCTGGGCGTGGGCCTGAGCGGCCACCCCCTGTACAATCGGCTGGACGACAC
CGAGAACAGCCCCTTCAGCAGCAACAAGAACCCCAAGGACAGCCGGGACAACGTGGCCGTGGA
CTGCAAGCAGACCCAGCTGTGCATCATCGGCTGCGTGCCTGCCATTGGCGAGCACTGGGCCAAG
GGCAAGAGCTGCAAGCCCACCAACGTGCAGCAGGGCGACTGCCCCCCTCTGGAACTGGTCAACA
CACCCATCGAGGACGGCGACATGATCGACACCGGCTACGGCGCCATGGACTTCGGCACCCTGCA
GGAAACCAAGAGCGAGGTCCCCCTGGACATCTGCCAGAGCGTGTGCAAGTACCCCGACTACCTG
CAGATGAGCGCCGACGTGTACGGCGACAGCATGTTCTTTTGCCTGCGGCGGGAGCAGCTGTTCGC
CCGGCACTTCTGGAACAGAGGCGGCATGGTCGGCGACACCATCCCCACCGACATGTACATCAAG
GGCACCGACATCAGAGAGACACCCAGCAGCTACGTGTACGCCCCCAGCCCCAGCGGCAGCATGG
TGTCCAGCGACAGCCAGCTGTTCAACAAGCCCTACTGGCTGCACAAGGCCCAGGGCCACAACAA
CGGCATCTGCTGGCACAACCAGCTGTTTCTGACCGTGGTGGACACCACCAGAAGCACCAACTTCA
CCCTGAGCACCACCACCGACAGCACCGTGCCCGCCGTGTACGACAGCAATAAGTTCAAAGAATA
CGTGCGGCACGTGGAGGAATACGACCTGCAGTTCATCTTCCAGCTGTGTACCATCACCCTGTCCA
CCGACGTGATGAGCTACATCCACACCATGAACCCCGCCATCCTGGACGACTGGAACTTCGGCGTG
GCCCCTCCCCCTAGCGCCAGCCTGGTGGATACCTACAGATACCTGCAGAGCGCCGCCATCACCTG
CCAGAAGGACGCCCCTGCCCCCGTGAAGAAGGACCCCTACGACGGCCTGAACTTCTGGAATGTG
GACCTGAAAGAGAAGTTCAGCAGCGAGCTGGACCAGTTCCCCCTGGGCCGGAAGTTCCTGCTGC
AAGCCGGCGTGCGGAGAAGGCCCACCATCGGCCCCAGAAAGCGGACCGCCACCGCAGCCACAA
CCTCCACCTCCAAGCACAAGCGGAAGCGGGTGTCCAAGTGA Sequence 15 (SEQ ID NO: 15):
ATGGCTTTGTGGCGGTCTAGTGACAACACGGTGTATTTGCCACCCCCTTCTGTGGCGAAGGTTGT
CAATACAGATGATTATGTAACACGTACAGGCATATATTATTATGCTGGAAGCTCTCGCTTATTAA
CAGTAGGGCATCCTTATTTTAAGGTACCTGTAAATGGTGGCCGCAAGCAGGAAATACCTAAGGTG
TCTGCATATCAGTATAGGGTATTTAGGGTATCCCTACCTGATCCTAATAAGTTTGGCCTTCCGGAT
CCTTCCCTTTATAATCCTGACACACAACGCCTGGTATGGCCTGTATAGGTGTGGAAATTGGTAG
AGGCCAGCCATTGGGCGTTGGTGTTAGTGGACATCCTTTATATAATAGATTGGATGATACTGAAA
ATTCACATTTTTCCTCTGCTGTTAATACACAGGACAGTAGGGACAATGTGTCTGTGGACTATAAG
CAGACACAGTTATGTATTATAGGCTGTGTTCCTGCTATGGGAGAGCACTGGGCAAAGGGCAAGG
CCTGTAAGTCCACTACTGTACAACAGGGCGATTGTCCACCATTAGAATTAGTTAATACTGCAATT
GAGGATGGCGATATGATAGATACAGGCTATGGAGCCATGGACTTTCGTACATTGCAGGAAACCA
AAAGTGAGGTACCACTAGATATTTGCCAATCCGTGTGTAAATATCCTGATTATTTGCAGATGTCT
GCTGATGTATATGGGGACAGTATGTTTTTTTGTTTGCGCAAGGAACAGTTATTTGCCAGACACTTT
TGGAATAGAGGTGGCATGGTGGGCGACACAATACCTTCAGAGTTATATATTAAAGGCACGGATA
TACGTGATCGTCCTGGTACTCATGTATATTCCCCTTCCCCAAGTGGCTCTATGGTTTCTTCTGATTC
CCAGTTGTTTAATAAGCCCTATTGGTTGCATAAGGCCCAGGGACACAATAATGGCATTTGTTGGC
ATAACCAGTTGTTTATTACTGTGGTGGACACTACACGTAGTACTAATTTTACATTGTCTGCCTGCA
CCGAAACAGCCATACCTGCTGTATATAGCCCTACAAAGTTTAAGGAATATACTAGGCATGTGGAG
GAATATGATTTACAATTTATATTCAGTTGTGTACTATCACATTAACTGCAGACGTTATGGCCTAC
ATCCATACTATGAATCCTGCAATTTTGGACAATTGGAATATAGGCGTTACCCCTCCACCATCTGC
AAGCTTGGTGGACACGTATAGGTATTTACAATCAGCAGCTATAGCATGTCAGAAGGATGCTCCTG
CACCTGAAAAAAAGGATCCCTATGACGATTTAAAATTTTGGAATGTTGATTTAAAGGAAAAGTTT
AGTACAGAACTAGATCAGTTTCCTTTGGGGCGCAAATTTTTACTACAGGTAGGGGCTCGCAGACG
TCCTACTATAGGCCCTCGCAAACGCCCTGCATCAGCTAAATCGTCTTCCTCAGCCTCTAAACACA
AACGGAAACGTGTGTCCAAGTAA Sequence 16 (SEQ ID NO: 16):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTGCCCATGAGCGGCGGCA
GAAAGCAGGGCATCCCCAAGGTGTCCGCCTACCAGTACCGCGTGTTCCGCGTCACCCTCCCAGAC
CCCAACAAGTTCTCCATCCCCGACGCCAGCCTGTACAACCCCGAGACCCAGCGCCTGGTGTGGGC
CTGCGTGGGCGTGGAAGTCGGGCGCGGGCAGCCCCTCGGCGTCGGCATCTCCGGCCACCCCCTGT
ACAACCGCCAGGACGACACCGAGAATAGCCCCTTCAGCAGCAACAAAAAGGATTCCCGCGA
CAACGTCAGCGTCGACTACAAGCAGACCCAGCTCTGTATCATCGGGTGCGTCCCAGCAATCGGCG
AACACTGGGGCAAGGGCAAGGCCTGTAAGCCAAACAACGTGAGCACCGGCGATTGCCCCCCCCT
GGAGCTGGTGAATACACCCATCGAAGACGGCGACATGATCGACACCGGGTACGGCGCCATGGAT
TTCGGCGCCCTCCAGGAGACAAAGTCCGAAGTCCCCCTGGACATCTGCCAGAGCATCTGCAAGTA
CCCCGACTACCTCCAGATGAGCGCCGACGTCTACGGCGATTCCATGTTCTTCTGCCTGCGCCGCG
AGCAGCTCTTCGCCCGCCACTTCTGGAACCGCGGCGGCATGGTCGGCGATGCAATCCCCGCACAG
CTCTACATCAAGGGGACCGACATCCGCGCCAATCCAGGCTCCAGCGTGTTGTATGTCCAAGCCATC
CGGCAGCATGGTGACAAGCGACAGCCAGCTGTTCAACAAGCCCTACTGGCTGCACAAGGCACAG
GGGCATAATAACGGCATCTGCTGGCACAACCAGCTGTTCCTGACCGTCGTGGATACCACACGCTC
CACAAATTTCACCCTGAGCACAAGCATCGAAAGCAGCATCCCCAGCACCTACGACCCCAGCAAG
TTCAAGGAGTACACACGCCACGTCGAAGAATACGACCTGCAGTTCATCTTCCAGCTCTGCACCGT
GACCCTGACCACCGACGTCATGAGCTACATCCACACCATGAACAGCAGCATCCTCGATAACTGG
AACTTCGCCGTGGCCCCCCCCCCAGCGCATCCCTCGTGGATACCTATCGCTATCTGCAGAGCGC
CGCAATCACCTGCCAGAAGGACGCCCCGCCCCCGAGAAGAAGGACCCCTACGATGGCCTGAAG
TTCTGGAACGTCGATCTGCGCGAGAAGTTCTCCCTGGAGCTGGACCAGTTCCCCCTCGGCCGCAA
GTTCCTCCTCCAGGCAGCGTGCGCCGCCGCCCCACCATCGGCCCACGCAAGCGCCCCGCCGCA
GCACCAGCAGCAGCAGCGCCACCAAGCACAAGCGCAAGCGCGTCAGCAAGTGA Sequence 17 (SEQ ID NO: 17):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA TABLE 1 -continued Description of sequences SEQ ID NO: Description CCCCAACAAGTTCTCCATCCCCGACGCCAGCCTGTACAACCCCGAGACCCAGCGCCTGGTGTGGG
CCTGCGTGGGCGTCGAAGTCGGCAGAGGCCAGCCCCTGGGCGTGGGCCTGAGCGGCCACCCCCT
GTACAATCGGCTGGACGACACCGAGAACAGGCCCCTTCAGCAGCAACAAGAACCCCAAGGACAGC
CGGGACAACGTGGCCGTGGACTGCAAGCAGACCCAGCTCTGTATCATCGGGTGCGTCCCAGCAA
TCGGCCGAACACTGGGGCAAGGGCAAGGCCTGTAAGCCAAACAACGTGAGCACCGGCGATTGCCC
CCCCCTGGAGCTGGTGAATACACCCATCGAAGACGGCGACATGATCGACACCGGGTACGGCGCC
ATGGATTTCGGCGCCCTCCAGGAGACAAAGTCCGAAGTCCCCCTGGACATCTGCCAGAGCATCTG
CAAGTACCCCGACTACCTCCAGATGAGCGCCGACGTCTACGGCGATTCCATGTTCTTCTGCCTGC
GCCGCGAGCAGCTCTTCGCCCGCCACTTCTGGAACCGCGGCGGCATGGTCGGCGATGCAATCCCC
GCACAGCTCTACATCAAGGGGACCGACATCCGCGCCAATCCAGGCTCCAGCGTGTATTGTCCAAG
CCCATCCGGCAGCATGGTGACAAGCGACAGCCAGCTGTTCAACAAGCCCTACTGGCTGCACAAG
GCACAGGGGCATAATAACGGCATCTGCTGGCACAACCAGCTGTTCCTGACCGTCGTCGATACCAC
ACGCTCCACAAATTTCACCCTGAGCACAAGCATCGAAAGCAGCATCCCCAGCACCTACGACCCC
AGCAAGTTCAAGGAGTACACACGCCACGTCGAAGAATACGACCTGCAGTTCATCTTCCAGCTCTG
CACCGTGACCCTGACCACCGACGTCATGAGCTACATCCACACCATGAACAGCAGCATCCTCGATA
ACTGGAACTTCGCCGTGGCCCCCCCCCCCCAGCGCATCCTCGTGGATACCTATCGCTATCTGCAG
AGCGCCGCAATCACCTGCCAGAAGGACGCCCCCGCCCCCGAGAAGAAGGACCCCTACGATGGCC
TGAAGTTCTGGAACGTCGATCTGCGCGAGAAGTTCTCCCTGGAGCTGGACCAGTTCCCCCTCGGC
CGCAAGTTCCTCCTCCAGGCACGCGTGCGCCGCCGCCCCACCATCGGCCCACGCAAGCGCCCCGC
CGCCAGCACCAGCAGCAGCAGCGCCACCAAGCACAAGCGCAAGCGCGTCAGCAAGTGA
Sequence 18 (SEQ ID NO: 18):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA
CCCCAACAAGTTCTCCATCCCCGACGCCAGCCTGTACAACCCCGAGACCCAGCGCCTGGTGTGGG
CCTGCGTGGGCGTCGAAGTCGGGCGCGGGCAGCCCCTCGGCGTCGGCATCTCCGGCCACCCCCTG
TACAACCGCCAGGACGACACCGAGAATAGCCCCTTCAGCAGCACAACAAACAAGGATTCCCGCG
ACAACGTCAGCGTCGACTACAAGCAGACCCAGCTCTGTATCATCGGGTGCGTCCCAGCAATCGGC
GAACACTGGGCCAAGGGCAAGAGCTGCAAGCCCACCAACGTGCAGCAGGGCGACTGCCCCCCTC
TGGAGCTGGTGAATACACCCATCGAAGACGGCGACATGATCGACACCGGGTACGCGCCATGGA
TTTCGGCGCCCTCCAGGAGACAAAGTCCGAAGTCCCCCTGGACATCTGCCAGAGCATCTGCAAGT
ACCCCGACTACCTCCAGATGAGCGCCGACGTCTACGGCGATTCCATGTTCTTCTGCCTGCGCCGC
GAGCAGCTCTTCGCCCGCCACTTCTGGAACCGCGGCGGCATGGTCGGCGATGCAATCCCCGCACA
GCTCTACATCAAGGGGACCGACATCCGCGCCAATCCAGGCTCCAGCGTGTATTGTCCAAGCCCAT
CCGGCAGCATGGTGACAAGCGACAGCCAGCTGTTCAACAAGCCCTACTGGCTGCACAAGGCACA
GGGGCATAATAACGGCATCTGCTGGCACAACCAGCTGTTCCTGACCGTCGTCGATACCACACGCT
CCACAAATTTCACCCTGAGCACAAGCATCGAAAGCAGCATCCCCAGCACCTACGACCCCAGCAA
GTTCAAGGAGTACACACGCCACGTCGAAGAATACGACCTGCAGTTCATCTTCCAGCTCTGCACCG
TGACCCTGACCACCGACGTCATGAGCTACATCCACACCATGAACAGCAGCATCCTCGATAACTGG
AACTTCGCCGTGGCCCCCCCCCCCAGCGCATCCTCGTGGATACCTATCGCTATCTGCAGAGCGC
CGCAATCACCTGCCAGAAGGACGCCCCCGCCCCCGAGAAGAAGGACCCCTACGATGGCCTGAAG
TTCTGGAACGTCGATCTGCGCGAGAAGTTCTCCCTGGAGCTGGACCAGTTCCCCCTCGGCCGCAA
GTTCCTCCTCCAGGCACGCGTGCGCCGCCGCCCCACCATCGGCCCACGCAAGCGCCCCGCCGCCA
GCACCAGCAGCAGCGCCACCAAGCACAAGCGCAAGCGCGTCAGCAAGTGA
Sequence 19 (SEQ ID NO: 19):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA
CCCCAACAAGTTCTCCATCCCCGACGCCAGCCTGTACAACCCCGAGACCCAGCGCCTGGTGTGGG
CCTGCGTGGGCGTCGAAGTCGGGCGCGGGCAGCCCCTCGGCGTCGGCATCTCCGGCCACCCCCTG
TACAACCGCCAGGACGACACCGAGAATAGCCCCTTCAGCAGCACAACAAACAAGGATTCCCGCG
ACAACGTCAGCGTCGACTACAAGCAGACCCAGCTCTGTATCATCGGGTGCGTCCCAGCAATCGGC
GAACACTGGGGCAAGGGCAAGGCCTGTAAGCCAAACAACGTGAGCACCGGCGATTGCCCCCCCC
TGGAGCTGGTGAATACACCCATCGAAGACGGCGACATGATCGACACCGGGTACGGCGCCATGGA
TTTCGGCGCCCTCCAGGAGACAAAGTCCGAAGTCCCCCTGGACATCTGCCAGAGCATCTGCAAGT
ACCCCGACTACCTCCAGATGAGCGCCGACGTCTACGGCGATTCCATGTTCTTCTGCCTGCGCCGC
GAGCAGCTCTTCGCCCGCCACTTCTGGAACAGAGGCGGCATGGTCGGCGACACCATCCCCACCG
ACATGTACATCAAGGGCCACCGACATCAGAGAGACACCCAGCAGCTACGTGTACTGT
CCAAGCCCATCCGGCAGCATGGTGACAAGCGACAGCCAGCTGTTCAACAAGCCCTACTGGCTGC
ACAAGGCACAGGGGCATAATAACGGCATCTGCTGGCACAACCAGCTGTTCCTGACCGTCGTCGA
TACCACACGCTCCACAAATTTCACCCTGAGCACAAGCATCGAAAGCAGCATCCCCAGCACCTACG
ACCCCAGCAAGTTCAAGGAGTACACACGCCACGTCGAAGAATACGACCTGCAGTTCATCTTCCA
GCTCTGCACCGTGACCCTGACCACCGACGTCATGAGCTACATCCACACCATGAACAGCAGCATCC
TCGATAACTGGAACTTCGCCGTGGCCCCCCCCCCCAGCGCATCCTCGTGGATACCTATCGCTAT
CTGCAGAGCGCCGCAATCACCTGCCAGAAGGACGCCCCCGCCCCCGAGAAGAAGGACCCCTACG
ATGGCCTGAAGTTCTGGAACGTCGATCTGCGCGAGAAGTTCTCCCTGGAGCTGGACCAGTTCCCC
CTCGGCCGCAAGTTCCTCCTCCAGGCACGCGTGCGCCGCCGCCCCACCATCGGCCCACGCAAGCG
CCCCGCCGCCAGCACCAGCAGCAGCGCCACCAAGCACAAGCGCAAGCGCGTCAGCAAGTGA
Sequence 20 (SEQ ID NO: 20):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA
CCCCAACAAGTTCTCCATCCCCGACGCCAGCCTGTACAACCCCGAGACCCAGCGCCTGGTGTGGG
CCTGCGTGGGCGTCGAAGTCGGGCGCGGGCAGCCCCTCGGCGTCGGCATCTCCGGCCACCCCCTG
TACAACCGCCAGGACGACACCGAGAATAGCCCCTTCAGCAGCACAACAAACAAGGATTCCCGCG TABLE 1-continued Description of sequences SEQ ID NO: Description ACAACGTCAGCGTCGACTACAAGCAGACCCAGCTCTGTATCATCGGGTGCGTCCCAGCAATCGGC
GAACACTGGGGCAAGGGCAAGGCCTGTAAGCCAAACAACGTGAGCACCGGCGATTGCCCCCCCC
TGGAGCTGGTGAATACACCCATCGAAGACGGCGACATGATCGACACCGGGTACGGCGCCATGGA
TTTCGGCGCCCTCCAGGAGACAAAGTCCGAAGTCCCCCTGGACATCTGCCAGAGCATCTGCAAGT
ACCCCGACTACCTCCAGATGAGCGCCGACGTCTACGGCGATTCCATGTTCTTCTGCCTGCGCCGC
GAGCAGCTCTTCGCCCGCCACTTCTGGAACCGCGGCGGCATGGTCGGCGATGCAATCCCCGCACA
GCTCTACATCAAGGGGACCGACATCCGCGCCAATCCAGGCTCCAGCGTGTATTGTCCAAGCCCAT
CCGGCAGCATGGTGACAAGCGACAGCCAGCTGTTCAACAAGCCCTACTGGCTGCACAAGGCACA
GGGGCATAATAACGGCATCTGCTGGCACAACCAGCTGTTCCTGACCGTCGTCGATACCACACGCT
CCACAAATTTCACCCTGAGCACAAGCACCGACAGCACCGTGCCCGCCGTGTACGACAGCAATAA
GTTCAAGGAGTACACACGCCACGTCGAAGAATACGACCTGCAGTTCATCTTCCAGCTCTGCACCG
TGACCCTGACCACCGACGTCATGAGCTACATCCACACCATGAACAGCAGCATCCTCGATAACTGG
AACTTCGCCGTGGCCCCCCCCCCAGCGCATCCCTCGTGGATACCTATCGCTATCTGCAGAGCGC
CGCAATCACCTGCCAGAAGGACGCCCCCGCCCCGAGAAGAAGGACCCCTACGATGGCCTGAAG
TTCTGGAACGTCGATCTGCGCGAGAAGTTCTCCCTGGAGCTGGACCAGTTCCCCCTCGGCCGCAA
GTTCCTCCTCCAGGCACGCGTGCGCCGCCGCCCCACCATCGGCCCACGCAAGCGCCCCGCCGCCA
GCACCAGCAGCAGCAGCGCCACCAAGCACAAGCGCAAGCGCGTCAGCAAGTGA Sequence 21 (SEQ ID NO: 21):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTTAAGGTACCTGTAAATGGTGGCC
GCAAGCAGGAAATACCTAAGGTGTCTGCCTACCAGTACCGCGTGTTCCGCGTCACCCTCCCAGAC
CCCAACAAGTTCTCCATCCCCGACGCCAGCCTGTACAACCCCGAGACCCAGCGCCTGGTGTGGGC
CTGCGTGGGCGTCGAAGTCGGGCGCGGGCAGCCCCTCGGCGTCGGCATCTCCGGCCACCCCCTGT
ACAACCGCCAGGACGACACCGAGAATAGCCCCTTCAGCAGCACAACAAACAAGGATTCCCGCGA
CAACGTCAGCGTCGACTACAAGCAGACCCAGCTCTGTATCATCGGGTGCGTCCCAGCAATCGGCG
AACACTGGGGCAAGGGCAAGGCCTGTAAGCCAAACAACGTGAGCACCGGCGATTGCCCCCCCCT
GGAGCTGGTGAATACACCCATCGAAGACGGCGACATGATCGACACCGGGTACGGCGCCATGGAT
TTCGGCGCCCTCCAGGAGACAAAGTCCGAAGTCCCCCTGGACATCTGCCAGAGCATCTGCAAGTA
CCCCGACTACCTCCAGATGAGCGCCGACGTCTACGGCGATTCCATGTTCTTCTGCCTGCGCCGCG
AGCAGCTCTTCGCCCGCCACTTCTGGAACAGAGGCGGCATGGTCGGCGACACCATCCCCACCGAC
ATGTACATCAAGGGCACCGACATCAGAGAGACACCCAGCAGCTACGTGTACTGT
CCAAGCCCATCCGGCAGCATGGTGACAAGCGACAGCCAGCTGTTCAACAAGCCCTACTGGCTGC
ACAAGGCACAGGGGCATAATAACGGCATCTGCTGGCACAACCAGCTGTTCCTGACCGTCGTCGA
TACCACACGCTCCACAAATTTCACCCTGAGCACAAGCATCGAAAGCAGCATCCCCAGCACCTACG
ACCCCAGCAAGTTCAAGGAGTACACACGCCACGTCGAAGAATACGACCTGCAGTTCATCTTCCA
GCTCTGCACCGTGACCCTGACCACCGACGTCATGAGCTACATCCACACCATGAACAGCAGCATCC
TCGATAACTGGAACTTCGCCGTGGCCCCCCCCCCAGCGCATCCCTCGTGGATACCTATCGCTAT
CTGCAGAGCGCCGCAATCACCTGCCAGAAGGACGCCCCCGCCCCGAGAAGAAGGACCCCTACG
ATGGCCTGAAGTTCTGGAACGTCGATCTGCGCGAGAAGTTCTCCCTGGAGCTGGACCAGTTCCCC
CTCGGCCGCAAGTTCCTCCTCCAGGCACGCGTGCGCCGCCGCCCCACCATCGGCCCACGCAAGCG
CCCCGCCGCCAGCACCAGCAGCAGCAGCGCCACCAAGCACAAGCGCAAGCGCGTCAGCAAGTGA Sequence 22 (SEQ ID NO: 22):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA
CCCCAACAAGTTCTCCATCCCCGACGCCAGCCTGTACAACCCCGAGACCCAGCGCCTGGTGTGGG
CCTGCGTGGGCGTCGAAGTCGGTAGAGGCCAGCCATTGGGCGTTGGTGTTAGTGGACATCCTTTA
TATAATAGATTGGATGATACTGAAAATTCACATTTTTCCTCTGCTGTTAATACACAGGACAGTAG
GGACAATGTGTCTGTGGACTATAAGCAGACCCAGCTCTGTATCATCGGGTGCGTCCCAGCAATCG
GCGAACACTGGGGCAAGGGCAAGGCCTGTAAGCCAAACAACGTGAGCACCGGCGATTGCCCCCC
CCTGGAGCTGGTGAATACACCCATCGAAGACGGCGACATGATCGACACCGGGTACGGCGCCATG
GATTTCGGCGCCCTCCAGGAGACAAAGTCCGAAGTCCCCCTGGACATCTGCCAGAGCATCTGCAA
GTACCCCGACTACCTCCAGATGAGCGCCGACGTCTACGGCGATTCCATGTTCTTCTGCCTGCGCC
GCGAGCAGCTCTTCGCCCGCCACTTCTGGAACAGAGGCGGCATGGTCGGCGACACCATCCCCACC
GACATGTACATCAAGGGCACCGACATCAGAGAGACACCCAGCAGCTACGTGTAC
TGTCCAAGCCCATCCGGCAGCATGGTGACAAGCGACAGCCAGCTGTTCAACAAGCCCTACTGGCT
GCACAAGGCACAGGGGCATAATAACGGCATCTGCTGGCACAACCAGCTGTTCCTGACCGTCGTC
GATACCACACGCTCCACAAATTTCACCCTGAGCACAAGCATCGAAAGCAGCATCCCCAGCACCT
ACGACCCCAGCAAGTTCAAGGAGTACACACGCCACGTCGAAGAATACGACCTGCAGTTCATCTT
CCAGCTCTGCACCGTGACCCTGACCACCGACGTCATGAGCTACATCCACACCATGAACAGCAGCA
TCCTCGATAACTGGAACTTCGCCGTGGCCCCCCCCCCAGCGCATCCCTCGTGGATACCTATCGCT
ATCTGCAGAGCGCCGCAATCACCTGCCAGAAGGACGCCCCCGCCCCGAGAAGAAGGACCCCTA
CGATGGCCTGAAGTTCTGGAACGTCGATCTGCGCGAGAAGTTCTCCCTGGAGCTGGACCAGTTCC
CCCTCGGCCGCAAGTTCCTCCTCCAGGCACGCGTGCGCCGCCGCCCCACCATCGGCCCACGCAAG
CGCCCCGCCGCCAGCACCAGCAGCAGCAGCGCCACCAAGCACAAGCGCAAGCGCGTCAGCAAGT
GA Sequence 23 (SEQ ID NO: 23):
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA
CCCCAACAAGTTCTCCATCCCCGACGCCAGCCTGTACAACCCCGAGACCCAGCGCCTGGTGTGGG
CCTGCGTGGGCGTCGAAGTCGGGCGCGGGCAGCCCCTCGGCGTCGGCATCTCCGGCCACCCCCTG
TACAACCGCCAGGACGACACCGAGAATAGCCCCTTCAGCAGCACAACAAACAAGGATTCCCGCG
ACAACGTCAGCGTCGACTACAAGCAGACCCAGCTCTGTATCATCGGGTGCGTCCCAGCAATCGGC
GAACACTGGGGCAAAGGGCAAGGCCTGTAAGTCCACTACTGTACAACAGGGCGATTGTCCACCAC TABLE 1 -continued Description of sequences SEQ ID NO: Description

```
TGGAGCTGGTGAATACACCCATCGAAGACGGCGACATGATCGACACCGGGTACGGCGCCATGGA
TTTCGGCGCCCTCCAGGAGACAAAGTCCGAAGTCCCCCTGGACATCTGCCAGAGCATCTGCAAGT
ACCCCGACTACCTCCAGATGAGCGCCGACGTCTACGGCGATTCCATGTTCTTCTTGCCTGCGCCGC
GAGCAGCTCTTCGCCCGCCACTTCTGGAACAGAGGCGGCATGGTCGGCGACACCATCCCCACCG
ACATGTACATCAAGGGCACCGACATCAGAGAGACACCCAGCAGCTACGTGTACTGT
CCAAGCCCATCCGGCAGCATGGTGACAAGCGACAGCCAGCTGTTCAACAAGCCCTACTGGCTGC
ACAAGGCACAGGGGCATAATAACGGCATCTGCTGGCACAACCAGCTGTTCCTGACCGTCGTCGA
TACCACACGCTCCACAAATTTCACCCTGAGCACAAGCATCGAAAGCAGCATCCCCAGCACCTACG
ACCCCAGCAAGTTCAAGGAGTACACACGCCACGTCGAAGAATACGACCTGCAGTTCATCTTCCA
GCTCTGCACCGTGACCCTGACCACCGACGTCATGAGCTACATCCACACCATGAACAGCAGCATCC
TCGATAACTGGAACTTCGCCGTGGCCCCCCCCCCAGCGCATCCCTCGTGGATACCTATCGCTAT
CTGCAGAGCGCCGCAATCACCTGCCAGAAGGACGCCCCCGCCCCCGAGAAGAAGGACCCCTACG
ATGGCCTGAAGTTCTGGAACGTCGATCTGCGCGAGAAGTTCTCCCTGGAGCTGGACCAGTTCCCC
CTCGGCCGCAAGTTCCTCCTCCAGGCACGCGTGCGCCGCCGCCCCACCATCGGCCCACGCAAGCG
CCCCGCCGCCAGCACCAGCAGCAGCAGCGCCACCAAGCACAAGCGCAAGCGCGTCAGCAAGTGA
```

Sequence 24 (SEQ ID NO: 24):
```
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA
CCCCAACAAGTTCTCCATCCCCGACGCCAGCCTGTACAACCCCGAGACCCAGCGCCTGGTGTGGG
CCTGCGTGGGCGTCGAAGTCGGGCGCGGGCAGCCCCTCGGCGTCGGCATCTCCGGCCACCCCCTG
TACAACCGCCAGGACGACACCGAGAATAGCCCCTTCAGCAGCACAACAAACAAGGATTCCCGCG
ACAACGTCAGCGTCGACTACAAGCAGACCCAGCTCTGTATCATCGGGTGCGTCCCAGCAATCGGC
GAACACTGGGGCAAGGGCAAGGCCTGTAAGCCAAACAACGTGAGCACCGGCGATTGCCCCCCCC
TGGAGCTGGTGAATACACCCATCGAAGACGGCGACATGATCGACACCGGGTACGGCGCCATGGA
TTTCGGCGCCCTCCAGGAGACAAAGTCCGAAGTCCCCCTGGACATCTGCCAGAGCATCTGCAAGT
ACCCCGACTACCTCCAGATGAGCGCCGACGTCTACGGCGATTCCATGTTCTTCTGCCTGCGCCGC
GAGCAGCTCTTCGCCCGCCACTTCTGGAACAGAGGCGGCATGGTCGGCGACACCATCCCCACCG
ACATGTACATCAAGGGCACCGACATCAGAGAGACACCCAGCAGCTACGTGTACTGT
CCAAGCCCATCCGGCAGCATGGTGACAAGCGACAGCCAGCTGTTCAACAAGCCCTACTGGCTGC
ACAAGGCACAGGGGCATAATAACGGCATCTGCTGGCACAACCAGCTGTTCCTGACCGTCGTCGA
TACCACACGCTCCACAAATTTCACCCTGAGCACAAGCACCGAAACAGCCATACCTGCTGTATATA
GCCCTACAAAGTTCAAGGAGTACACACGCCACGTCGAAGAATACGACCTGCAGTTCATCTTCCAG
CTCTGCACCGTGACCCTGACCACCGACGTCATGAGCTACATCCACACCATGAACAGCAGCATCCT
CGATAACTGGAACTTCGCCGTGGCCCCCCCCCCAGCGCATCCCTCGTGGATACCTATCGCTATC
TGCAGAGCGCCGCAATCACCTGCCAGAAGGACGCCCCCGCCCCGAGAAGAAGGACCCCTACGA
TGGCCTGAAGTTCTGGAACGTCGATCTGCGCGAGAAGTTCTCCCTGGAGCTGGACCAGTTCCCCC
TCGGCCGCAAGTTCCTCCTCCAGGCACGCGTGCGCCGCCGCCCCACCATCGGCCCACGCAAGCGC
CCCGCCGCCAGCACCAGCAGCAGCAGCGCCACCAAGCACAAGCGCAAGCGCGTCAGCAAGTGA
```

Sequence 25 (SEQ ID NO: 25):
TIPTDMYIKGTDIRETPSSY

Sequence 26 (SEQ ID NO: 26):
VSGHPLYNRLDDTENSHFSSAVNTQ

Sequence 27 (SEQ ID NO: 27):
AKGKACKSTTVQQ

Sequence 28 (SEQ ID NO: 28):
TETAIPAVYSPT

Sequence 29 (SEQ ID NO: 29):
NIPSVAKVVNTDDYVTRTGIYYYAGSRLLTVGHPYFKVGMNGGRKQDIPKVSAYQYRVFRVTLPDP
NKFSIPDASLYNPETQRLVWACVGVEVGRGQPLGVGISGHPLYNRQDDTENSPFSSTTNKDSRDNVS
VDYKQTQLCIIGCVPAIGEHWGKGKACKPNNVSTGDCPPLELVNTPIEDGDMIDTGYGAMDFGALQE
TKSEVPLDICQSICKYPDYLQMSADVYGDSMFFCLRREQLFARHFWNRGGMVGDAIPAQLYIKGTDI
RANPGSSVYCPSPSGSMVTSDSQLFNKPYWLIIKAQGHNNGICWHNQLFLTVVDTTRSTNFTLSTSIES
SIPSTYDPSKFKEYTRHVEEYDLQFIFQLCTVTLTTDVMSYIHTMNSSILDNWNFAVAPPPSASLVDTY
RYLQSAAITCQKDAPAPEKKDPYDGLKFWNVDLREKFSLELDQFPLGRKFLLQARVRRRPTIGPRKRP
AASTSSSSATKHKRKRVSK Sequence 30 (SEQ ID NO: 30):
```
ATGCCCAGCGTCGCCAAGGTCGTGAACACCGACGACTACGTCACCCGCACCGGGATCTACTACTA
CGCCGGGTCCAGCCGCCTGCTGACCGTGGGCCACCCCTACTTCAAGGTCGGCATGAACGGCGGG
CGCAAGCAGGATATCCCCAAGGTCAGCGCCTACCAGTACCGCGTGTTCCGCGTCACCCTCCCAGA
CCCCAACAAGTTCTCCATCCCCGACGCCAGCCTGTACAACCCCGAGACCCAGCGCCTGGTGTGGG
CCTGCGTGGGCGTCGAAGTCGGGCGCGGGCAGCCCCTCGGCGTCGGCATCTCCGGCCACCCCCTG
TACAACCGCCAGGACGACACCGAGAATAGCCCCTTCAGCAGCACAACAAACAAGGATTCCCGCG
ACAACGTCAGCGTCGACTACAAGCAGACCCAGCTCTGTATCATCGGGTGCGTCCCAGCAATCGGC
GAACACTGGGGCAAGGGCAAGGCCTGTAAGCCAAACAACGTGAGCACCGGCGATTGCCCCCCCC
TGGAGCTGGTGAATACACCCATCGAAGACGGCGACATGATCGACACCGGGTACGGCGCCATGGA
TTTCGGCGCCCTCAGGAGACAAAGTCCGAAGTCCCCCTGGACATCTGCCAGAGCATCTGCAAGT
ACCCCGACTACCTCCAGATGAGCGCCGACGTCTACGGCGATTCCATGTTCTTCTGCCTGCGCCGC
GAGCAGCTCTTCGCCCGCCACTTCTGGAACGCGGCGGCATGGTCGGCGATGCAATCCCCGCACA
GCTCTACATCAAGGGGACCGACATCGCGCCAATCAGGCTCCAGCGTGTTGTATTGTCCAAGCCCAT
CCGGCAGCATGGTGACAAGCGACAGCCAGCTGTTCAACAAGCCCTACTGGCTGCACAAGGCACA
GGGGCATAATAACGGCATCTGCTGGCACAACCAGCTGTTCCTGACCGTCGTCGATACCACACGCT
CCACAAATTTCACCCTGAGCACAAGCATCGAAAGCAGCATCCCCAGCACCTACGACCCCAGCAA
GTTCAAGGAGTACACACGCCACGTCGAAGAATACGACCTGCAGTTCATCTTCCAGCTCTGCACCG
TGACCCTGACCACCGACGTCATGAGCTACATCCACACCATGAACAGCAGCATCCTCGATAACTGG
```

TABLE 1-continued

Description of sequences

SEQ
ID NO:Description

AACTTCGCCGTGGCCCCCCCCCCAGCGCATCCCTCGTGGATACCTATCGCTATCTGCAGAGCGC
CGCAATCACCTGCCAGAAGGACGCCCCCGCCCCCGAGAAGAAGGACCCCTACGATGGCCTGAAG
TTCTGGAACGTCGATCTGCGCGAGAAGTTCTCCCTGGAGCTGGACCAGTTCCCCCTCGGCCGCAA
GTTCCTCCTCCAGGCACGCGTGCGCCGCCGCCCCACCATCGGCCCACGCAAGCGCCCCGCCGCCA
GCACCAGCAGCAGCAGCGCCACCAAGCACAAGCGCAAGCGCGTCAGCAAGTGA
Sequence 31 (SEQ ID NO: 31):
MVYLPPPSVAKVVNTDDYVTRTGIYYYAGSSRLLTVGHPYFKVPVNGGRKQEIPKVSAYQYRVFRVS
LPDPNKFGLPDPSLYNPDTQRLVWACIGVEIGRGQPLGVGVSGHPLYNRLDDTENSHFSSAVNTQDSR
DNVSVDYKQTQLCIIGCVPAMGEHWAKGKACKSTTVQQGDCPPLELVNTAIEDGDMIDTGYGAMDF
RTLQETKSEVPLDICQSVCKYPDYLQMSADVYGDSNIFFCLRKEQLFARHFWNRGGMVGDTIPSELYI
KGTD1RDRPGTHVYSPSPSGSMVSSDSQLFNKPYWLHKAQGHNNGICWHNQLFITVVDTTRSTNFTLS
ACTETAIPAVYSPTKFKEYTRHVEEYDLQFIFQLCTITLTADVMAYIHTMNPAILDNWNIGVTPPPSAS
LVDTYRYLQSAAIACQKDAPAPEKKDPYDDLKFWNVDLKEKFSTELDQFPLGRKFLLQVGARRRPTI
GPRKRPASAKSSSSASKHKRKRVSK
Sequence 32 (SEQ ID NO: 32):
ATGGTGTATTTGCCACCCCCTTCTGTGGCGAAGGTTGTCAATACAGATGATTATGTAACACGTAC
AGGCATATATTATTATGCTGGAAGCTCTCGCTTATTAACAGTAGGGCATCCTTATTTTAAGGTACC
TGTAAATGGTGGCCGCAAGCAGGAAATACCTAAGGTGTCTGCATATCAGTAGGGTATTTAGG
GTATCCCTACCTGATCCTAATAAGTTTGGCCTTCCGGATCCTTCCCTTTATAATCCTGACACACAA
CGCCTGGTATGGGCCTGTATAGGTGTGGAAATTGGTAGAGGCCAGCCATTGGGCGTTGGTGTTAG
TGGACATCCTTTATATAATAGATTGGATGATACTGAAAATTCACATTTTTCCTCTGCTGTTAATAC
ACAGGACAGTAGGGACAATGTGTCTGTGGACTATAAGCAGACACAGTTATGTATTATAGGCTGT
GTTCCTGCTATGGGAGAGCACTGGGCAAAGGGCAAGGCCTGTAAGTCCACTACTGTACAACAGG
GCGATTGTCCACCATTAGAATTAGTTAATACTGCAATTGAGGATGGCGATATGATAGATACAGGC
TATGGAGCCATGGACTTTCGTACATTGCAGGAAACCAAAAGTGAGGTACCACTAGATATTTGCCA
ATCCGTGTGTAAATATCCTGATTATTTGCAGATGTCTGCTGATGTATATGGGGACAGTATGTTTTT
TTGTTTGCGCAAGGAACAGTTATTTGCCAGACACTTTTGGAATAGAGGTGGCATGGTGGGCGACA
CAATACCTTCAGAGTTATATATTAAAGGCACGGATATACGTGATCGTCCTGGTACTCATGTATAT
TCCCCTTCCCCAAGTGGCTCTATGGTTTCTTCTGATTCCCAGTTGTTTAATAAGCCCTATTGGTTGC
ATAAGGCCCAGGGACACAATAATGGCATTTGTTGGCATAACCAGTTGTTTATTACTGTGGTGGAC
ACTACACGTAGTACTAATTTTACATTGTCTGCCTGCACCGAAACAGCCATACCTGCTGTATATAG
CCCTACAAAGTTTAAGGAATATACTAGGCATGTGGAGGAATATGATTTACAATTTATATTTCAGT
TGTGTACTATCACATTAACTGCAGACGTTATGGCCTACATCCATACTATGAATCCTGCAATTTTGG
ACAATTGGAATATAGGCGTTACCCCTCCACCATCTGCAAGCTTGGTGGACACGTATAGGTATTTA
CAATCAGCAGCTATAGCATGTCAGAAGGATGCTCCTGCACCTGAAAAAAAGGATCCCTATGACG
ATTTAAAATTTTGGAATGTTGATTTAAAGGAAAAGTTTAGTACAGAACTAGATCAGTTTCCTTTG
GGGCGCAAATTTTTACTACAGGTAGGGGCTCGCAGACGTCCTACTATAGGCCCTCGCAAACGCCC
TGCATCAGCTAAATCGTCTTCCTCAGCCTCTAAACACAAACGGAAACGTGTGTCCAAGTAA
Sequence 33 (SEQ ID NO: 33):
PMSGGRKQG
Sequence 34 (SEQ ID NO: 34):
LSGIIPLYNRLDDTENSPFSSNKNPKDSRDNVAVDC
Sequence 35 (SEQ ID NO: 35):
AKGKSCKPTNVQQ
Sequence 36 (SEQ ID NO: 36):
TDSTVPAVYDSN
Sequence 37 (SEQ ID NO: 37):
PVNGGRKQE

SPECIFIC MODES FOR CARRYING OUT THE INVENTION

The present invention is further described by reference to the examples as follows, wherein the examples are used only for the purpose of illustrating the present invention, rather than limiting the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; and restriction enzymes are used under the conditions recommended by the manufacturers. Those skilled in the art understand that the examples are used for illustrating the present invention, but not intended to limit the protection scope of the present invention.

Example 1. Expression and Purification of the Mutated HPV39 L1 Proteins Construction of Expression Vectors An expression vector encoding the mutated HPV39 L1 protein comprising a segment from HPV68 L1 protein was constructed by PCR for multi-site mutagenesis, wherein the initial template used was the plasmid pTO-T7-HPV39N15C (encoding the HPV39 L1 protein having 15 amino acids truncated at N-terminal; abbreviated as 39L1N15 in Table 2). The templates and primers for each PCR were shown in Table 2, and the amplification conditions for PCR were as followed: denaturation at 94° C. for 10 min; 25 cycles (denaturation at 94° C. for 50 sec, annealing at a given temperature for a certain period of time, and extension at 72° C. for 7.5 min); and final extension at 72° C. for 10 min. The temperature and time of annealing were listed in Table 2. The sequences of the PCR primers used were listed in Table 3.

To the amplification product (50 μL), 2 μL restriction endonuclease DpnI (Fermentas (MBI), Cat. No. FD1704, 2500U/tube) was added, and the resultant mixture was incubated at 37° C. for 60 min. 10 μL of the product of digestion was used to transform 40 μL competent *E. coli* ER2566 (purchased from New England Biolabs) prepared by the Calcium chloride method. The transformed *E. coli* was spread onto solid LB medium (the components of the LB medium: 10 g/L peptone, 5 g/L yeast powder, 10 g/L NaCl, the same hereinafter) containing kanamycin (at a final concentration of 25 μg/mL, the same hereinafter), and was subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequence of the fragments of interest inserted into the constructed plasmids (expression vectors) was SEQ ID NO: 16, and their encoded amino acid sequences was SEQ ID NO: 4 (the corresponding protein was designated as H39N15-68T1). The mutated protein H39N15-68T1 differs from HPV39N15 by: the substitution of the amino acid residues from positions 53-61 of wild type HPV39 L1 protein with the amino acid residues from positions 53-61 of wild type HPV68 L1 protein.

Gibson assembly (Gibson D G, Young L, Chuang R Y, Venter J C, Hutchison C A, Smith H O. Enzymatic assembly of DNA molecules up to several hundred kilobases. Nat Methods. 2009; 6:343-5. doi: 10.1038/nmeth.1318) was used to construct the expression vector encoding the other mutated HPV39 L1 protein, wherein the mutated HPV39 L1 protein comprised a specific segment from HPV68 L1 and a specific segment from HPV70L1. In brief, a short fragment comprising mutations and a long fragment comprising no mutation were obtained by PCR, and Gibson assembly system was then used to ligate the two fragments to form a ring. The initial template used comprised the plasmid pTO-T7-HPV39N15 (encoding the HPV39 L1 protein having 15 amino acids truncated at N-terminal; abbreviated as 39L1N15 in Table 2), the plasmid pTO-T7-HPV68L1 (encoding the HPV68 L1 protein; abbreviated as 68L1N0 in Table 2), the plasmid pTO-T7-H39N15-68T4 (encoding the mutated protein H39N15-68T4; abbreviated as H39N15-68T4 in Table 2), and the plasmid pTO-T7-HPV70N10 (encoding the HPV70 L1 protein having 10 amino acids truncated at N-terminal; abbreviated as 70L1N10 in Table 2). The templates and primers for each PCR were shown in Table 2, and, the amplification conditions for PCR for amplifying the short fragment were as followed: denaturation at 94° C. for 10 min; 25 cycles (denaturation at 94° C. for 50 sec, annealing at a given temperature for a certain period of time, and extension at 72° C. for 1 min); and final extension at 72° C. for 10 min. The amplification conditions for PCR for amplifying the long fragment were as followed: denaturation at 94° C. for 10 min; 25 cycles (denaturation at 94° C. for 50 sec, annealing at a given temperature for a certain period of time, and extension at 72° C. for 7.5 min); and final extension at 72° C. for 10 min. The sequences of the PCR primers used were listed in Table 3. The amplification product was subjected to electrophoresis, the fragment of interest was then recovered by using DNA Extraction Kit (BEYOTIME, Cat. No. D0033), and its concentration was determined. The short fragment and long fragment obtained by amplification were mixed at a molar ratio of 2:1 (a total volume of 3 μL), and 3 μL of 2× Gibson Assembly Master Mix (purchased from NEB, containing T5 exonuclease, Phusion DNA polymerase, Taq DNA ligase) was then added, and reacted at 50° C. for 1 h.

The assembled product (6 μL) was used to transform 40 μL competent *E. coli* ER2566 (purchased from New England Biolabs) prepared by the Calcium chloride method. The transformed *E. coli* were spread onto solid LB medium containing kanamycin, and were subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 17, 18, 19, 20, 21, 22, 23, and 24, respectively, and their encoded amino acid sequences were SEQ ID NO: 5, 6, 7, 8, 9, 10, 11, and 12, respectively (the corresponding proteins were designated as H39N15-68T2, H39N15-68T3, H39N15-68T4, H39N15-68T5, H39N15-68T4-7051, H39N15- 68T4-7052, H39N15-68T4-7053, and H39N15-68T4-7055, respectively).

The mutated protein H39N15-68T2 differs from HPV39N15 by: the substitution of the amino acid residues from positions 117-150 of wild type HPV39 L1 protein with the amino acid residues from positions 117-151 of wild type HPV68 L1 protein. The mutated protein H39N15-68T3 differs from HPV39N15 by: the substitution of the amino acid residues from positions 169-181 of wild type HPV39 L1 protein with the amino acid residues from positions 170-182 of wild type HPV68 L1 protein. The mutated protein H39N15-68T4 differs from HPV39N15 by: the substitution of the amino acid residues from positions 269-288 of wild type HPV39 L1 protein with the amino acid residues from positions 270-289 of wild type HPV68 L1 protein. The mutated protein H39N15-68T5 differs from HPV39N15 by: the substitution of the amino acid residues from positions 347-358 of wild type HPV39 L1 protein with the amino acid residues from positions 348-359 of wild type HPV68 L1 protein.

The mutated protein H39N15-68T4-7051 differs from HPV39N15 by: the substitution of the amino acid residues from positions 269-288 of wild type HPV39 L1 protein with the amino acid residues from positions 270-289 of wild type HPV68 L1 protein, and the substitution of the amino acid residues from positions 53-61 of wild type HPV39 L1 protein with the amino acid residues from positions 53-61 of wild type HPV70 L1 protein. The mutated protein H39N15-68T4-7052 differs from HPV39N15 by: the substitution of the amino acid residues from positions 269-288 of wild type HPV39 L1 protein with the amino acid residues from positions 270-289 of wild type HPV68 L1 protein, and the substitution of the amino acid residues from positions 117-140 of wild type HPV39 L1 protein with the amino acid residues from positions 117-141 of wild type HPV70 L1 protein. The mutated protein H39N15-68T4-7053 differs from HPV39N15 by: the substitution of the amino acid residues from positions 269-288 of wild type HPV39 L1 protein with the amino acid residues from positions 270-289 of wild type HPV68 L1 protein, and the substitution of the amino acid residues from positions 169-181 of wild type HPV39 L1 protein with the amino acid residues from positions 170-182 of wild type HPV70 L1 protein. The mutated protein H39N15-68T4-7055 differs from HPV39N15 by: the substitution of the amino acid residues from positions 269-288 of wild type HPV39 L1 protein with the amino acid residues from positions 270-289 of wild type HPV68 L1 protein, and the substitution of the amino acid residues from positions 347-358 of wild type HPV39 L1 protein with the amino acid residues from positions 348-359 of wild type HPV70 L1 protein.

TABLE 2

PCR templates and primers for constructing expression vectors

| Template | Upstream primer | Downstream primer | Product | Temperature/Time of annealing |
|---|---|---|---|---|
| 39L1N15 | H39N15-68T1-F | H39N15-68T1-R | H39N15-68T1 | 56° C./50 s |
| 39L1N15 | G-V-H39N15-68T2-F | G-V-H39N15-68T2-R | H39N15-68T2 long fragment | 56° C./50 s |
| 39L1N15 | G-V-H39N15-68T3-F | G-V-H39N15-68T3-R | H39N15-68T3 long fragment | 56° C./50 s |
| 39L1N15 | G-V-H39N15-68T4-F | G-V-H39N15-68T4-R | H39N15-68T4 long fragment | 56° C./50 s |
| 39L1N15 | G-V-H39N15-68T5-F | G-V-H39N15-68T5-R | H39N15-68T5 long fragment | 56° C./50 s |
| 68L1N0 | G-H39N15-68T2-F | G-H39N15-68T2-R | H39N15-68T2 short fragment | 56° C./30 s |
| 68L1N0 | G-H39N15-68T3-F | G-H39N15-68T3-R | H39N15-68T3 short fragment | 56° C./30 s |
| 68L1N0 | G-H39N15-68T4-F | G-H39N15-68T4-R | H39N15-68T4 short fragment | 56° C./30 s |
| 68L1N0 | G-H39N15-68T5-F | G-H39N15-68T5-R | H39N15-68T5 short fragment | 56° C./30 s |
| H39N15-68T4 | G-V-H39N15-68T4-70S1-F | G-V-H39N15-68T4-70S1-R | H39N15-68T4-70S1 long fragment | 56° C./50 s |
| H39N15-68T4 | G-V-H39N15-68T4-70S2-F | G-V-H39N15-68T4-70S2-R | H39N15-68T4-70S2 long fragment | 56° C./50 s |
| H39N15-68T4 | G-V-H39N15-68T4-70S3-F | G-V-H39N15-68T4-70S3-R | H39N15-68T4-70S3 long fragment | 56° C./50 s |
| H39N15-68T4 | G-V-H39N15-68T4-70S5-F | G-V-H39N15-68T4-70S5-R | H39N15-68T4-70S5 long fragment | 56° C./50 s |
| 70L1N10 | G-H39N15-68T4-70S1-F | G-H39N15-68T4-70S1-R | H39N15-68T4-70S1 short fragment | 56° C./30 s |
| 70L1N10 | G-H39N15-68T4-70S2-F | G-H39N15-68T4-70S2-R | H39N15-68T4-70S2 short fragment | 56° C./30 s |
| 70L1N10 | G-H39N15-68T4-70S3-F | G-H39N15-68T4-70S3-R | H39N15-68T4-70S3 short fragment | 56° C./30 s |
| 70L1N10 | G-H39N15-68T4-70S5-F | G-H39N15-68T4-70S5-R | H39N15-68T4-70S5 short fragment | 56° C./30 s |

TABLE 3

Sequences of the primers used (SEQ ID NOs: 38-71)

| SEQ ID NO: | Primer name | Primer sequence (5'-3') |
|---|---|---|
| 38 | H39N15-68T1-F | TTCAAGGTCCCCATGAGCGGCGGGCGCAAGCAGGATATCCCCAAGGTC |
| 39 | H39N15-68T1-R | CCCGCCGCTCATGGGGACCTTGAAGTAGGGGTGGCCCACGGTCAGCAG |
| 40 | G-V-H39N15-68T2-F | GACTTCGACGCCCACGCAGGCCCA |
| 41 | G-V-H39N15-68T2-R | AAGCAGACCCAGCTCTGTATCATC |
| 42 | G-V-H39N15-68T3-F | TTCGCCGATTGCTGGGACGCACCC |
| 43 | G-V-H39N15-68T3-R | CTGGAGCTGGTGAATACACCCATC |
| 44 | G-V-H39N15-68T4-F | GTGGCGGGCGAAGAGCTGCTCGCG |
| 45 | G-V-H39N15-68T4-R | TGTCCAAGCCCATCCGGCAGCATG |
| 46 | G-V-H39N15-68T5-F | GCTTGTGCTCAGGGTGAAATTTGTGGAGCG |
| 47 | G-V-H39N15-68T5-F | TTCAAGGAGTACACACGCCACGTCGAAGAA |
| 48 | G-H39N15-68T2-F | TGGGCCTGCGTGGGCGTCGAAGTCGGCAGAGGCCAGCCCCTGGGC |
| 49 | G-H39N15-68T2-R | GATGATACAGAGCTGGGTCTGCTTGCAGTCCACGGCCACGTTGTC |
| 50 | G-H39N15-68T3-F | GGGTGCGTCCCAGCAATCGGCGAACACTGGGCCAAGGGCAAGAGC |

TABLE 3-continued

Sequences of the primers used (SEQ ID NOs: 38-71)

| SEQ ID NO: | Primer name | Primer sequence (5'-3') |
|---|---|---|
| 51 | G-H39N15-68T3-R | GATGGGTGTATTCACCAGCTCCAGAGGGGGCAGTCGCCCTGCTG |
| 52 | G-H39N15-68T4-F | CGCGAGCAGCTCTTCGCCCGCCACTTCTGGAACAGAGGCGGCATG |
| 53 | G-H39N15-68T4-R | CATGCTGCCGGATGGGCTTGGACAGTACACGTAGCTGCTGGGTGT |
| 54 | G-H39N15-68T5-F | CGCTCCACAAATTTCACCCTGAGCACAAGCACCGACAGCACCGTGCCCGCC |
| 55 | G-H39N15-68T5-R | TTCTTCGACGTGGCGTGTGTACTCCTTGAACTTATTGCTGTCGTACACGGC |
| 56 | G-V-H39N15-68T4-70S1-F | GTAGGGGTGGCCCACGGTCAG |
| 57 | G-V-H39N15-68T4-70S1-R | GCCTACCAGTACCGCGTGTTC |
| 58 | G-V-H39N15-68T4-70S2-F | GACTTCGACGCCCACGCAGGC |
| 59 | G-V-H39N15-68T4-70S2-R | AAGCAGACCCAGCTCTGTATC |
| 60 | G-V-H39N15-68T4-70S3-F | TTCGCCGATTGCTGGGACGCA |
| 61 | G-V-H39N15-68T4-70S3-R | CTGGAGCTGGTGAATACACCC |
| 62 | G-V-H39N15-68T4-70S5-F | GCTTGTGCTCAGGGTGAAATT |
| 63 | G-V-H39N15-68T4-70S5-R | TTCAAGGAGTACACACGCCAC |
| 64 | G-H39N15-68T4-70S1-F | CTGACCGTGGGCCACCCCTACTTTAAGGTACCTGTAAATGGT |
| 65 | G-H39N15-68T4-70S1-R | GAACACGCGGTACTGGTAGGCAGACACCTTAGGTATTTCCTG |
| 66 | G-H39N15-68T4-70S2-F | GCCTGCGTGGGCGTCGAAGTCGGTAGAGGCCAGCCATTGGGC |
| 67 | G-H39N15-68T4-70S2-R | GATACAGAGCTGGGTCTGCTTATAGTCCACAGACACATTGTC |
| 68 | G-H39N15-68T4-70S3-F | TGCGTCCCAGCAATCGGCGAACACTGGGCAAAGGCAAGGCC |
| 69 | G-H39N15-68T4-70S3-R | GGGTGTATTCACCAGCTCCAGTGGTGGACAATCGCCCTGTTGTAC |
| 70 | G-H39N15-68T4-70S5-F | AATTTCACCCTGAGCACAAGCACCGAAACAGCCATACCTGCT |
| 71 | G-H39N15-68T4-70S5-R | GTGGCGTGTGTACTCCTTGAACTTTGTAGGGCTATATACAGC |

Expression of the Mutated Proteins on a Large Scale

The E. coli solutions comprising the recombinant plasmid pTO-T7-H39N15-68T1, pTO-T7-H39N15-68T2, pTO-T7-H39N15-68T3, pTO-T7-H39N15-68T4, pTO-T7-H39N15-68T5, pTO-T7-H39N15-68T4-70S1, pTO-T7-H39N15-68T4-70S2, pTO-T7-H39N15-68T4-70S3, and pTO-T7-H39N15-68T4-70S5, respectively, were taken from −70° C. refrigerator, were inoculated in 100 mL LB liquid medium containing kanamycin, and incubated at 200 rpm and 37° C. for about 8 h. Then, the culture was transferred to 500 mL LB medium containing kanamycin (1 ml bacterial solution was transferred), and was further incubated. When the bacterial concentration reached an OD600 of about 0.6, the culturing temperature was lowered to 25° C. and 500 μL IPTG was added to each culture bottle. The incubation was further performed for 8 h. After the incubation was finished, the bacteria were collected by centrifugation. The bacteria expressing H39N15-68T1, H39N15-68T2, H39N15-68T3, H39N15-68T4, H39N15-68T5, H39N15-68T4-70S1, H39N15-68T4-70S2, H39N15-68T4-70S3 and H39N15-68T4-70S5 protein were obtained, respectively.

Disruption of Bacteria Expressing the Mutated Proteins

The bacteria obtained were re-suspended at a ratio of 1 g bacteria to 10 mL lysis buffer (20 mM Tris buffer, pH7.2, 300 mM NaCl). The bacteria were disrupted by using an ultrasonic apparatus for 30 min. The lysis solution containing the disrupted bacteria were centrifuged at 13500 rpm (30000 g) for 15 min, and the supernatant (i.e. the supernatant of disrupted bacteria) was obtained.

Chromatographic Purification of the Mutated Protein

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.), CHT-II (purchased from Bio-RAD) and Butyl Sepharose 4 Fast Flow (GE Healthcare Co.)

Buffer: Buffer A (20 mM phosphate buffer, pH8.0, 20 mM DTT); and Buffer B (20 mM phosphate buffer, pH8.0, 20 mM DTT, 2 M NaCl). The buffers containing different concentrations of NaCl used in the following elution protocol were prepared by mixing Buffer A and Buffer B at a certain ratio.

Sample: the supernatants of disrupted bacteria containing H39N15-68T1, H39N15-68T2, H39N15-68T3, H39N15-68T4, H39N15-68T5, H39N15-68T4-70S1, H39N15-68T4-70S2, H39N15-68T4-70S3, and H39N15-68T4-70S5, respectively, as obtained above.

Elution Protocol:

(1) Cation exchange purification of the supernatant of disrupted bacteria by SP Sepharose 4 Fast Flow: the sample was loaded on the column, undesired proteins were then eluted with a buffer containing 400 mM NaCl (80% Buffer A+20% Buffer B), followed by the elution of the protein of interest with a buffer containing 800 mM NaCl (60% Buffer A+40% Buffer B), and the fraction eluted with the buffer containing 800 mM NaCl was collected;

(2) Chromatographic purification of the elution fraction obtained in the step (1) by CHTII (hydroxyapatite chromatography): the elution fraction obtained in the step (1) was diluted so that the NaCl concentration was decreased to 0.5 M; the sample was loaded on the column, undesired proteins were then eluted with a buffer containing 500 mM NaCl (75% Buffer A+25% Buffer B), followed by the elution of the protein of interest with a buffer containing 1000 mM NaCl (50% Buffer A+50% Buffer B), and the fraction eluted with the buffer containing 1000 mM NaCl was collected;

(3) Chromatographic purification of the elution fraction obtained in the step (2) by HIC (hydrophobic interaction chromatography): the sample was loaded on the column, undesired proteins were then eluted with a buffer containing 1000 mM NaCl, followed by the elution of the protein of interest with a buffer containing 200 mM NaCl (90% Buffer A+10% Buffer B), and the fraction eluted with the buffer containing 200 mM NaCl was collected.

Figure 1:
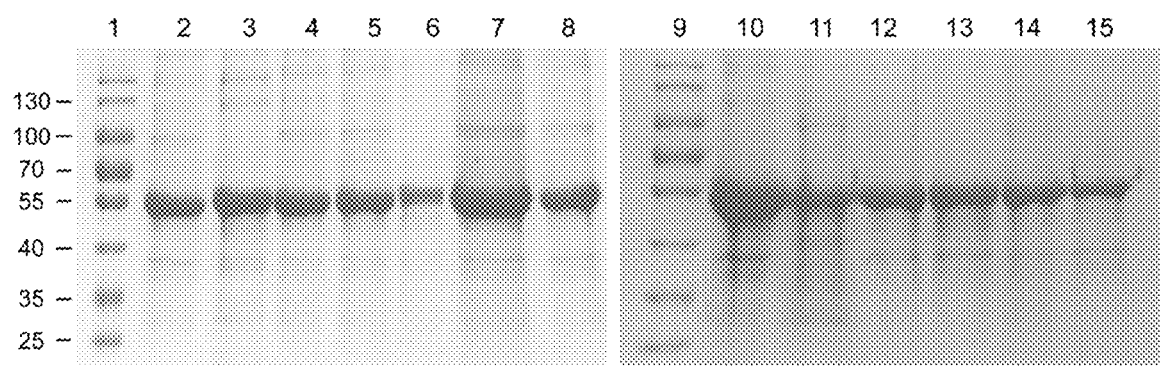
FIG. 1 shows the SDS-PAGE result of the purified mutated proteins in Example 1. Lane 1: protein molecular weight marker; Lane 2: HPV39N15 (HPV39 L1 protein having 15 amino acids truncated at N-terminal); Lane 3: HPV68N0 (HPV68 L1 protein having 0 amino acids truncated at N-terminal, i.e., full-length wild type HPV68 L1 protein); Lane 4: H39N15-68T1; Lane 5: H39N15-68T2; Lane 6: H39N15-68T3; Lane 7: H39N15-68T4; Lane 8: H39N15-68T5; Lane 9: protein molecular weight marker; Lane 10: H39N15-68T4; Lane 11: HPV70N10 (HPV70 L1 protein having 10 amino acids truncated at N-terminal); Lane 12: H39N15-68T4-70S1; Lane 13: H39N15-68T4-70S2; Lane 14: H39N15-68T4-70S3; Lane 15: H39N15-68T4-70S5. The result showed that after chromatographic purification, H39N15-68T1, H39N15-68T2, H39N15-68T3, H39N15-68T4, H39N15-68T5, H39N15-68T4-70S1, H39N15-68T4-70S2, H39N15-68T4-70S3, and H39N15-68T4-70S5 protein reached a purity of above 90%.

150 μL of elution fraction obtained in the step (3) was added to 30 μL of 6× Loading Buffer (1 L of which contained 300 ml of 1 M TB 6.8, 600 ml of 100% glycerol, 120 g of SDS, 6 g of bromophenol blue, and 50 ml of β-mercaptoethanol). The resultant solution was mixed well and incubated in 80° C. water bath for 10 min. 10 μl of the resultant sample was then subjected to 10% SDS-PAGE at 120V for 120 min; and the electrophoretic bands were stained by Coomassie brilliant blue. The electrophoretic result was shown in FIG. 1. The result showed that after said purification steps, H39N15-68T1, H39N15-68T2, H39N15-68T3, H39N15-68T4, H39N15-68T5, H39N15-68T4-70S1, H39N15-68T4-70S2, H39N15-68T4-70S3, and H39N15-68T4-70S5 protein had a purity of above 90%.

By similar methods, HPV39N15 protein was prepared and purified by using *E. coli* and the plasmid pTO-T7-HPV39N15; HPV68N0 protein was prepared and purified by using *E. coli* and the plasmid pTO-T7-HPV68L1N0; and HPV70N10 protein was prepared and purified by using *E. coli* and the plasmid pTO-T7-HPV70N10.

Western Blot Assay of the Mutated Proteins

Figure 2:
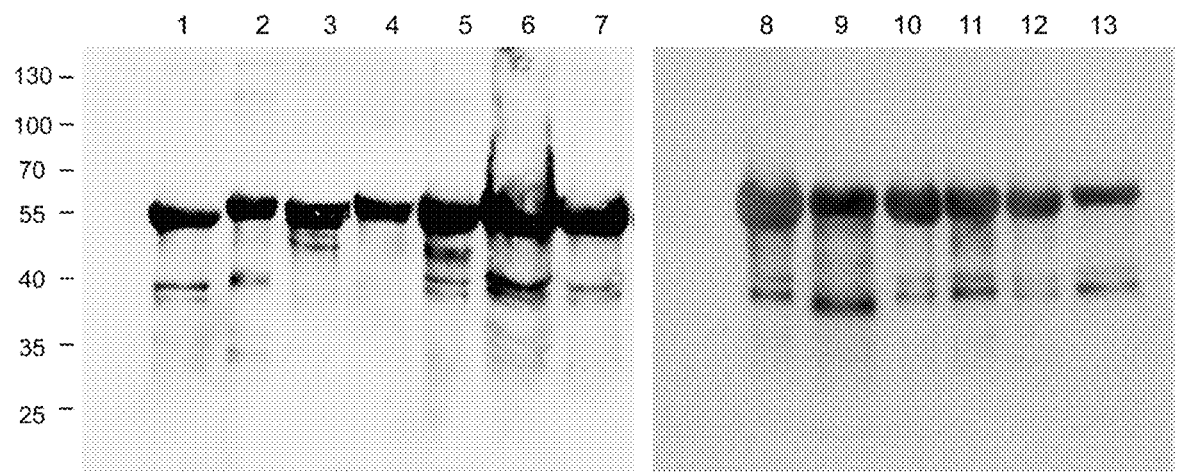
FIG. 2 shows the Western Blot result of the mutated proteins H39N15-68T1, H39N15-68T2, H39N15-68T3, H39N15-68T4, H39N15-68T5, H39N15-68T4-7051, H39N15-68T4-7052, H39N15-68T4-7053, and H39N15-68T4-7055 prepared in Example 1, as determined by using a broad-spectrum antibody 4B3. Lane 1: HPV39N15; Lane 2: HPV68N0; Lane 3: H39N15-68T1; Lane 4: H39N15-68T2; Lane 5: H39N15-68T3; Lane 6: H39N15-68T4; Lane 7: H39N15-68T5; Lane 8: H39N15-68T4; Lane 9: HPV70N10; Lane 10: H39N15-68T4-70S1; Lane 11: H39N15-68T4-7052; Lane 12: H39N15-68T4-7053; Lane 13: H39N15-68T4-7055. The result showed that the mutated proteins H39N15-68T1, H39N15-68T2, H39N15-68T3, H39N15-68T4, H39N15-68T5, H39N15-68T4-7051, H39N15-68T4-7052, H39N15-68T4-7053, and H39N15-68T4-7055 could be specifically recognized by the broad-spectrum antibody 4B3.

The H39N15-68T1, H39N15-68T2, H39N15-68T3, H39N15-68T4, H39N15-68T5, H39N15-68T4-70S1, H39N15-68T4-70S2, H39N15-68T4-70S3, and H39N15-68T4-70S5 protein purified by the method above were subjected to electrophoresis. After electrophoresis, Western Blot assay was carried out by using a broad-spectrum antibody 4B3 against HPV L1 protein, and the result was shown in FIG. 2. The result showed that H39N15-68T1, H39N15-68T2, H39N15-68T3, H39N15-68T4, H39N15-68T5, H39N15-68T4-70S1, H39N15-68T4-70S2, H39N15-68T4-70S3 and H39N15-68T4-70S5 could be specifically recognized by the broad-spectrum antibody 4B3.

Example 2: Assembly of HPV Virus-Like Particles and Morphological Detection of Particles Assembly of HPV Virus-Like Particles A given volume (about 2 ml) of the protein H39N15-68T1, H39N15-68T2, H39N15-68T3, H39N15-68T4, H39N15-68T5, H39N15-68T4-70S1, H39N15-68T4-70S2, H39N15-68T4-70S3 or H39N15-68T4-70S5 was dialyzed to (1) 2 L storage buffer (20 mM sodium phosphate buffer pH 6.5, 0.5 M NaCl); (2) 2 L renaturation buffer (50 mM sodium phosphate buffer pH 6.0, 2 mM $CaCl_2$, 2 mM $MgCl_2$, 0.5 M NaCl); and (3) 20 mM sodium phosphate buffer pH 7.0, 0.5 M NaCl, successively. The dialysis was performed in each of the three buffers for 12 h.

By similar methods, the HPV39N15, HPV68N0 and HPV70N10 protein were assembled into HPV39N15 VLP, HPV68N0 VLP and HPV70N10 VLP, respectively.

Molecular Sieve Chromatographic Analysis

Figure 3:
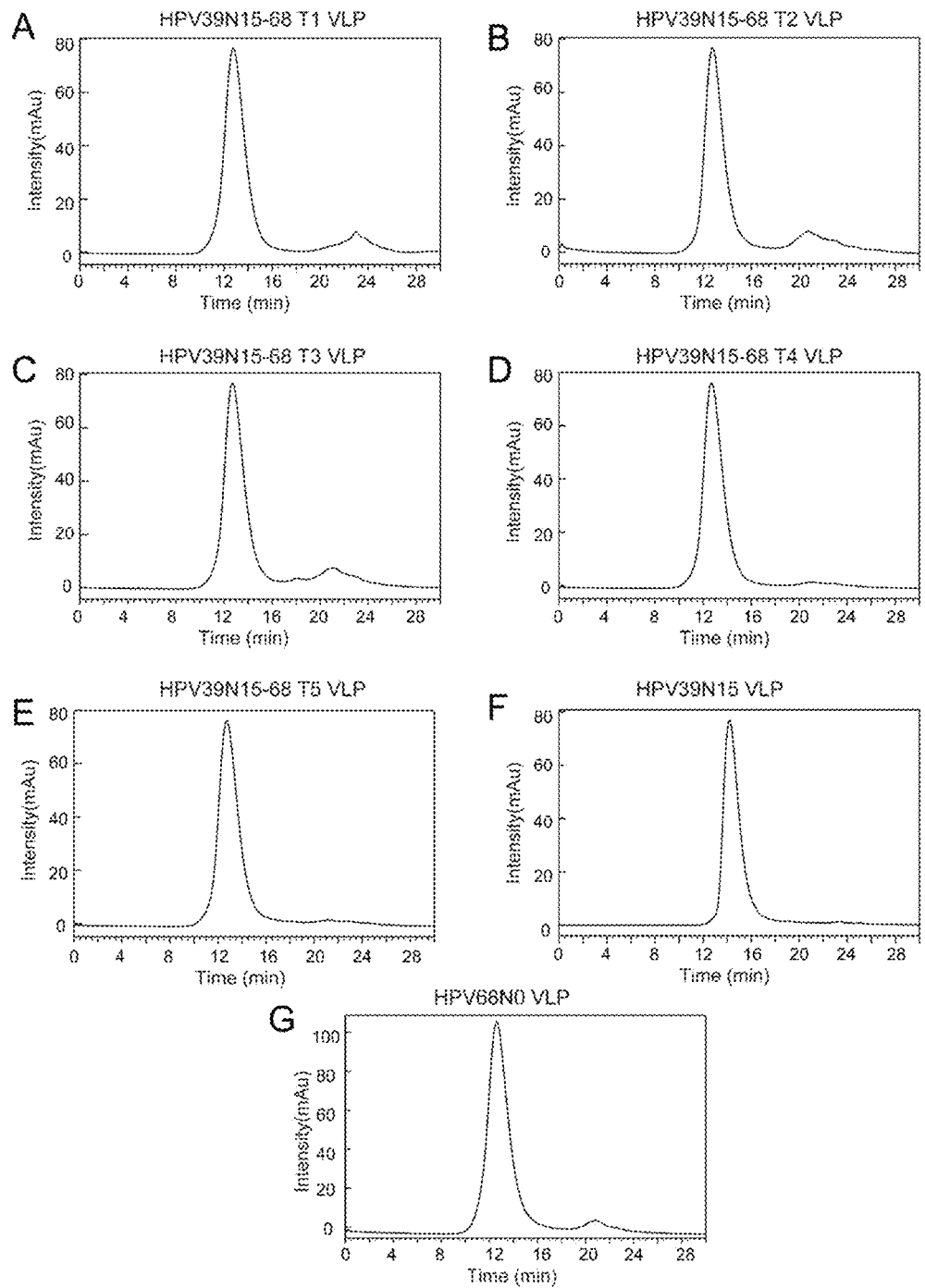
FIG. 3 shows the results of the samples comprising the protein HPV39N15, H39N15-68T1, H39N15-68T2, H39N15-68T3, H39N15-68T4, and H39N15-68T5, as analyzed by molecular sieve chromatography. The results showed that the first protein peak of the samples comprising the protein H39N15-68T1, H39N15-68T2, H39N15-68T3, H39N15-68T4, or H39N15-68T5 appeared at about 13-14 min, which was comparable to that of HPV39N15. This showed that all these proteins were able to assemble into VLPs.
Figure 4:
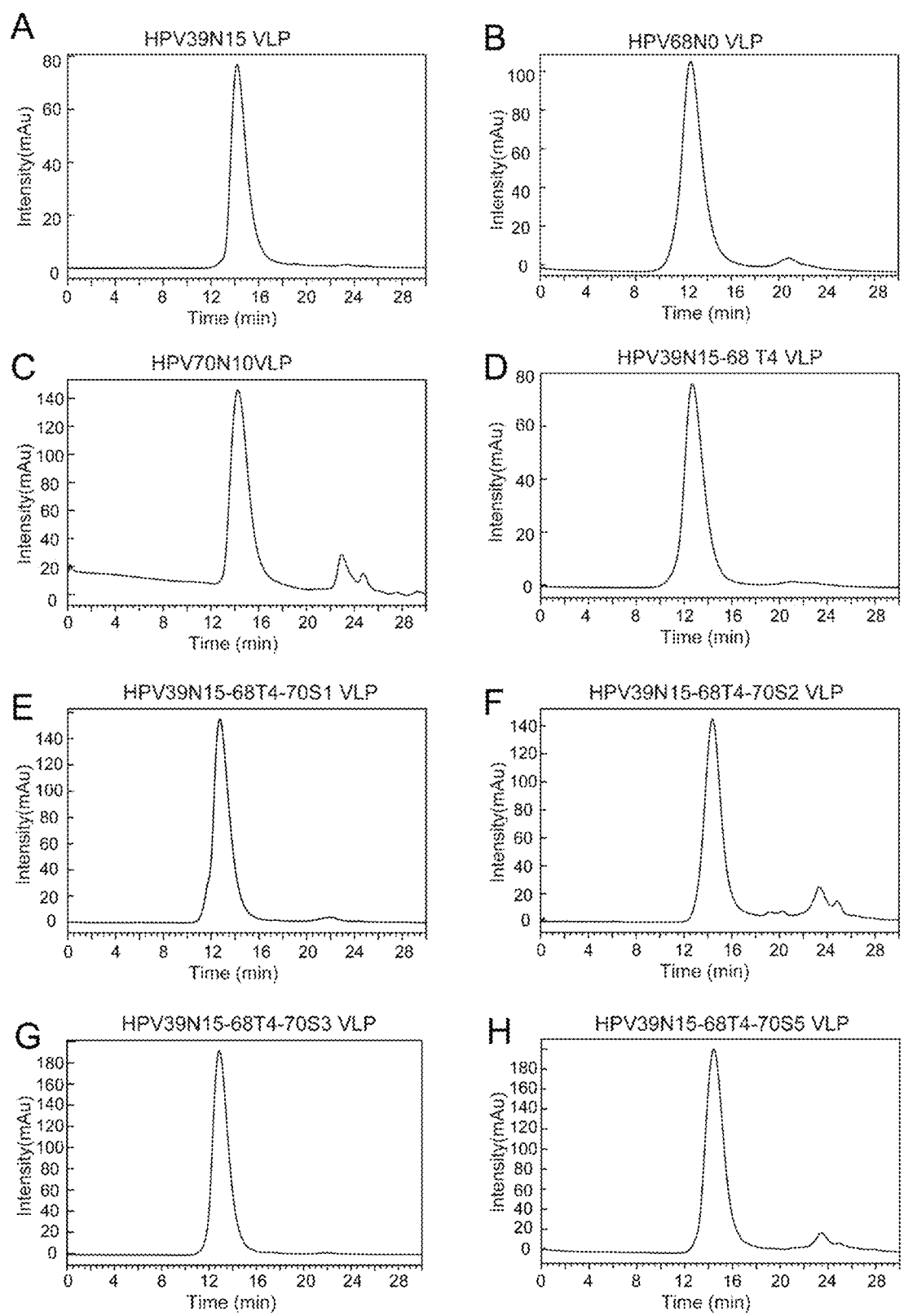
FIG. 4 shows the results of the samples comprising the protein HPV39N15, HPV68L1N0, HPV70N10, H39N15-68T4, H39N15-68T4-70S1, H39N15-68T4-70S2, H39N15-68T4-70S3, and H39N15-68T4-70S5, as analyzed by molecular sieve chromatography. The results showed that the first protein peak of the samples comprising the protein H39N15-68T4-70S1, H39N15-68T4-70S2, H39N15-68T4-70S3, or H39N15-68T4-70S5 appeared at about 13-14 min, which was comparable to that of HPV39N15, HPV68L1N0, HPV70N10 and H39N15-68T4 VLP. This showed that all these proteins were able to assemble into VLPs.
Figures 5A, 5B:
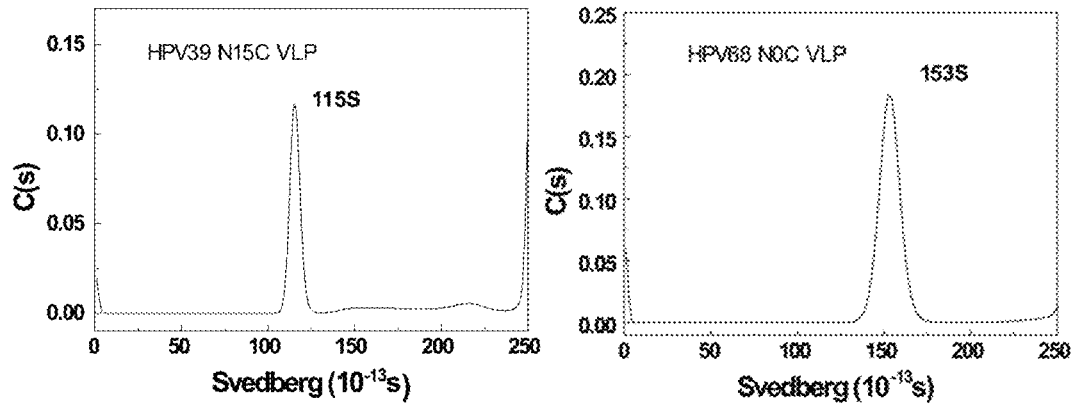
FIGS. 5A-5L show the results of sedimentation velocity analysis of HPV39N15 VLP, HPV68L1N0 VLP, HPV70N10 VLP, H39N15-68T1 VLP, H39N15-68T2 VLP, H39N15-68T3 VLP, H39N15-68T4 VLP, H39N15-68T5 VLP, H39N15-68T4-70S1 VLP, H39N15-68T4-70S2 VLP, H39N15-68T4-70S3 VLP and H39N15-68T4-70S5 VLP.
Figures 5C, 5D:
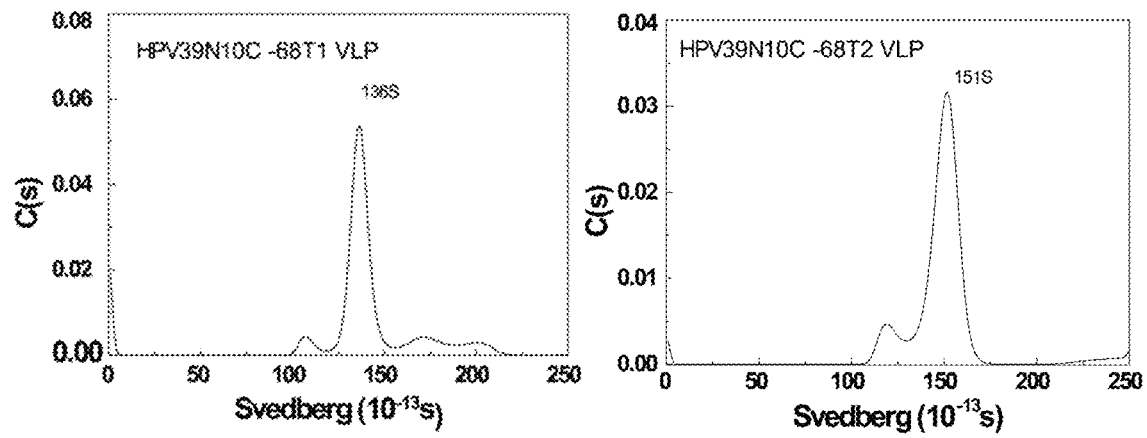
Figures 5E, 5F:
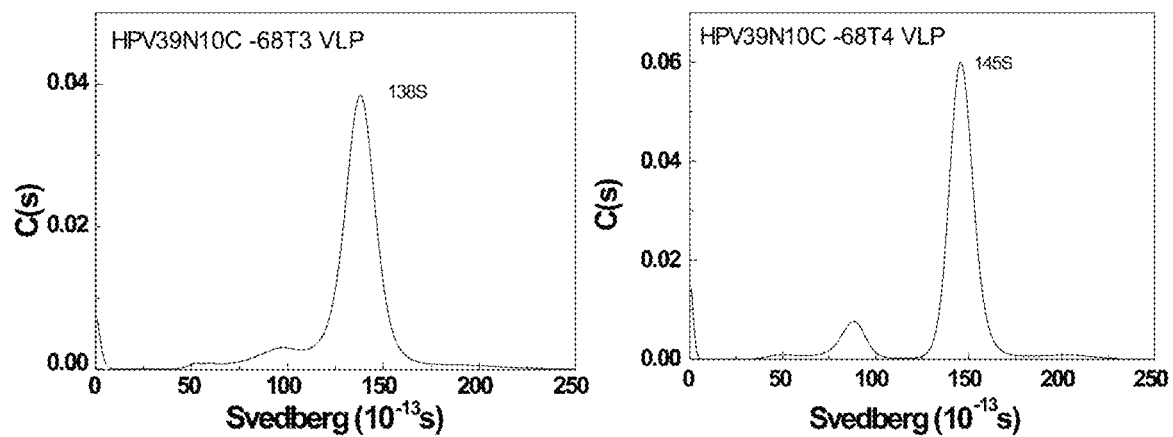
Figures 5G, 5H:
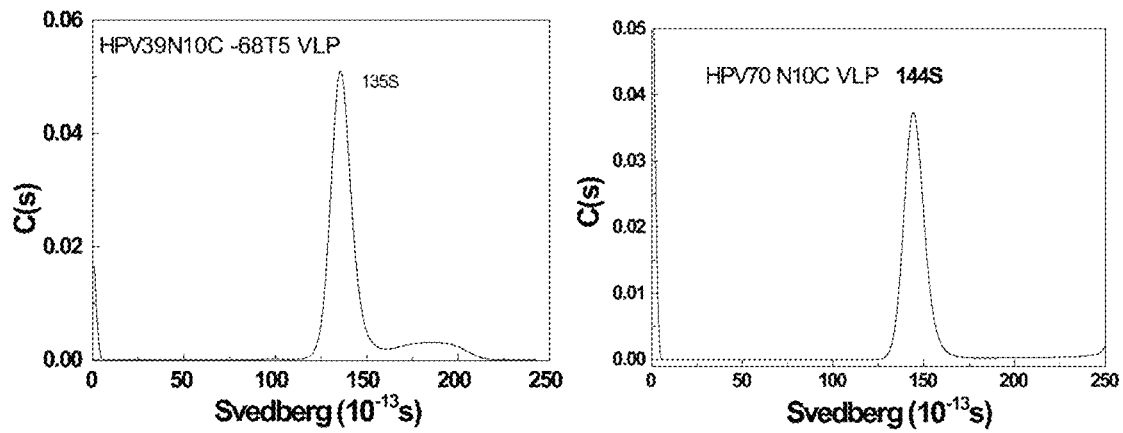
Figures 5I, 5J:
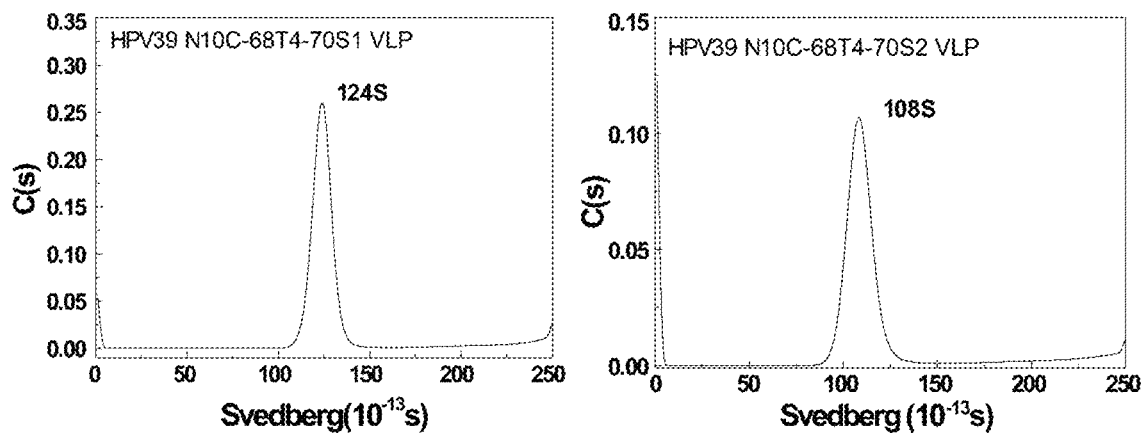
Figures 5K, 5L:
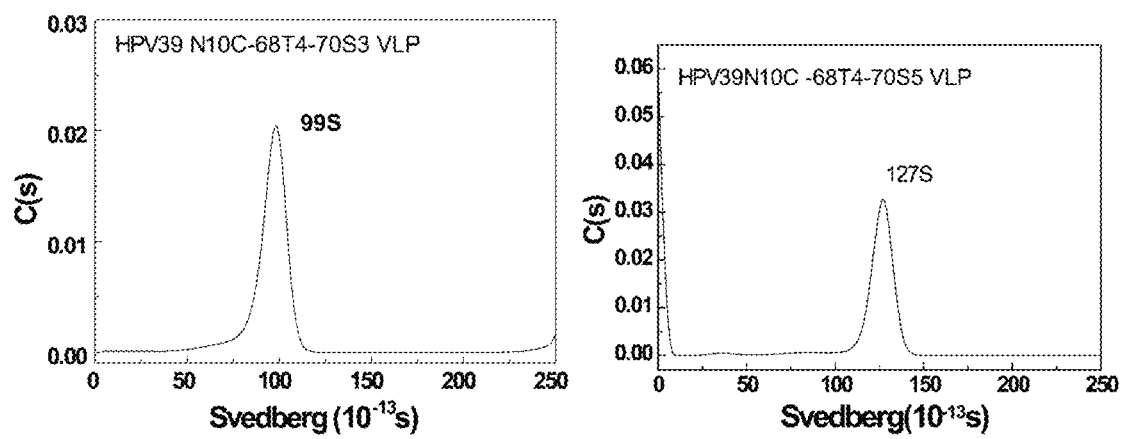
Figure 6A:
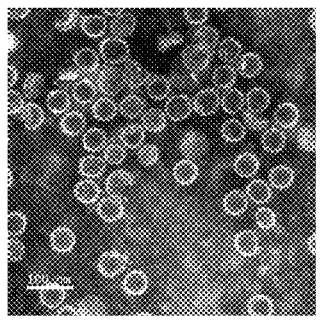
FIGS. 6A-6L show the transmission electron microscopy (TEM) photographs (taken at 100,000× magnification, Bar=0.1 μm) of various VLP samples.
Figure 6B:
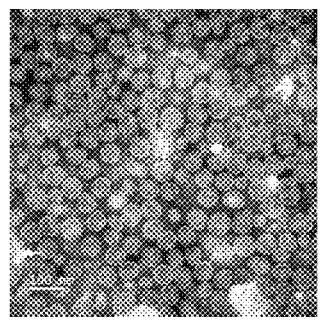
Figure 6C:
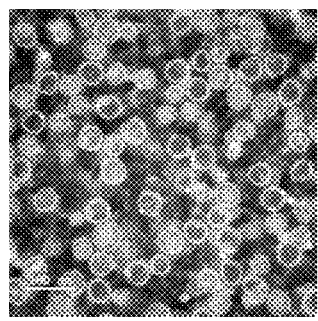
Figure 6D:
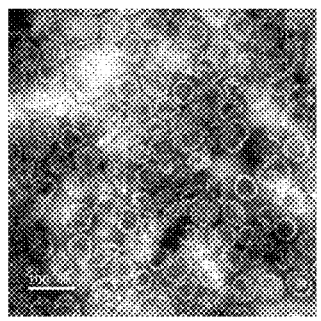
Figure 6E:
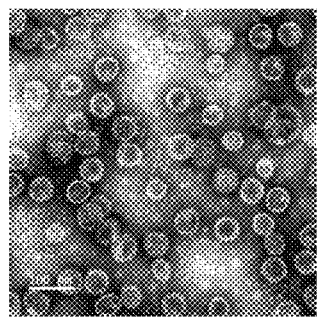
Figure 6F:
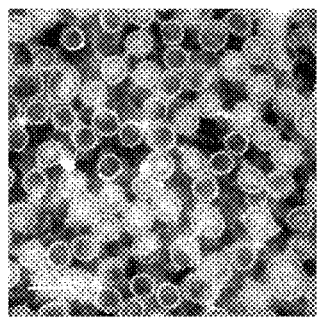
Figure 6G:
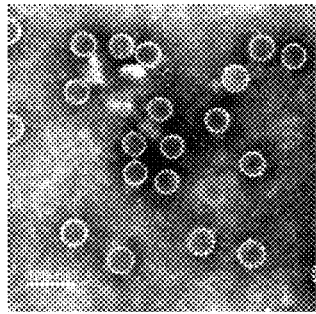
Figure 6H:
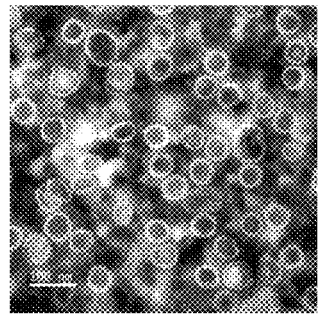
Figure 6I:
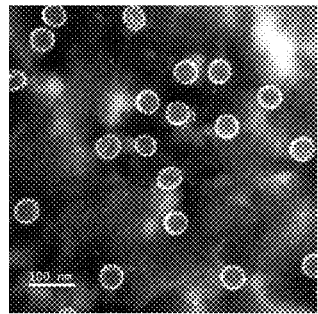
Figure 6J:
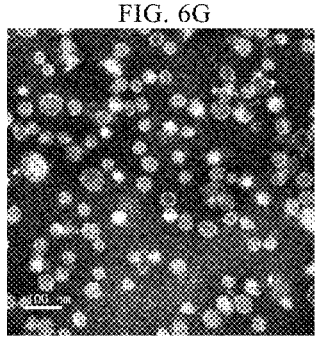
Figure 6K:
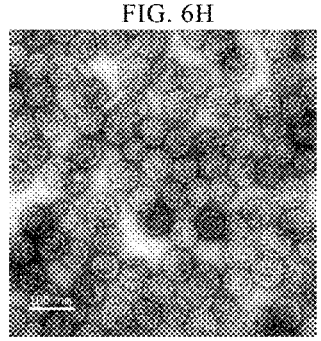
Figure 6L:
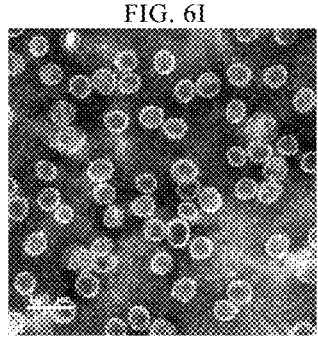

The dialyzed sample was subjected to molecular sieve chromatographic analysis by 1120 Compact LC High Performance Liquid Chromatographic System (Agilent Technologies), wherein the analytical column used was TSK Gel PW5000×17.8×300 mm. The analysis results were shown in FIGS. 3 and 4. The results showed that the first protein peak of the samples comprising the protein H39N15-68T1, H39N15-68T2, H39N15-68T3, H39N15-68T4, H39N15-68T5, H39N15-68T4-7051, H39N15-68T4-7052, H39N15-68T4-7053 or H39N15-68T4-7055 appeared at about 13-14 min, which was comparable to that of HPV39N15 VLP, HPV68N0 VLP and HPV70N10 VLP. This showed that all these protein were able to assemble into VLPs.

Sedimentation Velocity Analysis

The apparatus for sedimentation velocity analysis was Beckman XL-A Analytical Ultracentrifuge, equipped with optical inspection system and An-50Ti and An-60Ti rotor. The sedimentation coefficients of HPV39N15 VLP, HPV68N0 VLP, HPV70N10 VLP, H39N15-68T1 VLP, H39N15-68T2 VLP, H39N15-68T3 VLP, H39N15-68T4 VLP, H39N15-68T5 VLP, H39N15-68T4-7051 VLP, H39N15-68T4-7052 VLP, H39N15-68T4-7053 VLP and H39N15-68T4-7055 VLP were analyzed by sedimentation velocity method. The results were shown in FIGS. 5A-5L. The results showed that the sedimentation coefficient of H39N15-68T1 VLP, H39N15-68T2 VLP, H39N15-68T3 VLP, H39N15-68T4 VLP, H39N15-68T5 VLP, H39N15-68T4-70S1 VLP, H39N15-68T4-70S2 VLP, H39N15-68T4-70S3 VLP and H39N15-68T4-70S5 VLP was 136S, 151S, 138S, 145S, 135S, 124S, 108S, 99S and 127S, respectively. This showed that the mutated protein H39N15-68T1, H39N15-68T2, H39N15-68T3, H39N15-68T4, H39N15-68T5, H39N15-68T4-70S1, H39N15-68T4-70S2, H39N15-68T4-70S3 and H39N15-68T4-70S5 prepared above were able to assemble into virus-like particles that were similar to wild type VLP (HPV39N15 VLP, 115S; HPV68N0 VLP, 153S; HPV70N10 VLP, 144S) in terms of size and morphology.

Morphological Test of Virus-Like Particles

A 100 μL sample comprising VLP was observed by transmission electron microscope (TEM). The apparatus used was a 100 kV Transmission Electron Microscope supplied by JEOL Ltd. (100,000× magnification). In brief, a 13.5 μL of sample was negatively stained with 2% phosphotungstic acid (pH 7.0), fixed on a carbon-coated copper grid, and then observed by TEM. The results were shown in FIGS. 6A-6L. The results showed that the mutated protein H39N15-68T1, H39N15-68T2, H39N15-68T3, H39N15-68T4, H39N15-68T5, H39N15-68T4-70S1, H39N15-68T4-70S2, H39N15-68T4-70S3 and H39N15-68T4-70S5 were able to assemble into virus-like particles, and the virus-like particles assembled by these mutated proteins were uniform in size, and had a radius of about 25-30 nm. The virus-like particles assembled by the wild type HPV39N15, HPV68N0 and HPV70N10 also had a radius of about 25-30 nm, and were uniform in size. This indicated that these mutated proteins were similar to the L1 protein of wild type HPV39, HPV68 and HPV70, and were able to assemble into VLPs with a uniform size.

Example 3: Evaluation 1 of Neutralizing Antibody Titer in Serum of Mice Vaccinated with Virus-Like Particles In this experiment, virus-like particles used were H39N15-68T1 VLP, H39N15-68T2 VLP, H39N15-68T3 VLP, H39N15-68T4 VLP and H39N15-68T5 VLP.

In this experiment, vaccination schedule was shown in Table 4. All the mice (6-week old BalB/c female mice) were divided into 3 groups: Aluminum adjuvant group 1 (at an immunizing dose of 5 μg, using aluminum adjuvant), Aluminum adjuvant group 2 (at an immunizing dose of 1 μg, using aluminum adjuvant), and Aluminum adjuvant group 3 (at an immunizing dose of 0.2 μg, using aluminum adjuvant). Each group was further divided into 8 subgroups. The Control subgroups 1 and 2 were vaccinated with HPV39N15 VLP alone and HPV68N0 VLP alone, respectively, the Control subgroup 3 was vaccinated with the mixed HPV39/HPV68 VLP (i.e. a mixture of HPV39N15 VLP and HPV68N0 VLP, at a given immunizing dose for each VLP). The Experimental subgroups 1, 2, 3, 4 and 5 were vaccinated with H39N15-68T1 VLP, H39N15-68T2 VLP, H39N15-68T3 VLP, H39N15-68T4 VLP and H39N15-68T5 VLP, respectively.

In Aluminum adjuvant groups 1-3, 5 mice/subgroup were vaccinated by intraperitoneal injection, at an immunizing dose 5 μg, 1 μg, and 0.2 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV39 and HPV68 in serum were analyzed. The analysis results were shown in FIGS. 7A-7C. The results showed that H39N15-68T4 VLP could induce the generation of high-titer neutralizing antibodies against HPV39 in mice, and its protective effect was slightly weaker than that of HPV39N15 VLP alone at the same dose, but was significantly superior to that of HPV68N0 VLP alone at the same dose; and it could induce the generation of high-titer neutralizing antibodies against HPV68 in mice, and its protective effect was slightly weaker than that of HPV68N0 VLP alone at the same dose, but was significantly superior to that of HPV39N15 VLP alone at the same dose. This showed that H39N15-68T4 VLP had good cross-immunogenicity and cross-protection against HPV39 and HPV68.

TABLE 4

| | Vaccination schedule | | | | |
|---|---|---|---|---|---|
| Group | Antigen for vaccination | Adjuvant | Immunizing dose | Number | Vaccination procedure (week) |
| Aluminum adjuvant group 1 | HPV39N15 VLP | aluminum adjuvant | 5 μg | 5 | 0, 2, 4 |
| | HPV68N0 VLP | aluminum adjuvant | 5 μg | 5 | 0, 2, 4 |
| | The mixed HPV39/HPV68 VLP | aluminum adjuvant | 5 μg for each VLP | 5 | 0, 2, 4 |
| | H39N15-68T1 VLP | aluminum adjuvant | 5 μg | 5 | 0, 2, 4 |
| | H39N15-68T2 VLP | aluminum adjuvant | 5 μg | 5 | 0, 2, 4 |
| | H39N15-68T3 VLP | aluminum adjuvant | 5 μg | 5 | 0, 2, 4 |
| | H39N15-68T4 VLP | aluminum adjuvant | 5 μg | 5 | 0, 2, 4 |
| | H39N15-68T5 VLP | aluminum adjuvant | 5 μg | 5 | 0, 2, 4 |
| Aluminum adjuvant group 2 | HPV39N15 VLP | aluminum adjuvant | 1 μg | 5 | 0, 2, 4 |
| | HPV68N0 VLP | aluminum adjuvant | 1 μg | 5 | 0, 2, 4 |
| | The mixed HPV39/HPV68 VLP | aluminum adjuvant | 1 μg for each VLP | 5 | 0, 2, 4 |
| | H39N15-68T1 VLP | aluminum adjuvant | 1 μg | 5 | 0, 2, 4 |
| | H39N15-68T2 VLP | aluminum adjuvant | 1 μg | 5 | 0, 2, 4 |
| | H39N15-68T3 VLP | aluminum adjuvant | 1 μg | 5 | 0, 2, 4 |

TABLE 4-continued

Vaccination schedule

| Group | Antigen for vaccination | Adjuvant | Immunizing dose | Number | Vaccination procedure (week) |
|---|---|---|---|---|---|
| | H39N15-68T4 VLP | aluminum adjuvant | 1 μg | 5 | 0, 2, 4 |
| | H39N15-68T5 VLP | aluminum adjuvant | 1 μg | 5 | 0, 2, 4 |
| Aluminum adjuvant group 3 | HPV39N15 VLP | aluminum adjuvant | 0.2 μg | 5 | 0, 2, 4 |
| | HPV68N0 VLP | aluminum adjuvant | 0.2 μg | 5 | 0, 2, 4 |
| | The mixed HPV39/HPV68 VLP | aluminum adjuvant | 0.2 μg for each VLP | 5 | 0, 2, 4 |
| | H39N15-68T1 VLP | aluminum adjuvant | 0.2 μg | 5 | 0, 2, 4 |
| | H39N15-68T2 VLP | aluminum adjuvant | 0.2 μg | 5 | 0, 2, 4 |
| | H39N15-68T3 VLP | aluminum adjuvant | 0.2 μg | 5 | 0, 2, 4 |
| | H39N15-68T4 VLP | aluminum adjuvant | 0.2 μg | 5 | 0, 2, 4 |
| | H39N15-68T5 VLP | aluminum adjuvant | 0.2 μg | 5 | 0, 2, 4 |

Example 4: Evaluation 1 of $ED_{50}$ of Virus-Like Particles for Inducing Seroconversion In this experiment, the virus-like particle used was H39N15-68T4 VLP. 6-Week old BalB/c female mice (8 mice) were vaccinated with aluminum adjuvant by single intraperitoneal injection, wherein H39N15-68T4 VLP (at an immunizing dose of 0.900 μg, 0.300 μg, 0.100 μg, 0.033 μg or 0.011 μg) was used in the Experimental groups, and HPV68N0 VLP alone (at an immunizing dose of 0.900 μg, 0.300 μg, 0.100 μg, 0.033 μg or 0.011 μg), HPV39N15 VLP alone (at an immunizing dose of 0.900 μg, 0.300 μg, 0.100 μg, 0.033 μg or 0.011 μg) or the mixed HPV39/HPV68 VLP (i.e. a mixture of HPV39N15 VLP and HPV68N0 VLP, at an immunizing dose of 0.900 μg, 0.300 μg, 0.100 μg, 0.033 μg or 0.011 μg for each VLP); the immunizing volume was 1 mL. In addition, the diluent used to dilute the vaccine was used as a blank control. 8 Mice were vaccinated in each group, and at Week 5 after vaccination, venous blood was collected from eyeball. Antibodies against HPV in the serum were detected, and by Reed-Muench method (Reed L J M H. A simple method of estimating fifty percent endpoints. Am J Hyg. 1938; 27:493-7), $ED_{50}$ for inducing seroconversion (i.e. inducing the generation of antibodies in mice) was calculated for each sample. The results were shown in Tables 5-8.

TABLE 5

$ED_{50}$ of HPV39N15 VLP for inducing the generation of antibodies against HPV39 and HPV68 (seroconversion) in mice

| Type | Immunizing dose (μg) | Total number of mice | Number of mice with positive conversion | Positive conversion rate | $ED_{50}$ (μg) |
|---|---|---|---|---|---|
| HPV39 | 0.900 | 8 | 8 | 100.00% | 0.019 |
| | 0.300 | 8 | 8 | 100.00% | |
| | 0.100 | 8 | 6 | 88.89% | |
| | 0.033 | 8 | 8 | 83.33% | |
| | 0.011 | 8 | 2 | 20.00% | |
| HPV68 | 0.900 | 8 | 0 | 0.00% | >0.9 |
| | 0.300 | 8 | 0 | 0.00% | |

TABLE 5-continued $ED_{50}$ of HPV39N15 VLP for inducing the generation of antibodies against HPV39 and HPV68 (seroconversion) in mice

| Type | Immunizing dose (μg) | Total number of mice | Number of mice with positive conversion | Positive conversion rate | $ED_{50}$ (μg) |
|---|---|---|---|---|---|
| | 0.100 | 8 | 0 | 0.00% | |
| | 0.033 | 8 | 0 | 0.00% | |
| | 0.011 | 8 | 8 | 0.00% | |

TABLE 6

$ED_{50}$ of HPV68N0 VLP for inducing the generation of antibodies against HPV39 and HPV68 (seroconversion) in mice

| Type | Immunizing dose (μg) | Total number of mice | Number of mice with positive conversion | Positive conversion rate | $ED_{50}$ (μg) |
|---|---|---|---|---|---|
| HPV39 | 0.900 | 8 | 0 | 0.00% | >0.9 |
| | 0.300 | 8 | 0 | 0.00% | |
| | 0.100 | 8 | 0 | 0.00% | |
| | 0.033 | 8 | 0 | 0.00% | |
| | 0.011 | 8 | 0 | 0.00% | |
| HPV68 | 0.900 | 8 | 8 | 100.00% | 0.021 |
| | 0.300 | 8 | 8 | 100.00% | |
| | 0.100 | 8 | 7 | 93.75% | |
| | 0.033 | 8 | 7 | 80.00% | |
| | 0.011 | 8 | 1 | 10.00% | |

TABLE 7

$ED_{50}$ of H39N15-68T4 VLP for inducing the generation of antibodies against HPV39 and HPV68 (seroconversion) in mice

| Type | Immunizing dose (μg) | Total number of mice | Number of mice with positive conversion | Positive conversion rate | $ED_{50}$ (μg) |
|---|---|---|---|---|---|
| HPV39 | 0.900 | 8 | 6 | 90.48% | 0.091 |
|  | 0.300 | 8 | 6 | 76.47% |  |
|  | 0.100 | 8 | 6 | 53.85% |  |
|  | 0.033 | 8 | 1 | 7.14% |  |
|  | 0.11 | 8 | 0 | 0.00% |  |
| HPV68 | 0.900 | 8 | 4 | 75.00% | 0.300 |
|  | 0.300 | 8 | 4 | 50.00% |  |
|  | 0.100 | 8 | 2 | 22.22% |  |
|  | 0.033 | 8 | 2 | 9.09% |  |
|  | 0.011 | 8 | 0 | 0.00% |  |

TABLE 8

$ED_{50}$ of the mixed HPV39/HPV68 VLP for inducing the generation of antibodies against HPV39 and HPV68 (seroconversion) in mice

| Type | Immunizing dose (μg) | Total number of mice | Number of mice with positive conversion | Positive conversion rate | $ED_{50}$ (μg) |
|---|---|---|---|---|---|
| HPV39 | 0.900 | 8 | 7 | 97.06% | 0.017 |
|  | 0.300 | 8 | 8 | 96.30% |  |
|  | 0.100 | 8 | 8 | 94.74% |  |
|  | 0.033 | 8 | 8 | 90.91% |  |
|  | 0.011 | 8 | 2 | 22.22% |  |
| HPV68 | 0.900 | 8 | 7 | 96.88% | 0.021 |
|  | 0.300 | 8 | 8 | 96.00% |  |
|  | 0.100 | 8 | 8 | 94.12% |  |
|  | 0.033 | 8 | 7 | 80.00% |  |
|  | 0.011 | 8 | 1 | 10.00% |  |

The results showed that 5 weeks after vaccination of mice, $ED_{50}$ of H39N15-68T4 VLP for inducing the generation of antibodies against HPV39 in mice was comparable to that of HPV39N15 VLP alone, and was significantly superior to that of HPV68N0 VLP alone; and its $ED_{50}$ for inducing the generation of antibodies against HPV68 was slightly weaker than that of HPV68N0 VLP alone, but was significantly superior to that of HPV39N15 VLP alone. This showed that H39N15-68T4 VLP had good cross-immunogenicity and cross-protection against HPV68 and HPV39.

Example 5: Evaluation 2 of Neutralizing Antibody Titer in Serum of Mice Vaccinated with Virus-Like Particles In this experiment, virus-like particles used were H39N15-68T4-70S1 VLP, H39N15-68T4-70S2 VLP, H39N15-68T4-70S3 VLP and H39N15-68T4-70S5 VLP.

In this experiment, vaccination schedule was shown in Table 9. All the mice (6-week old BalB/c female mice) were divided into 3 groups: Aluminum adjuvant group 1 (at an immunizing dose of 5 μg, using aluminum adjuvant), Aluminum adjuvant group 2 (at an immunizing dose of 1 μg, using aluminum adjuvant), and Aluminum adjuvant group 3 (at an immunizing dose of 0.2 μg, using aluminum adjuvant). Each group was further divided into 8 subgroups. The Control subgroups 1, 2 and 3 were vaccinated with HPV39N15 VLP alone, HPV68N0 VLP alone and HPV70N10 VLP alone, respectively, the Control subgroup 4 was vaccinated with the mixed HPV39/HPV68/HPV70 VLP (i.e. a mixture of HPV39N15 VLP, HPV68N0 VLP and HPV70N10 VLP, at a given immunizing dose for each VLP). The Experimental subgroups 1, 2, 3 and 4 were vaccinated with H39N15-68T4-70S1 VLP, H39N15-68T4-70S2 VLP, H39N15-68T4-70S3 VLP and H39N15-68T4-70S5 VLP, respectively.

In Aluminum adjuvant groups 1-3, 5 mice/subgroup were vaccinated by intraperitoneal injection, at an immunizing dose 5 μg, 1 μg, and 0.2 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV39, and HPV68 and HPV70 in serum were analyzed. The analysis results were shown in FIGS. 8A-8C. The results showed that H39N15-68T4-70S2 VLP, H39N15-68T4-70S3 VLP and H39N15-68T4-70S5 VLP could induce the generation of high-titer neutralizing antibodies against HPV39 in mice, and their protective effects were slightly weaker than that of HPV39N15 VLP alone and that of the mixed HPV39/HPV68/HPV70 VLP at the same dose, but were significantly superior to that of HPV68N0 VLP alone and that of HPV70N10 VLP alone at the same dose; and they could induce the generation of high-titer neutralizing antibodies against HPV68 in mice, and their protective effects were comparable to that of HPV68N0 VLP alone and that of the mixed HPV39/HPV68/HPV70 VLP at the same dose, and were significantly superior to that of HPV39N15 VLP alone and that of HPV70N10 VLP alone at the same dose; and they could induce the generation of high-titer neutralizing antibodies against HPV70 in mice, and their protective effects were comparable to that of HPV70N10 VLP alone and that of the mixed HPV39/HPV68/HPV70 VLP at the same dose, and were significantly superior to that of HPV39N15 VLP alone and that of HPV68N0 VLP alone at the same dose. This showed that H39N15-68T4-70S2 VLP, H39N15-68T4-70S3 VLP and H39N15-68T4-70S5 VLP had good cross-immunogenicity and cross-protection against HPV39, HPV68 and HPV70.

TABLE 9

Vaccination schedule

| Group | Antigen for vaccination | Adjuvant | Immunizing dose | Number | Vaccination procedure (week) |
|---|---|---|---|---|---|
| Aluminum adjuvant group 1 | HPV39N15 VLP | aluminum adjuvant | 5 μg | 5 | 0, 2, 4 |
|  | HPV68N0 VLP | aluminum adjuvant | 5 μg | 5 | 0, 2, 4 |

TABLE 9-continued

Vaccination schedule

| Group | Antigen for vaccination | Adjuvant | Immunizing dose | Number | Vaccination procedure (week) |
|---|---|---|---|---|---|
| | HPV70N10 VLP | aluminum adjuvant | 5 μg | 5 | 0, 2, 4 |
| | The mixed HPV39/HPV68/HPV70 VLP | aluminum adjuvant | 5 μg for each VLP | 5 | 0, 2, 4 |
| | H39N15-68T4-70S1 VLP | aluminum adjuvant | 5 μg | 5 | 0, 2, 4 |
| | H39N15-68T4-70S2 VLP | aluminum adjuvant | 5 μg | 5 | 0, 2, 4 |
| | H39N15-68T4-70S3 VLP | aluminum adjuvant | 5 μg | 5 | 0, 2, 4 |
| | H39N15-68T4-70S5 VLP | aluminum adjuvant | 5 μg | 5 | 0, 2, 4 |
| | HPV39N15 VLP | aluminum adjuvant | 1 μg | 5 | 0, 2, 4 |
| | HPV68N0 VLP | aluminum adjuvant | 1 μg | 5 | 0, 2, 4 |
| | HPV70N10 VLP | aluminum adjuvant | 1 μg | 5 | 0, 2, 4 |
| Aluminum adjuvant group 2 | The mixed HPV39/HPV68/HPV70 VLP | aluminum adjuvant | 1 μg for each VLP | 5 | 0, 2, 4 |
| | H39N15-68T4-70S1 VLP | aluminum adjuvant | 1 μg | 5 | 0, 2, 4 |
| | H39N15-68T4-70S2 VLP | aluminum adjuvant | 1 μg | 5 | 0, 2, 4 |
| | H39N15-68T4-70S3 VLP | aluminum adjuvant | 1 μg | 5 | 0, 2, 4 |
| | H39N15-68T4-70S5 VLP | aluminum adjuvant | 1 μg | 5 | 0, 2, 4 |
| | HPV39N15 VLP | aluminum adjuvant | 0.2 μg | 5 | 0, 2, 4 |
| | HPV68N0 VLP | aluminum adjuvant | 0.2 μg | 5 | 0, 2, 4 |
| | HPV70N10 VLP | aluminum adjuvant | 0.2 μg | 5 | 0, 2, 4 |
| Aluminum adjuvant group 3 | The mixed HPV39/HPV68/HPV70 VLP | aluminum adjuvant | 0.2 μg for each VLP | 5 | 0, 2, 4 |
| | H39N15-68T4-70S1 VLP | aluminum adjuvant | 0.2 μg | 5 | 0, 2, 4 |
| | H39N15-68T4-70S2 VLP | aluminum adjuvant | 0.2 μg | 5 | 0, 2, 4 |
| | H39N15-68T4-70S3 VLP | aluminum adjuvant | 0.2 μg | 5 | 0, 2, 4 |
| | H39N15-68T4-70S5 VLP | aluminum adjuvant | 0.2 μg | 5 | 0, 2, 4 |

Example 6: Evaluation 2 of $ED_{50}$ of Virus-Like Particles for Inducing Seroconversion In this experiment, virus-like particles used were H39N15-68T4-70S2 VLP, H39N15-68T4-70S3 VLP and H39N15-68T4-70S5 VLP.

6-Week old BalB/c female mice (8 mice) were vaccinated with aluminum adjuvant by single intraperitoneal injection, wherein H39N15-68T4-70S2 VLP, H39N15-68T4-70S3 VLP and H39N15-68T4-70S5 VLP (at an immunizing dose of 0.900m, 0.300m, 0.100m, 0.033m or 0.011m) were used in the Experimental groups, and HPV39N15 VLP alone, HPV68N0 VLP alone, HPV70N10 VLP alone (at an immunizing dose of 0.900m, 0.300m, 0.100m, 0.033m or 0.011 μg) or the mixed HPV39/HPV68/HPV70 VLP (i.e. a mixture of HPV39N15 VLP, HPV68N0 VLP and HPV70N10 VLP, at an immunizing dose of 0.900m, 0.300m, 0.100m, 0.033m or 0.011m for each VLP); the immunizing volume was 1 mL. In addition, the diluent used to dilute the vaccine was used as a blank control. 8 Mice were vaccinated in each group, and at Week 5 after vaccination, venous blood was collected from eyeball. Antibodies against HPV in the serum were detected, and by Reed-Muench method (Reed L J M H. A simple method of estimating fifty percent endpoints. Am J Hyg. 1938; 27:493-7), $ED_{50}$ for inducing seroconversion (i.e. inducing the generation of antibodies in mice) was calculated for each sample. The results were shown in Tables 10-16.

TABLE 10

$ED_{50}$ of HPV39N15 VLP for inducing the generation of antibodies against HPV39, HPV68 and HPV70 (seroconversion) in mice

| Type | Immunizing dose (μg) | Total number of mice | Number of mice with positive conversion | Positive conversion rate | $ED_{50}$ (μg) |
|---|---|---|---|---|---|
| HPV39 | 0.900 | 8 | 8 | 100.00% | 0.019 |
| | 0.300 | 8 | 8 | 100.00% | |
| | 0.100 | 8 | 8 | 100.00% | |
| | 0.033 | 8 | 7 | 88.89% | |
| | 0.011 | 8 | 1 | 11.11% | |
| HPV68 | 0.900 | 8 | 0 | 11.11% | >0.9 |
| | 0.300 | 8 | 0 | 5.88% | |
| | 0.100 | 8 | 0 | 4.00% | |

TABLE 10-continued

ED$_{50}$ of HPV39N15 VLP for inducing the generation of antibodies against HPV39, HPV68 and HPV70 (seroconversion) in mice

| Type | Immunizing dose (μg) | Total number of mice | Number of mice with positive conversion | Positive conversion rate | ED$_{50}$ (μg) |
|---|---|---|---|---|---|
| | 0.033 | 8 | 1 | 3.13% | |
| | 0.011 | 8 | 0 | 0.00% | |
| HPV70 | 0.900 | 8 | 0 | 11.11% | >0.9 |
| | 0.300 | 8 | 1 | 6.25% | |
| | 0.100 | 8 | 0 | 0.00% | |
| | 0.033 | 8 | 0 | 0.00% | |
| | 0.011 | 8 | 0 | 0.00% | |

TABLE 11

ED$_{50}$ of HPV68N0 VLP for inducing the generation of antibodies against HPV39, HPV68 and HPV70 (seroconversion) in mice

| Type | Immunizing dose (μg) | Total number of mice | Number of mice with positive conversion | Positive conversion rate | ED$_{50}$ (μg) |
|---|---|---|---|---|---|
| HPV39 | 0.900 | 8 | 0 | 20.00% | >0.9 |
| | 0.300 | 8 | 0 | 11.11% | |
| | 0.100 | 8 | 1 | 8.00% | |
| | 0.033 | 8 | 1 | 3.23% | |
| | 0.011 | 8 | 0 | 0.00% | |
| HPV68 | 0.900 | 8 | 8 | 100.00% | 0.021 |
| | 0.300 | 8 | 8 | 100.00% | |
| | 0.100 | 8 | 8 | 100.00% | |
| | 0.033 | 8 | 6 | 77.78% | |
| | 0.011 | 8 | 1 | 10.00% | |
| HPV70 | 0.900 | 8 | 2 | 50.00% | 0.9 |
| | 0.300 | 8 | 2 | 25.00% | |
| | 0.100 | 8 | 0 | 9.09% | |
| | 0.033 | 8 | 2 | 7.14% | |
| | 0.011 | 8 | 0 | 0.00% | |

TABLE 12

ED$_{50}$ of HP70N10 VLP for inducing the generation of antibodies against HPV39, HPV68 and HPV70 (seroconversion) in mice

| Type | Immunizing dose (μg) | Total number of mice | Number of mice with positive conversion | Positive conversion rate | ED$_{50}$ (μg) |
|---|---|---|---|---|---|
| HPV39 | 0.900 | 8 | 2 | 40.00% | >0.9 |
| | 0.300 | 8 | 0 | 12.50% | |
| | 0.100 | 8 | 1 | 8.70% | |
| | 0.033 | 8 | 1 | 3.45% | |
| | 0.011 | 8 | 0 | 0.00% | |
| HPV68 | 0.900 | 8 | 0 | 0.00% | >0.9 |
| | 0.300 | 8 | 0 | 0.00% | |
| | 0.100 | 8 | 0 | 0.00% | |
| | 0.033 | 8 | 0 | 0.00% | |
| | 0.011 | 8 | 0 | 0.00% | |
| HPV70 | 0.900 | 8 | 8 | 100.00% | 0.017 |
| | 0.300 | 8 | 8 | 100.00% | |
| | 0.100 | 8 | 8 | 100.00% | |
| | 0.033 | 8 | 7 | 90.00% | |
| | 0.011 | 8 | 2 | 22.22% | |

TABLE 13

ED$_{50}$ of the mixed HPV39/HPV68/HPV70 VLP for inducing the generation of antibodies against HPV39, HPV68 and HPV70 (seroconversion) in mice

| Type | Immunizing dose (μg) | Total number of mice | Number of mice with positive conversion | Positive conversion rate | ED$_{50}$ (μg) |
|---|---|---|---|---|---|
| HPV39 | 0.900 μg for each VLP | 8 | 8 | 100.00% | 0.021 |
| | 0.300 μg for each VLP | 8 | 8 | 100.00% | |
| | 0.100 μg for each VLP | 8 | 7 | 93.75% | |
| | 0.033 μg for each VLP | 8 | 7 | 80.00% | |
| | 0.011 μg for each VLP | 8 | 1 | 10.00% | |
| HPV68 | 0.900 μg for each VLP | 8 | 8 | 100.00% | 0.019 |
| | 0.300 μg for each VLP | 8 | 8 | 100.00% | |
| | 0.100 μg for each VLP | 8 | 7 | 94.12% | |
| | 0.033 μg for each VLP | 8 | 7 | 81.82% | |
| | 0.011 μg for each VLP | 8 | 2 | 20.00% | |
| HPV70 | 0.900 μg for each VLP | 8 | 8 | 100.00% | 0.021 |
| | 0.300 μg for each VLP | 8 | 8 | 100.00% | |
| | 0.100 μg for each VLP | 8 | 7 | 93.75% | |
| | 0.033 μg for each VLP | 8 | 7 | 80.00% | |
| | 0.011 μg for each VLP | 8 | 1 | 10.00% | |

TABLE 14

ED$_{50}$ of H39N15-68T4-70S2 VLP for inducing the generation of antibodies against HPV39, HPV68 and HPV70 (seroconversion) in mice

| Type | Immunizing dose (μg) | Total number of mice | Number of mice with positive conversion | Positive conversion rate | ED$_{50}$ (μg) |
|---|---|---|---|---|---|
| HPV39 | 0.900 | 8 | 8 | 100.00% | 0.017 |
| | 0.300 | 8 | 7 | 96.15% | |
| | 0.100 | 8 | 8 | 94.74% | |
| | 0.033 | 8 | 8 | 90.91% | |
| | 0.011 | 8 | 2 | 22.22% | |
| HPV68 | 0.900 | 8 | 6 | 100.00% | 0.028 |
| | 0.300 | 8 | 8 | 91.67% | |
| | 0.100 | 8 | 7 | 82.35% | |
| | 0.033 | 8 | 6 | 58.33% | |
| | 0.011 | 8 | 1 | 7.69% | |
| HPV70 | 0.900 | 8 | 7 | 96.30% | 0.033 |
| | 0.300 | 8 | 7 | 90.48% | |
| | 0.100 | 8 | 5 | 70.59% | |
| | 0.033 | 8 | 6 | 50.00% | |
| | 0.011 | 8 | 1 | 6.67% | |

TABLE 15

$ED_{50}$ of H39N15-68T4-70S3 VLP for in

The invention claimed is:

1. A mutated HPV39 L1 protein, wherein as compared with a wild type HPV39 L1 protein,
   (I) the mutated HPV39 L1 protein has the following mutations:
   (1) N-terminal truncation of any number of amino acids from 1 to 25; and
   (2) substitution of amino acid residues at positions of the wild type HPV39 L1 protein which correspond to positions 269-288 of SEQ ID NO: 1 with amino acid residues at the corresponding positions of a L1 protein of a second type of wild-type HPV; or,
   (II) the mutated HPV39 L1 protein has the mutations as defined in (1) and (2), and further has the following mutation:
   (3)(a) substitution of amino acid residues at positions of the wild type HPV39 L1 protein which correspond to positions 117-140 of SEQ ID NO: 1 with amino acid residues at the corresponding positions of a L1 protein of a third type of wild-type HPV; or
   (b) substitution of amino acid residues at positions of the wild type HPV39 L1 protein which correspond to positions 169-181 of SEQ ID NO: 1 with amino acid residues at the corresponding positions of a L1 protein of a third type of wild-type HPV; or
   (c) substitution of amino acid residues at positions of the wild type HPV39 L1 protein which correspond to positions 347-358 of SEQ ID NO: 1 with amino acid residues at the corresponding positions of a L1 protein of a third type of wild-type HPV,
   wherein said corresponding positions are determined by optimal alignment of the sequences being compared, and wherein the L1 proteins of the second type of wild-type HPV comprises different amino acid sequences at a region corresponding to positions 269-288 of SEQ ID. NO.1, and the L1 protein of the third type of wild-type HPV comprises different amino acid sequences at regions correspondence to positions 117-140, 169-181, or 347-358 of SEQ ID NO.1.

2. An isolated nucleic acid, encoding the mutated HPV39 L1 protein according to claim 1.

3. A vector comprising the isolated nucleic acid according to claim 2.

4. An isolated host cell comprising the isolated nucleic acid according to claim 2 and/or a vector comprising the isolated nucleic acid according to claim 2.

5. An HPV virus-like particle, comprising or consisting of the mutated HPV39 L1 protein according to claim 1.

6. A composition, comprising:
   (i) the mutated HPV39 L1 protein according to claim 1, or
   (ii) an isolated nucleic acid encoding the mutated HPV39 L1 protein as described in (i), or
   (iii) a vector comprising the isolated nucleic acid as described in (ii), or
   (iv) an isolated host cell comprising the isolated nucleic acid as described in (ii) and/or the vector comprising the isolated nucleic acid as described in (iii), or
   (v) an HPV virus-like particle comprising or consisting of the mutated HPV39 L1 protein as described in (i).

7. A pharmaceutical composition or vaccine, comprising the HPV virus-like particle according to claim 5, and optionally a pharmaceutically acceptable carrier and/or excipient.

8. A method for preparing the mutated HPV39 L1 protein according to claim 1, comprising expressing the mutated HPV39 L1 protein in a host cell, and then recovering the mutated HPV39 L1 protein from a culture of the host cell.

9. A method for preparing a vaccine, comprising combining the HPV virus-like particle according to claim 5 with a pharmaceutically acceptable carrier and/or excipient.

10. A method for preventing HPV infection or a disease caused by HPV infection, comprising administering to a subject a prophylactically effective amount of the HPV virus-like particle according to claim 5 or a pharmaceutical composition or vaccine comprising the HPV virus-like particle according to claim 5 and optionally a pharmaceutically acceptable carrier and/or excipient.

11. The mutated HPV39 L1 protein according to claim 1, wherein the mutated HPV39 L1 protein is characterized by one or more of the following items:
  (i) the mutated HPV39 L1 protein has 3, 5, 8, 10, 12, 15, 18, 20 or 22 amino acids truncated at N-terminal, as compared with the wild type HPV39 L1 protein;
  (ii) the second type of wild-type HPV is HPV68;
  (iii) the amino acid residues at the corresponding positions as described in (2) are amino acid residues at positions 270-289 of a wild type HPV68 L1 protein;
  (iv) the third type of wild-type HPV is HPV70;
  (v) the amino acid residues at the corresponding positions as described in (3) (a) are amino acid residues at positions 117-141 of a wild type HPV70 L1 protein;
  (vi) the amino acid residues at the corresponding positions as described in (3) (b) are amino acid residues at positions 170-182 of a wild type HPV70 L1 protein;
  (vii) the amino acid residues at the corresponding positions as described in (3) (c) are amino acid residues at positions 348-359 of a wild type HPV70 L1 protein;
  (viii) the wild type HPV39 L1 protein has an amino acid sequence as set forth in SEQ ID NO: 1;
  (ix) the wild type HPV68 L1 protein has an amino acid sequence as set forth in SEQ ID NO: 2;
  (x) the wild type HPV70 L1 protein has an amino acid sequence as set forth in SEQ ID NO: 3.

12. The mutated HPV39 L1 protein according to claim 1, wherein the mutated HPV39 L1 protein has an amino acid sequence selected from the group consisting of: SEQ ID NO: 7, 10, 11 and 12.

13. The isolated nucleic acid according to claim 2, wherein the isolated nucleic acid has a nucleotide sequence selected from the group consisting of: SEQ ID NO: 19, 22, 23 and 24.

14. The pharmaceutical composition or vaccine according to claim 7, wherein the HPV virus-like particle is present in an amount effective for preventing HPV infection or a disease caused by HPV infection.

15. The pharmaceutical composition or vaccine according to claim 14, wherein the HPV infection is infection by one or more HPV types, and/or, the disease caused by HPV infection is selected from the group consisting of cervical cancer and condyloma acuminatum.

16. The pharmaceutical composition or vaccine according to claim 15, wherein the HPV infection is selected from: HPV39 infection, HPV68 infection, HPV70 infection and any combination thereof.

17. The method according to claim 8, wherein the host cell is *E. coli*.

18. The method according to claim 17, wherein the method comprises the steps of: expressing the mutated HPV39 L1 protein in *E. coli*, and then obtaining the mutated HPV39 L1 protein by purifying a lysate supernatant of the *E. coli*.

19. The method according to claim 10, wherein the HPV infection is infection by one or more HPV types, and/or, the disease caused by HPV infection is selected from the group consisting of cervical cancer and condyloma acuminatum.

20. The method according to claim 19, wherein the HPV infection is selected from: HPV39 infection, HPV68 infection, HPV70 infection and any combination thereof.

* * * * *